US008501463B2

(12) United States Patent
Cox et al.

(10) Patent No.: US 8,501,463 B2
(45) Date of Patent: Aug. 6, 2013

(54) ANAEROBIC PRODUCTION OF HYDROGEN AND OTHER CHEMICAL PRODUCTS

(75) Inventors: Marion E. Cox, Morgan Hill, CA (US); Laura M. Nondorf, Morgan Hill, CA (US); Steven M. Cox, Morgan Hill, CA (US)

(73) Assignee: Anaerobe Systems, Morgan Hill, CA (US)

( * ) Notice: Subject to any disclaimer, the term of this patent is extended or adjusted under 35 U.S.C. 154(b) by 1347 days.

(21) Appl. No.: 11/912,881

(22) PCT Filed: Apr. 27, 2006

(86) PCT No.: PCT/US2006/016332
§ 371 (c)(1),
(2), (4) Date: Jun. 23, 2008

(87) PCT Pub. No.: WO2006/119052
PCT Pub. Date: Nov. 9, 2006

(65) Prior Publication Data
US 2008/0311640 A1 Dec. 18, 2008

Related U.S. Application Data

(60) Provisional application No. 60/678,101, filed on May 3, 2005, provisional application No. 60/677,856, filed on May 3, 2005, provisional application No. 60/678,077, filed on May 3, 2005, provisional application No. 60/678,100, filed on May 3, 2005, provisional application No. 60/678,098, filed on May 3, 2005, provisional application No. 60/677,998, filed on May 3, 2005.

(51) Int. Cl.
| C12M 1/07 | (2006.01) |
| C12M 1/12 | (2006.01) |
| C12P 3/00 | (2006.01) |
| C12P 1/04 | (2006.01) |
| C12N 1/20 | (2006.01) |
| C12M 1/36 | (2006.01) |
| C12M 1/38 | (2006.01) |
| C12M 1/107 | (2006.01) |

(52) U.S. Cl.
USPC ............... 435/303.2; 435/168; 435/252.1; 435/286.1; 435/290.4

(58) Field of Classification Search
USPC ............ 435/168, 252.1, 286.1, 290.4, 303.2
See application file for complete search history.

(56) References Cited

U.S. PATENT DOCUMENTS

| 5,350,685 | A | 9/1994 | Taguchi et al. | |
| 5,464,539 | A | 11/1995 | Ueno et al. | |
| 6,090,266 | A | 7/2000 | Roychowdhury | |
| 6,251,643 | B1 | 6/2001 | Hansen et al. | |
| 6,299,774 | B1 * | 10/2001 | Ainsworth et al. | ........... 210/603 |
| 6,342,378 | B1 | 1/2002 | Zhang et al. | |
| 6,569,332 | B2 * | 5/2003 | Ainsworth et al. | ........... 210/603 |
| 2004/0050778 | A1 | 3/2004 | Noike et al. | |
| 2004/0115782 | A1 | 6/2004 | Paterek | |

FOREIGN PATENT DOCUMENTS

WO WO-2006-119052 A2 11/2006

OTHER PUBLICATIONS

Liu et al., 2004. Effects of Culture and Medium Conditions on Hydrogen Production from Starch Using Anaerobic Bacteria. Journal of Bioscience and Bioengineering, vol. 98, No. 4, pp. 251-256.*
Zhang et al., Distributed Computer Control of Penicillin Fermentation Industrial Production. Proceedings of the IEEE International Conference on Industrial Technology, 1996, pp. 52-56.*
New Brunswick, an eppenforf Company, pp. 1-3, http://www.nbsc.com/BioFlo-415-SIP-Fermentor.aspx Printed Mar. 26, 2012.*
Prell et al. 2000. Lower layer control of the CSTR, a basic part of the bioreactor control system. 27th International Conference of Slovak Society of Chemical Engineering, Tatranske Matliare, Slovakia, Proc. p. 30, Lecture No. R16.*
Claassen, P.A.M. et al., "Utilisation of biomass for the supply of energy carriers," Appl. Microbiol. Biotechnol. 52:741-755 (1999).
Gorman, J., "Hydrogen: The Next Generation, Cleaning up production of a future fuel," 8 pages retrieved from Internet on Oct. 27, 2004 http://www.sciencenews.org/articles/2w0021012/bob11.asp.
Henley, M. et al., "Microbial Hydrogen Production," 3 pages retrieved from Internet on Oct. 27, 2004 http://www.afrlhorizons.com/Briefs/Jun03/ML0227.html.
Levin, D.B. et al., "Biohydrogen production: prospects and limitations to practical application," Intl. J. Hydrogen Energy 29:173-185 (2004).
Logan, B. et al., "Biological Hydrogen Production as a Sustainable Green Technology for Pollution Prevention," 2 pages retrieved from Internet on Oct. 27, 2004 http://www.engr.psu.edu/h2e/Pub/Logan_etal_1.htm.
Logan, B. et al., "Biological Hydrogen Production in a Bioreactor," 1 page retrieved from Internet on Oct. 27, 2004 http://www.engr.psu.edu/h2e/Pub/Logan_etal_1.htm.

(Continued)

Primary Examiner — Jon P Weber
Assistant Examiner — Kailash C Srivastava
(74) Attorney, Agent, or Firm — Wilson, Sonsini, Goodrich & Rosati

(57) ABSTRACT

Described herein are methods for producing chemical products by anaerobically fermenting a particular biomass using anaerobic bacteria. Such chemical products include hydrogen and other gases, acetic acid and other volatile organic acids, solvents, solids, and salts of volatile organic acids.

5 Claims, 18 Drawing Sheets

OTHER PUBLICATIONS

Logan, B. et al., "Biological Hydrogen Production Measured in Batch Anaerobic Respirometers," Environ. Sci. Technol. 36:2530-2535 (2002).

Oh, S.E. et al., "The Relative Effectiveness of pH Control and Heat Treatment for Enhancing Biohydrogen Gas Production," Environ. Sci. Technol. 37:5186-5190 (2003).

Raskin, S.S. et al., "Hydrogen Production by Anaerobic Microbial Communities Exposed to Repeated Heat Treatments," Proceedings of the 2002 U.S. DOE Hydrogen Program Review, NREL/CP-610-32405, 17 pages.

Regan, J. et al., "Genetic Engineering of *Chlostridium acetobutylicum* for Enhanced Production of Hydrogen Gas," 1 page retrieved from Internet on Oct. 27, 2004 http://www.engr.psu.edu/h2e/Pub/Regan_etal_1.htm.

Ren, N.Q. et al., "Hydrogen Production from Molasses by Anaerobic Activated Sludge in Pilot-Scale Bioreactor," Poster Presentation 2-27 from 26$^{th}$ Symposium on Biotechnology for Fuels and Chemicals, May 9-12, 2004, Chattanooga, TN USA, retrieved from Internet on Dec. 17, 2004, http://www.ct.ornl.gov/symposium/index_files/2abstracts/2_27.htm.

Taguchi, F. et al., "Continuous Hydrogen Production by *Clostridium* sp. Strain No. 2 from Cellulose Hdrolysate in an Aqueous Two-Phase System," J. Fermentation and Bioengineering 82(1):80-83 (1996).

Van Ginkel, S. et al., "Role of Initial Sucrose and pH Levels on Natural, Hydrogen-Producing, Anaerobe Germination," Proceedings of the 2001 DOE Hydrogen Program Review, NREL/CP-570-3053,15 pages.

Hussy et al., "Continuous Fermentative Hydrogen Production from a Wheat Starch Co-Product by Mixed Microfloara," Biotech. Bioeng. 84(6):619-626 (2003).

Lay, J.J. et al., "Influence of chemical nature of organic wastes on their conversion to hydrogen by heat-shock digested sludge," Intl. J. Hydrogen Energy 28:1361-1367 (2003).

Taguchi et al., "Direct conversion of ceullolosic materials to hydrogen by *Clostridium* sp. Strain No. 2," Enzyme and Microbial Tech. 17:147-150 (1995).

Yokol, H. et al., "Microbial production of hydrogen from starch-manufacturing wastes," Biomass and Bioenergy 22:389-395 (2002).

PCT/US06/16332 Search Report Dated Sep. 12, 2008.

Abraham et al., "Commissioning and Re-Design of a Class A Thermal Hydrolysis Facility for Pre-Treatment of Primary and Secondary Sludge Prior to Anaerobic Digestion," 76$^{th}$ Annual Water Environment Federation Technical Exposition and Conference, XP002660698, pp. 1-14 (2003) Retrieved from the Internet: URL:http://www.cambi.no/photoalbum/view2/P3NpemU9b3JnJmlkPTIyMDAzMCZ0eXB1PTE *abstract* *p. 2, last paragraph-p. 3, last paragraph.

Wang et al., "Producing Hydrogen from Wastewater Sludge by *Clostridium* Bifermentans," Journal of Biotechnology, vol. 102, No. 1, pp. 83-92 (2003).

EP06751822.5 Extended European Search Report mailed Oct. 18, 2011.

* cited by examiner

General Information

*Bilophila wadsworthia* is a common inhabitant of the human colon and has been associated with appendicitis and other local sites of inflammation in humans. It is a slow-growing, asaccharolytic, and obligately anaerobic bacillus, making it somewhat difficult for routine culture and identification (1, 2). It has been cultured from the colon or feces of 50 to 60% of healthy adult humans, but generally in low numbers (ca. 103 to 106 CFU/g [wet weight]) (1, 2). It has been strongly associated with pathogenic infections of intra-abdominal sites, such as appendicitis and cholecystitis (4), as well as extra-intestinal sites, such as otitis (10, 23). However, challenge-exposure studies in laboratory animals have not been reported. Endotoxic and procoagulant activities have been identified in *B. wadsworthia* (15), and an in vitro study suggested that it may be able to attach to epithelial cells of the colon (8). Separate subgroups or strains of *B. wadsworthia* have been indicated by DNA fingerprinting studies (9). The possible isolation of *B. wadsworthia* from healthy or diseased nonhuman hosts has not previously been reported. Molecular studies, such as the identification of possible invasion or attachment genes or receptors, have not been reported.

Colony Morphology

Growth Conditions: cultured on Brucella blood agar after 72 hr.
Diameter: 0.6-0.8 mm.
Form: circular or slightly irregular
Elevation: raised
Margin: erose; may be slightly spreading
Color: gray
Density: translucent

*Bilophila wadsworthia*

Description
General Information
Colony Morphology
Cellular Morphology
References Photos
Gram stain
Blood plate
BBE/LKV plate

Figure 5

ANAEROBIC PRODUCTION OF HYDROGEN AND OTHER CHEMICAL PRODUCTS

CROSS REFERENCE

This application claims the benefit of U.S. provisional application Ser Nos. 60/678,101, filed May 3, 2005; 60/677,856, filed May 3, 2005; 60/678,077, filed May 3, 2005; 60/678,100, filed May 3, 2005; 60/678,098, filed May 3, 2005; and 60/677,998, filed May 3, 2005, all of which are incorporated by reference in their entirety.

FIELD OF THE INVENTION

The methods and compositions described herein are directed to the production of hydrogen and other chemical products via the anaerobic bacterial fermentation of biomass, and the production of hydrogen and other chemical products via bacterial conversion of products obtained from anaerobic fermentation.

BACKGROUND OF THE INVENTION

Hydrogen has high energy content, with water being the product resulting from combustion of hydrogen with oxygen. As such, hydrogen represents a potentially ideal fuel source. However, the use of hydrogen as a viable alternative energy source remains challenging, because many methods for producing hydrogen, such as water electrolysis, and petroleum reforming, are economically and energetically intense.

SUMMARY OF THE INVENTION

In one aspect are methods of preparing nutrients for use in anaerobic production of hydrogen. In another aspect are nutrients for use in the anaerobic production of hydrogen, wherein the nutrients are prepared by methods, which include, but are not limited to concentrating, sterilization and deoxygenation.

In one aspect are isolation/enrichment systems for selecting bacteria for use in anaerobic hydrogen production, wherein the bacterial strains are selected for their ability to utilize biomass as nutrients and produce hydrogen gas and other chemical products. In another aspect is an apparatus for selecting bacteria for use in anaerobic hydrogen production comprising a sealed chamber capable of providing an appropriate environment and growing conditions.

In one aspect is a Knowledge Management System used to identify bacteria for use in anaerobic production of hydrogen from using biomass, wherein bacteria are identified by collecting appropriate information from various bacterial species and deriving a probabilistic model from the information. In another aspect is a computer program product to obtain candidate bacterial species for use in the anaerobic production of hydrogen and other chemical products from a particular biomass.

In one aspect are chemical products produced by anaerobically fermenting biomass with bacteria. In another aspect are chemical products formed by admixing hydrogen, a starting material and a catalyst, wherein the hydrogen is produced by anaerobically fermenting a biomass with bacteria. In another aspect are chemical products formed by admixing a mineral and a volatile organic acid, wherein the volatile organic acid is produced by anaerobically fermenting a biomass with bacteria.

In one aspect are anaerobic fermentation apparatuses which use bacteria for anaerobically fermenting a biomass into chemical products. In another aspect are assemblages which comprise sources of steam; turbines; and digesters.

In one aspect is the use of bacteria for the production of hydrogen and other chemical products. In another aspect biomass prepared for use in hydrogen production has been sterilized, deoxygenated, concentrated, detoxificated, and/or pre-digested while optimal bacterial strains for anaerobic fermentation of the biomass have been selected by means of a Knowledge Management System, and selected and isolated using an isolation/enrichment system.

Bacterial Strains

In further or alternative embodiments of all aspects described herein using bacterial strains to anaerobically ferment biomass and obtain chemical products therefrom, the bacterial strains are substantially purified anaerobic bacteria and such substantially purified bacterial strains are selected to anaerobically ferment the biomass, and in still further or alternative embodiments of all aspects, the substantially purified bacterial strains are selected from the group consisting of *Acetivibrio cellulolyticus, Acetivibrio cellulosolvens, Acetivibrio ethanolgignens, Acetivibrio multivorans, Acetoanaerobium noterae, Acetofilamentum rigidum, Acetogenium kivui, Acetomicrobium faecale, Acetomicrobium flavidum, Acetothermus paucivorans, Acidaminobacter hydrogenoformans, Anaerobiospirillum succiniciproducens, Anaerobiospirillum ihomasii, Anaerorhabdus furcosa, Anaerovibrio burkinabensis, Anaerovibrio glycerini, Anaerovibrio lipolyticus, Atopobiumfossor, Atopobium minutum, Atopobium parvulum, Atopobium rimae, Atopobium vaginae, Bacteroides acidifaciens, Bacteroides amylophilus, Bacteroides asaccharolyticus Bacteroides bivius, Bacteroides buccae, Bacteroides buccalis, Bacteroides caccae Bacteroides capillosus, Bacteroides capillus, Bacteroides cellulosolvens, Bacteroides coagulans, Bacteroides corporis, Bacteroides denticola, Bacteroides disiens, Bacteroides distasonis, Bacteroides eggerthii, Bacteroides endodontalis, Bacteroides forsythus, Bacteroides fragilis, Bacteroides furcosus, Bacteroides galacturonicus, Bacteroides gingivalis, Bacteroides gracilis, Bacteroides helcogenes, Bacteroides heparinolyticus, Bacteroides hypermegas, Bacteroides intermedius, Bacteroides levii, Bacteroides loescheii, Bacteroides macacae, Bacteroides melaminogenicus, Bacteroides meloninogenicus subsp. intermedius, Bacteroides melaminogenicus subsp. macaca, Bacteroides melaminogenicus subsp. melaninogenicus, Bacteroides merdae, Bacteroides microfusus, Bacteroides multiacidus, Bacteroides nodosus, Bacteroides ochraceus, Bacteroides oralis, Bacteroides oris, Bacteroides oulorum, Bacteroides ovatus, Bacteroides pectinophilus, Bacteroides pentosaceus, Bacteroides pneumosintes, Bacteroides polypragmatus, Bacteroides praeacutus, Bacteroides putredinis, Bacteroides pyogenes, Bacteroides ruminicola, Bacteroides ruminicola subsp. brevis, Bacteroides ruminicola subsp. ruminicola, Bacteroides salivosus, Bacteroides splanchnicus, Bacteroides stercoris, Bacteroides succinogenes, Bacteroides suis, Bacteroides tectus, Bacteroides termitidis, Bacteroides thetaiotaomicron, Bacteroides uniformis, Bacteroides ureolyticus, Bacteroides veroralis, Bacteroides vulgatus, Bacteroides xylanolyticus, Bacteroides zoogleoformans, Bifidobacterium adolescentis, Bifidobacterium angulatum, Bifidobacterium animalis, Bifidobacterium animalis subsp. animalis, Bifidobacterium animalis subsp. lactis, Bifidobacterium asteroids, Bifidobacterium bifidum, Bifidobacterium bourn, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacterium glo-*

*bosum, Bifidobacterium indicum, Bifidobacterium infantis, Bifidobacterium inopinatum, Bifidobacterium lactis, Bifidobacterium longum, Bifidobacterium magnum, Bifidobacterium merycicum, Bifidobacterium minimum, Bifidobacterium pseudocatenulatum, Bifidobacterium pseudolongum, Bifidobacterium pseudolongum* subsp. *globosum, Bifidobacterium pseudolongum* subsp. *pseudolongum, Bifidobacterium psychraerophilum, Bifidobacterium pullorum, Bifidobacterium ruminantium, Bifidobacterium saeculare, Bifidobacterium scardovii, Bifidobacterium subtile, Bifidobacterium suis, Bifidobacterium thermacidophilum, Bifidobacterium thermacidophilum* subsp. *porcinum, Bifidobacterium thermacidophilum* subsp. *thermacidophilum, Bifidobacterium thermophilum, Bilophila wadsworthia, Butyrivibrio crossotus, Butyrivibrio fibrisolvens, Butyrivibrio hungatei, Campylobacter butzleri, Campylobacter cinaedi, Campylobacter coli, Campylobacter concisus, Campylobacter cryaerophilus, Campylobacter curvus, Campylobacter fennelliae, Campylobacter fetus, Campylobacter fetus* subsp. *fetus, Campylobacter fetus* subsp. *venerealis, Campylobacter gracilis, Campylobacter helveticus, Campylobacter horninis, Campylobacter hyoilei, Campylobacter hyointestinalis, Campylobacter hyointestinalis* subsp. *hyointestinalis, Campylobacter hyointestinalis* subsp. *lawsonii, Campylobacter insulaenigrae, Campylobacter jejuni, Campylobacter jejuni* subsp. *doylei, Campylobacter jejuni* subsp. *jejuni, Campylobacter lanienae, Campylobacter lari, Campylobacter mucosalis, Campylobacter mustelae, Campylobacter nitrofigilis, Campylobacter pylori, Campylobacter pylori* subsp. *mustelae, Campylobacter pylori* subsp. *pylori, Campylobacter rectus, Campylobacter showae, Campylobacter sputorum, Campylobacter sputorum* subsp. *bubulus, Campylobacter sputorum* subsp. *mucosalis, Campylobacter sputorum* subsp. *sputorum, Campylobacter upsaliensis, Catonella morbi, Centipeda periodontii, Dialister invisus, Dialister pneumosintes, Dichelobacter nodosus, Fervidobacterium gondwanens, Fervidobacterium islandicum, Fervidobacterium nodosum, Fervidobacterium pennivorans, Fibrobacter intestinalis, Fibrobacter succinogenes, Fibrobacter succinogenes* subsp. *Elongatus, Fibrobacter succinogenes* subsp. *succinogenes, Fusobacterium alocis, Fusobacterium canifelinum, Fusobacterium equinum, Fusobacterium gonidiaformans, Fusobacterium mortiferum, Fusobacterium naviforme, Fusobacterium necrogenes, Fusobacterium necrophorum, Fusobacterium necrophorum* subsp. *funduliforme, Fusobacterium necrophorum* subsp. *necrophorum, Fusobacterium nucleatum, Fusobacterium nucleaturn* subsp. *animalis, Fusobacterium nucleatum* subsp. *fusiforme, Fusobacterium nucleatum* subsp. *nucleatum, Fusobacterium nucleatum* subsp. *polymorphum, Fusobacterium nucleatum* subsp. *vincentii, Fusobacterium perfoetens, Fusobacterium periodonticum, Fusobacterium plautii, Fusobacterium polysaccharolyticum, Fusobacterium prausnitzii, Fusobacterium pseudonecrophorum, Fusobacterium russii, Fusobacterium simiae, Fusobacterium sulci, Fusobacterium ulcerans, Fusobacterium varium, Halanaerobacter chitinivorans, Halanaerobacter lacunarum, Halanaerobacter salinarius, Halanaerobium acetethylicum, Halanaerobium alcaliphilum, Halanaerobium congolense, Halanaerobium fermentans, Halanaerobium kushneri, Halanaerobium lacusrosei, Halanaerobium praevalens, Halanaerobium saccharolyticum, Halanaerobium saccharolyticum* subsp. *Saccharolyticum, Halanaerobium saccharolyticum* subsp. *senegalense, Halanaerobium salsuginis, Ilyobacter delafieldii, Ilyobacter insuetus, Ilyobacter polytropus, Ilyobacter tartaricus, Johnsonella ignava, Lachnobacterium bovis, Leptotrichia buccalis, Leptotrichia goodfellowii, Leptotrichia hofstadii, Leptotrichia shahii, Leptotrichia trevisanii, Leptotrichia wadei, Malonomonas rubra, Megamonas hypermegale, Mitsuokella dentalis, Mitsuokella jalaludinii, Mitsuokella multacida, Oxalobacter formigenes, Oxalobacter vibrioformis, Pectinatus cerevisiiphilus, Pectinatus frisingensis, Pectinatus portalensis, Pelobacter acetylenicus, Pelobacter acidigallici, Pelobacter carbinolicus, Pelobacter massiliensis, Pelobacterpropionicus, Pelobacter venetianus, Porphyromonas asaccharolytica, Poiphyromonas cangingivalis, Porphyromonas canoris, Porphyromonas cansulci, Porphyromonas catoniae, Porphyromonas circumdentaria, Porphyromonas crevioricanis, Poiphyromonas endodontalis, Porphyromonas gingivalis, Porphyromonas gingivicanis, Porphyromonas gulae, Poiphyromonas levii, Porphyromonas macacae, Porphyromonas salivosa, Porphyromonas uenonis, Prevotella albensis, Prevotella bivia, Prevotella brevis, Prevotella bryantii, Prevotella buccae, Prevotella buccalis, Prevotella corporis, Prevotella dentalis, Prevotella denticola, Prevotella disiens, Prevotella enoeca, Prevotella heparinolytica, Prevotella intermedia, Prevotella loescheii, Prevotella melaminogenica, Prevotella multiformis, Prevotella nigrescens, Prevotella oralis, Prevotella oris, Prevotella oulorum, Prevotella pollens, Prevotella ruminicola, Prevotella salivae, Prevotella shahii, Prevotella tannerae, Prevotella veroralis, Prevotella zoogleoformans, Propionibacterium acidipropionici, Propionibacterium acnes, Propionibacterium australiense, Propionibacterium avidum, Propionibacterium cyclohexanicum, Propionibacterium freudenreichii, Propionibacterium freudenreichii* subsp. *Freudenreichii, Propionibacterium freudenreichii* subsp. *shermanii, Propionibacterium granulosum, Propionibacterium innocuum, Propionibacterium jensenii, Propionibacterium lymphophilum, Propionibacterium microaerophilum, Propionibacterium propionicum, Propionibacterium thoenii, Propionigenium maris, Propionigenium modestum, Propionispira arboris, Rikenella microfusus, Roseburia cecicola, Roseburia intestinalis, Ruminobacter amylophilus, Sebaldella termitidis, Selenomonas acidaminovorans, Selenomonas artemidis, Selenomonas dianae, Selenomonas flueggei, Selenomonas infelix, Selenomonas lacticifex, Selenomonas lipolytica, Selenomonas noxia, Setenomonas ruminantium, Selenornonas ruminantium* subsp. *lactilytica, Selenomonas ruminantium* subsp. *ruminantium, Selenomonas sputigena, Sporomusa acidovorans, Sporomusa aerivorans, Sporomusa malonica, Sporomusa ovata, Sporomusa paucivorans, Sporomusa silvacetica, Sporomusa sphaeroides, Sporomusa termitida, Succinimonas amylolytica, Sitccinivibrio dextrinosolvens, Syntrophobacter fumaroxidans, Syntrophobacter pfennigii, Syntrophobacter wolinii, Syntrophomonas curvata, Syntrophomonas erecta, Syntrophomonas sapovorans, Syntrophomonas wolfei, Syntrophomonas wolfei, Sutterella stercoricanis, Sutterella wadsworthensi, Saponavida, Thermobacteroides acetoethylicus, Thermobacteroides leptospartum, Thermobacteroides proteolyticus, Thermosipho africanus, Thermosipho atlanticus, Thermosipho geolei, Thermosipho japonicus, Thermosipho melanesiensis, Thermotoga elfi, Thermotoga hypogea, Thermotoga lettingae, Thermotoga maritima, Thermotoga naphthophila, Thermotoga neapolitana, Thermotoga petrophila, Thermotoga subterranea, Thermotoga thermarum, Tissierella creatinini, Tissierella creatinophila, Tissierella praeacuta, Wolinella curva, Wolinella recta, Wolinella succinogenes, Zymophilus paucivorans, Zymophilus raffinosivorans, Desulfobacter curvatus, Desulfobacter halotolerans, Desulfobacter hydrogenophilus, Desulfobacter latus, Desulfobacter postgatei, Desulfobacter vibrioformis, Desulfobacterium anilini, Desulfobacterium autotrophicum, Desulfobacterium catecholi-* cum, Desulfobacterium cetonicum, Desulfobacterium indolicum, Desulfobacterium macestii, Desulfobacterium phenolicum, Desulfobulbus elongatus, Desulfobulbus mediterraneus, Desulfobulbus propionicus, Desulfobulbus rhabdoformis, Desulfococcus biacutus, Desulfococcus multivorans, Desulfomicrobium apsheronum, Desulfomicrobium baculatum, Desulfomicrobium escambiense, Desulfomicrobium macestii, Desulfomicrobium norvegicum, Desulfomicrobium oralem, Desulfomonas pigra, Desulfomonile limimaris, Desulfomonile tiedjei, Desulfonema ishimotonii, Desulfonema limicola, Desulfonema magnum, Desulfosarcina variabilis, Desulfotomaculum acetoxidans, Desulfotomaculum aeronauticum, Desulfotomaculum alkaliphilum, Desulfotomaculum antarcticum, Desulfotomaculum auripigmentum, Desulfotomaculum australicum, Desulfotomaculum geothermicum, Desulfotomaculum gibsoniae, Desulfotomaculum guttoideum, Desulfotomaculum halophilum, Desulfotomaculum kuznetsovii, Desulfotomaculum luciae, Desulfotomaculum nigrificans, Desulfotomaculum orientis, Desulfotomaculum putei, Desulfotomaculum ruminis, Desulfotomaculum sapomandens, Desulfotomaculum solfataricum, Desulfotomaculum thermoacetoxidans, Desulfotomaculum thermobenzoicum, Desulfotomaculum thermobenzoicum subsp. thermobenzoicum, Desulfotomaculum thermobenzoicum subsp. thermosyntrophicum, Desulfotomaculum thermocisternum, Desulfotomaculum thermosapovorans, Desulfovibrio acrylicus, Desulfovibrio aespoeensis, Desulfovibrio africanus, Desulfovibrio alaskensis, Desulfovibrio alcoholivorans, Desulfovibrio aminophilus, Desulfovibrio baarsii, Desidfovibrio baculatus, Desulfovibrio bastinii, Desulfovibrio burkinensis, Desulfovibrio carbinolicus, Desulfovibrio cuneatus, Desulfovibrio dechloracetivorans, Desulfovibrio desulfuricans, Desulfovibrio desulfuricans subsp. aestuarii, Desulfovibrio desulfuricans subsp. desulfuricans, Desulfovibrio fructosivorans, Desulfovibrio furfuralis, Desulfovibrio gabonensis, Desulfovibrio giganteus, Desulfovibrio gigas, Desidfovibrio gracilis, Desulfovibrio halophilus, Desulfovibrio hydrothermalis, Desulfovibrio indonesiensis, Desulfovibrio inopinatus, Desidfovibrio intestinalis, Desulfovibrio litoralis, Desulfovibrio longreachensis, Desulfovibrio longus, Desulfovibrio magneticus, Desulfovibrio mexicanus, Desulfovibrio oxyclinae, Desulfovibrio piger, Desulfovibrio profundus, Desulfovibrio putealis, Desulfovibrio salexigens, Desulfovibrio sapovorans, Desulfovibrio senezii, Desulfovibrio simplex, Desulfovibrio sulfadismutans, Desulfovibrio termitidis, Desulfovibrio thermophilus, Desulfovibrio vietnamensis, Desulfovibrio vulgaris, Desulfovibrio vulgaris subsp. oxamicus, Desulfovibrio vulgaris subsp. vulgaris, Desulfovibrio zosterae, Desulfurella acetivorans, Desulfurella kamchalkensis, Desulfurella multipotens, Desulfurella propionica, Desulfuromonas acetexigens, Desulfuromonas acetoxidans, Desulfuromonas chloroethenica, Desulfuromonas paimitatis, Desulfuromonas tkiophila, Thermodesulfobacterium commune, Thermodesulfobacterium hveragerdense, Thermodesulfobacterium hydrogeniphilum, Thermodesulfobacterium thermophilum, Acidaminococcus fermentans, Megasphaera cerevisiae, Megasphaera elsdenii, Megasphaera micronuciformis Syntrophococcus sucromutans, Veillonella alcalescens, Veillonella alcalescens subsp. alcalescens, Veillonella alcalescens subsp. criceti, Veillonella alcalescens subsp. dispar, Veillonella alcalescens subsp. ratti, Veillonella atypica, Veillonella caviae, Veillonella criceti, Veillonella dispar, Veillonella montpellierensis, Veillonella parvula, Veillonella parvula subsp. atypical, Veillonella parvula subsp. parvula, Veillonella parvula subsp. rodentium, Veillonella ratti, Veillonella rodentium, Coprococcus catu, Coprococcus comes, Coprococcus eutactus, Peptococcus asaccharolyticus, Peptococcus glycinophilus, Peptococcus heliotrinreducens, Peptococcus indolicus, Peptococcus magnus, Peptococcus niger, Peptococcus prevotii, Peptococcus saccharolyticus, Peptostreptococcus anaerobius, Peptostreptococcus asaccharolyticus, Peptostreptococcus barnesae, Peptostreptococcus harei, Peptostreptococcus heliotrinreducens, Peptostreptococcus hydrogenalis, Peptostreptococcus indolicus, Peptostreptococcus ivorii, Peptostreptococcus lacrimalis, Peptostreptococcus lactolyticus, Peptostreptococcus magnus, Peptostreptococcus micros, Peptostreptococcus octavius, Peptostreptococcus parvulus, Peptostreptococcus prevotii, Peptostreptococcus productus, Peptostreptococcus tetradius, Peptostreptococcus vaginalis, Ruminococcus albus, Ruminococcus bromii, Ruminococcus callidus, Ruminococcus flavefaciens, Ruminococcus gnavus, Ruminococcus hansenii, Ruminococcus hydrogenotrophicus, Ruminococcus lactaris, Ruminococcus luti, Ruminococcus obeum, Ruminococcus palustris, Ruminococcus pasteurii, Ruminococcus productus, Ruminococcus schinkii, Ruminococcus torques, Sarcina maxima, Sarcina ventriculi, Clostridium absonum, Clostridium aceticum, Clostridium acetireducens, Clostridium acetobutylicum, Clostridium acidisoli, Clostridium acidurici, Clostridium aerotolerans, Clostridium akagii, Clostridium aldrichii, Clostridium algidicarnis, Clostridium algidixylanolyticum, Clostridium aminophilum, Clostridium aminovalericum, Clostridium amygdalinum, Clostridium arcticum, Clostridium argentinense, Clostridium aurantibutyricum, Clostridium baratii, Clostridium barkeri, Clostridium bartlettii, Clostridium beijerinckii, Clostridium bifermentans, Clostridium bolteae, Clostridium botulinum, Clostridium bowmanii, Clostridium bryantii, Clostridium butyricum, Clostridium cadaveris, Clostridium caminithermale, Clostridium carnis, Clostridium celatum, Clostridium celerecrescens, Clostridium cellobioparum, Clostridium cellulofermentans, Clostridium cellulolyticum, Clostridium cellulose, Clostridium cellulovorans, Clostridium chartatabidum, Clostridium chauvoei, Clostridium clostridioforme, Clostridium coccoides, Clostridium cochlearium, Clostridium cocleatum, Clostridium colicanis, Clostridium colinum, Clostridium collagenovorans, Clostridium cylindrosporum, Clostridium difficile, Clostridium dioli, Clostridium disporicum, Clostridium durum, Clostridium estertheticum, Clostridium estertheticum subsp. estertheticum, Clostridium estertheticum subsp. laramiense, Clostridium fallax, Clostridium felsineum, Clostridium fervidum, Clostridium fimetarium, Clostridium formicaceticum, Clostridium frigidicarnis, Clostridium frigoris, Clostridium gasigenes, Clostridium ghonii, Clostridium glycolicum, Clostridium grantii, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium hungatei, Clostridium hydroxybenzoicum, Clostridium hylemonae, Clostridium jejuense, Clostridium indolis, Clostridium innocuum, Clostridium intestinale, Clostridium irregulare, Clostridium isatidis, Clostridium josui, Clostiidium kluyveri, Clostridium lactatifermentans, Clostridium lacusfiyxellense, Clostridium laramiense, Clostridium lentocellum, Clostridium lentoputrescen, Clostridium leptum, Clostridium limosum, Clostridium litorale, Clostridium lituseburense, Clostridium ljungdahlii, Clostridium lortetii, Clostridium magnum, Clostridium malenominatum, Clostridium mangenotii, Clostridium mayombei, Clostridium methoxybenzovorans, Clostridium methylpentosum, Clostridium neopropionicum, Clostridium nexile, Clostridium novyi, Clostridium oceanicum, Clostridium orbiscindens, Clostridium oroticum, Clostridium oxalicum, Clostridium papyrosolvens, Clostridium paradoxum, Clostridium paraperfringens, Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polysaccharolyticum, Clostridium populeti, Clostridium propionicum, Clostridium proteoclasticum, Clostiidium proteolyticum, Clostridium psychrophilum, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostiidium saccharolyticum, Clostridium saccharoperbutylacetonicum, Clostridium sardiniense, Clostridium sartagoforme, Clostridium scatologenes, Clostridium scindens, Clostridium septicum, Clostridium sordellii, Clostridium sphenoides, Clostridium spiroforme, Clostridium sporogenes, Clostridium sporosphaeroides, Clostridium stercorarium, Clostridium stercorarium subsp. leptospartum, Clostridium stercorarium subsp. stercorarium, Clostridium stercorarium subsp. thermolacticum, Clostridium sticklandii, Clostridium straminisolvens, Clostridium subterminale, Clostridium symbiosum, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostiidium thermopalmarium, Clostridium thermopapyrolyticum, Clostridium thermosuccinogenes, Clostiidium thermosulfurigenes, Clostridium thiosulfatireducens, Clostridium tyrobutyricum, Clostridium uliginosum, Clostridium ultunense, Clostridium villosum, Clostridium vincentii, Clostridium viride, Clostridium xylanolyticum, Clostridium xylanovorans, Amoebobacter pediofromis, Amoebobacter pendens, Amoebobacter purpureus, Amoebobacter roseus, Chromatium buderi, Chromatium glycolicum, Chromatium gracile, Chromatium minus, Chromatium minutissimum, Chromatium okenii, Chromatium purpuratum, Chromatium salexigens, Chromatium tepidum, Chromatium vinosum, Chromatium violascens, Chromatium warmingii, Chromatium weissei, Lamprobacter modestohalophilus, Lamprocystis purpurea, Lamprocystis roseopersicina, Thiocapsa halophila, Thiocapsa litoralis, Thiocapsa marina, Thiocapsa penden, Thiocapsa rosea, Thiocapsa roseopersicina, Thiocystis gelatinosa, Thiocystis minor, Thiocystis violacea, Thiocystis violascens, Thiodictyon bacillosum, Thiodictyon elegans, Thiopedia rosea, Thiospirillum jenense, Ectothiorhodospira abdelmalekii, Ectothiorhodospira haloalkaliphila, Ectothiorhodospira halochloris, Ectothiorhodospira halophila, Ectothiorhodospira marina, Ectothiorhodospira marismortui, Ectothiorhodospira mobilis, Ectothiorhodospira shaposhnikovii, Ectothiorhodospira vacuolata, Rhodobacter adriaticus, Rhodobacter azotoformans, Rhodobacter blasticus, Rhodobacter capsulatus, Rhodobacter euryhalinus, Rhodobacter sphaeroides, Rhodobacter sidfidophilus, Rhodobacter veldkampii, Rhodocyclus gelatinosus, Rhodocyclus purpureus, Rhodocyclus tenuis, Rhodomicrobium vannielii, Rhodopila globiformis, Rhodopseudomonas acidophila, Rhodopseudomonas adriatica, Rhodopseudomonas blastica, Rhodopseudomonas capsulata, Rhodopseudomonas faecalis, Rhodopseudomonas gelatinosa, Rhodopseudomonas globiformis, Rhodopseudomonas Julia, Rhodopseudomonas marina, Rhodopseudomonas palustris, Rhodopseudomonas rhenobacensis, Rhodopseudomonas rosea, Rhodopseudomonas rutila, Rhodopseudomonas sphaeroides, Rhodopseudomonas sulfidophila, Rhodopseudomonas sulfoviridis, Rhodopseudomonas viridis, Rhodospirillum centenum, Rhodospirillum fulvum, Rhodospirillum molischianum, Rhodospirillum photometricum, Rhodospirillum rubrum, Rhodospirillum salexigens, Rhodospirillum salinarum, Rhodospirillum sodomense, Rhodospirillum tenue, Erythrobacter aquimaris, Erythrobacter citreus, Erythrobacter flavus, Erythrobacter gaetbuli, Erythrobacter litoralis, Erythrobacter longus, Erythrobacter seohaensis, Methanobacterium aarhusense, Methanobacterium alcaliphilum, Methanobacterium arbophilicum, Methanobacterium beijingense, Methanebacterium bryantii, Methanobacterium congolense, Methanobacterium defluvii, Methanobacterium espanolae, Methanobacterium formicicum, Methanobacterium ivanovii, Methanobacterium mobile, Methanobacterium oryzae, Methanobacterium ruminantium, Methanobacterium subterraneum, Methanobacterium thermaggregans, Methanobacterium thermalcaliphilum, Methanobacterium thermautotrophicum, Methanobacterium thermoflexum, Methanobacterium thermoformicicum, Methanobacterium thermophilum, Methanobacterium uliginosum, Methanobacterium wolfei, Methanobrevibacter acididurans, Methanobrevibacter arboriphilus, Methanobrevibacter curvatus, Methanobrevibacter cuticularis, Methanobrevibacter filiformis, Methanobrevibacter gottschalkii, Methanobrevibacter oralis, Methanobrevibacter ruminantium, Methanobrevibacter smithii, Methanobrevibacter thaueri, Methanobrevibacter woesei, Methanobrevibacter wolinii, Methanococcus delta, Methanococcus fervens, Methanococcus frisius, Methanococcus halophilus, Methanococcus igneus, Methanococcus infernus, Methanococcus jannaschii, Methanococcus maripaludis, Methanococcus mazei, Methanococcus thermolithotrophicus, Methanococcus vannielii, Methanococcus voltae, Methanococcus vulcanius, Methanococcoides burtonii, Methanococcoides methylutens, Methanolobus bombayensis, Methanolobus oregonensis, Methanolobus siciliae, Methanolobus taylorii, Methanolobus tindarius, Methanolobus vulcani, Methanolacinia paynteri, Methanomicrobium mobile, Methanomicrobium paynteri, Methanogenium aggregans, Methanogenium bourgense, Meihanogenium cariaci, Methanogenium frigidum, Methanogenium frittonii, Methanogenium liminatans, Methanogenium marinum, Methanogenium marisnigri, Methanogenium olentangyi, Methanogenium organophilum, Methanogenium tationis, Methanogenium thermophilicum, Methanospirillum hungatei, Methanoplanus endosymbiosus, Methanoplanus limicola, Methanoplanus petrolearius, Methanothrix concilii, Methanothrix soehngenii, Methanothrix thermoacetophila, Methanothrix thermophila, Methanothermus fervidus, Methanothermus sociabilis, Methanocorpusculum aggregans, Methanocorpusculum bavaricum, Methanocorpusculum labreanum, Methanocorpusculum parvum, Methanocorpusculum sinense, Methanoculleus bourgensis, Methanoculleus chikugoensis, Methanoculleus marisnigri, Methanoculleus oldenburgensis, Methanoculleus olentangyi, Methanoculleus palmolei, Methanoculleus submarinus, Methanoculleus thermophilus, Methanohalobium evestigatum, Methanohalophilus halophilus, Methanohalophilus mahii, Methanohalophilus oregonensis, Methanohalophilus portucalensis, Methanohalophilus zhilinae, Methanosarcina acetivorans, Methanosarcina baltica, Methanosarcina barkeri, Methanosarcina frisia, Methanosarcina lacustris, Methanosarcina methanica, Methanosarcina semesia,

*Methanosarcina siciliae, Methanosarcina thermophila, Methanosarcina vacuolata, Methanosphaera cuniculi, Methanosphaera stadtmanae, Eubacterium acidaminophilum, Eubacterium aerofaciens, Eubacterium aggregans, Eubacterium alactolyticum, Eubacterium angustum, Eubacterium barkeri, Eubacterium biforme, Eubacterium brachy, Eubacterium budayi, Eubacterium callanderi, Eubacterium cellulosolvens, Eubacterium combesii, Eubacterium contortum, Eubacterium coprostanoligenes, Eubacterium cylindroids, Eubacterium desmolans, Eubacterium dolichum, Eubacterium eligens, Eubacterium exiguum, Eubacterium fissicatena, Eubacterium formicigenerans, Eubacterium fossor, Eubacterium hadrum, Eubacterium hallii, Eubacterium infinnum, Eubacterium lentum, Eubacterium limosum, Eubacterium minutum, Eubacterium moniliforme, Eubacterium multiforme, Eubacterium nitritogenes, Eubacterium nodatum, Eubacterium oxidoreducens, Eubacterium plautii, Eubacterium plexicaudatum, Eubacterium pyruvativorans, Eubacterium ramulus, Eubacterium rectale, Eubacterium ruminantium, Eubacterium saburreum, Eubacterium saphenum, Eubacterium siraeum, Eubacterium suis, Eubacterium sulci, Eubacterium tarantellae, Eubacterium tardum, Eubacterium tenue, Eubacterium timidum, Eubacterium tortuosum, Eubacterium uniforme, Eubacterium ventriosum, Eubacterium xylanophilum, Eubacterium yurii, Eubacterium yurii* subsp. *margaretiae, Eubacterium yurii* subsp. *schtitka, Eubacterium yurii* subsp. *Yurii, Abiotrophia adiacens, Abiotrophia balaetiopterae, Abiotrophia defectiva, Abiotrophia elegans, Atopobium fossor, Atopobium minutum, Atopobium parvulum, Atopobium rimae, Atopobium vaginae, Gemella bergeri, Gemella cuniculi, Gemella haemolysans, Gemella morbillorum, Gemella palaticanis, Gemella sanguinis, Granulicatella adiacens, Granulicatella balaenopterae, Granulicatella elegans, Finegoldia magna, Lactobacillus acetotolerans, Lactobacillus acidifarinae, Lactobacillus acidipiscis, Lactobacillus acidophilus, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus antri, Lactobacillus arizonensis, Lactobacillus aviarius, Lactobacillus aviarius* subsp. *Arqffinosus, Lactobacillus aviarius* subsp. *Aviarius, Lactobacillus bavaricus, Lactobacillus bifermentans, Lactobacillus brevis, Lactobacillus buchneri, Lactobacillus bulgaricus, Lactobacillus carnis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus cellobiosus, Lactobacillus coleohominis, Lactobacillus collinoide, Lactobacillus confuses, Lactobacillus coryniformis, Lactobacillus coiyniformis* subsp. *coryniformis, Lactobacillus coryniformis* subsp. *torquens, Lactobacillus crispatus, Lactobacillus curvatus, Lactobacillus curvatus* subsp. *curvatus, Lactobacillus curvatus* subsp. *melibiosus, Lactobacillus cypricasei, Lactobacillus delbrueckii, Lactobacillus delbrueckii* subsp. *bulgaricus, Lactobacillus delbrueckii* subsp. *delbrueckii, Lactobacillus delbrueckii* subsp. *indicus, Lactobacillus delbrueckii* subsp. *lactis, Lactobacillus dioliovrans, Lactobacillus divergens, Lactobacillus durianis, Lactobacillus equi, Lactobacillus farciminis, Lactobacillus ferintoshensis, Lactobacillus fermentuni, Lactobacillus formicalis, Lactobacillus fructivorans, Lactobacillus fructosus, Lactobacillus frumenti, Lactobacillus fuchuensis, Lactobacillus gallinarum, Lactobacillus gasseri, Lactobacillus gastricus, Lactobacillus gramini, Lactobacillus halotolerans, Lactobacillus hammesii, Lactobacillus hamsteri, Lactobacillus helveticus, Lactobacillus heterohiochii, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kandleri, Lactobacillus kefuranofaciens, Lactobacillus kefuranofaciens* subsp. *kefuranofaciens, Lactobacillus kefuranofaciens* subsp. *kefirgranum, Lactobacillus kefirgranum, Lactobacillus kefir, Lactobacillus kimchii, Lactobacillus kitasatonis, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus mindensis, Lactobacillus minor, Lactobacillus mucosae, Lactobacillus murinus, Lactobacillus nagelii, Lactobacillus oris, Lactobacillus panis, Lactobacillus pantheris, Lactobacillus parabuchneri, Lactobacillus paracasei, Lactobacillus paracasei* subsp. *paracasei, Lactobacillus paracasei* subsp. *tolerans, Lactobacillus paracollinoides, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus psittaci, Lactobacillus reuteri, Lactobacillus rhamnosus, Lactobacillus rimae, Lactobacillus rogosae, Lactobacillus rossii, Lactobacillus ruminis, Lactobacillus saerimneri, Lactobacillus sakei, Lactobacillus sakei* subsp. *carnosus, Lactobacillus sakei* subsp. *sakei, Lactobacillus salivarius, Lactobacillus salivarius* subsp. *salicinius, Lactobacillus salivarius* subsp. *salivarius, Lactobacillus sanfranciscensis, Lactobacillus satsumensis, Lactobacillus sharpeae, Lactobacillus spicheri, Lactobacillus suebicus, Lactobacillus suntoryeus, Lactobacillus thermotolerans, Lactobacillus trichodes, Lactobacillus uli, Lactobacillus ultunensis, Lactobacillus vaccinostercus, Lactobacillus vaginalis, Lactobacillus versmoldensis, Lactobacillus viridescens, Lactobacillus vitulinu, Lactobacillus xylosus, Lactobacillus yamanashiensis, Lactobacillus yamanashiensis* subsp. *mali, Lactobacillus yamanashiensis* subsp. *yamanashiensis, Lactobacillus zeae, Lactobacillus zymae, Actinomyces bernardiae, Actinomyces bovis, Actinomyces bowdenii, Actinomyces canis, Actinomyces cardiffensis, Actinomyces catuli, Actinomyces coleocanis, Actinomyces dentalis, Actinomyces denticolens, Actinomyces europaeus, Actinomyces funkei, Actinomyces Georgia, Actinomyces gerencseriae, Actinomyces graevenitzii, Actinomyces hongkongensis, Actinomyces hordeovulneris, Actinomyces howellii, Actinomyces humiferus, Actinomyces hyovaginalis, Actinomyces israelii, Actinomyces marimammalium, Actinomyces meyeri, Actinomyces naeslundii, Actinomyces nasicola, Actinomyces neuii, Actinomyces neuii* subsp. *anitratus, Actinomyces neuii* subsp. *neuii, Actinomyces odontolyticus, Actinomyces oricola, Actinomyces pyogenes, Actinomyces pyogenes, Actinomyces radicidentis, Actinomyces radingae, Actinomyces slackii, Actinomyces suimastitidis, Actinomyces suis, Actinomyces turicensis, Actinomyces urogenitalis, Actinomyces vaccimaxillae, Actinomyces viscosus, Arcanobacterium bernardiae, Arcanobacterium haemolyticum, Arcanobacterium hippocoleae, Arcanobacterium phocae, Arcanobacterium pluranimalium, Arcanobacterium pyogenes, Actinobaculum schaalii, Actinobaculum suis, Actinobaculum urinale, Bulleidia extructa, Collinsella aerofaciens, Collinsella intestinalis, Collinsella stercoris, Cryptobacterium curtum, Holdemania filiformis, Rothia aeria, Rothia amarae, Rothia dentocariosa, Rothia mucilaginosa, Rothia nasimurium, Pseudoramibacter alactolyticus, Mogibacterium diversum, Mogibacterium neglectum, Mogibacterium pumilum, Mogibacterium timidum, Mogibacterium vescum,*

*Slackia exigua*, *Slackia heliotrinireducens*, and *Eggerthella lenta* (hereinafter referred to as "anaerobic bacteria" or a similar term).

In further or alternative embodiments of all aspects using substantially purified anaerobic bacterial strains, the bacteria may be collected from bovine rumen, soil samples, sludge, anaerobic bacteria cultures, aerobic bacteria cultures, anaerobic sediments from fresh or brackish waters, sewage, animals, animal feces, insect digestive tract, dental samples, hydrothermal soils, hydrothermal pools and deep water hydrothermal vents.

In further or alternative embodiments of all aspects using substantially purified anaerobic bacterial strains, the bacteria may be obtained by genetic modification of known bactial strains. In further or alternative embodiments of all aspects using substantially purified anaerobic bacterial strains, the genetic modification results from transformation procedures, bacterial conjugation, transduction, interaction of bacterial strains with mutagens, and combinations thereof. In further or alternative embodiments, the mutagens include, but not limited to, chemicals, ultraviolet light, and radioactive elements.

In further or alternative embodiments of all aspects using substantially purified anaerobic bacteria cultures, the substantially purified anaerobic bacteria cultures incorporate, along with appropriate growth media, substantially purified single bacterial strains. In further or alternative embodiments of all aspects utilizing substantially purified anaerobic bacterial strains, the substantially purified anaerobic bacterial strains are part of inoculants. In further or alternative embodiments of all aspects using substantially purified anaerobic bacterial strains, the substantially purified single bacterial strains are at least 95% purified. In still further or alternative embodiments of all aspects using substantially purified anaerobic bacterial strains, the substantially purified single bacterial strains are at least 99% purified. In even further or alternative embodiments of all aspects using substantially purified anaerobic bacterial strains, the substantially purified single bacterial strains are at least 99.5% purified.

Biomass

In further or alternative embodiments of all aspects using biomass, the biomass comprises material obtained from energy crops, surplus agricultural products, waste from sugar production and processing facilities, animal waste from zoos, waste from fruit processing industries, waste from pulp and paper mills, silvaculture residues, waste from wood processing, waste from agricultural product processing, food waste, solids isolated from fermentation cultures, municipal sewer waste, animal manure, animal urine, animal parts, fish parts, and combinations thereof. In further or alternative embodiments of all aspects utilizing a biomass, the biomass may be material such as, but not limited to, glucose, beet sugar, sugar beet molasses, sugar beet syrup, sugar beet juice, sugar cane molasses, cane sugar, sugar cane syrup, sugar cane juice, corn syrup, cereal grains, oat flour, rice flour, corn flour, wheat flour, potatoes, tomatoes, potato juice, tomato pulp, tomato juice, potato pulp, cheese whey, sorghum, corn mash, wheat mash, oat mash, blackstrap molasses, citrus molasses, invert sugar, sucrose, fructose, glucose, wood sugar, cellulose, xylose, plant parts, fruit, vegetable, bovine manure, poultry manure, equine manure, porcine manure, bovine urine, poultry urine, equine urine, porcine urine, wood shavings, wood chips, shredded paper, cotton burrs, grain, chaff, seed shells, hay, alfalfa, grass, leaves, seed pods, corn shucks, weeds, aquatic plants, algae, fungus, and combinations thereof.

In further or alternative embodiments of all aspects, the processes of anaerobically fermenting biomass are continuous processes. In still further or alternative embodiments of all aspects, the processes of anaerobically fermenting biomass are batch processes.

Chemical Products and Uses of Chemical Products

In further or alternative embodiments of all aspects in which chemical products are produced by anaerobically fermenting biomass, the chemical products may be gaseous, non-gaseous, or combinations thereof. In further or alternative embodiments of such aspects, the non gaseous chemical products may be solids, solvents, volatile organic acids, salts of volatile organic acids, or combinations thereof. In further or alternative embodiments of such aspects, the gaseous chemical products may be hydrogen, carbon dioxide, carbon monoxide, methane, hydrogen sulfide, ammonia, nitrogen, and combinations thereof. In further or alternative embodiments of such aspects, the gaseous chemical products may be hydrogen, carbon dioxide, carbon monoxide, hydrogen sulfide, ammonia, nitrogen, and combinations thereof. In further or alternative embodiments of all aspects, the solid chemical products may be solids which comprises sulfur, and in further or alternative embodiments of such aspects, the solid chemical products may be elemental sulfur. In still further or alternative embodiments of such aspects, the chemical products may be solvents, such as, but not limited to, acetone, butanol, propanol, isopropanol, 1,2-propanediol, ethanol, methanol, and combinations thereof. In further or alternative embodiments of such aspects, the chemical products are volatile organic acids, such as, but not limited to formic acid, acetic acid, propionic acid, butyric acid, valeric acid, and combinations thereof. In further or alternative embodiments of such aspects, the chemical products are salts of volatile organic acids in which the anion include, but are not limited to, formate, acetate, propionate, butyrate, valerate, and combinations thereof. In further or alternative embodiments of such aspects, the chemical products are salts of the volatile organic acids the cations may alkali metal ions, alkaline earth ions, ammonium ion, or combinations thereof. In still further or alternative embodiments of such aspects, cations of the salts of volatile organic acids may be $Na^+$, $K^+$, $Ca^{2+}$, $Mg^{2+}$, $NH_4^+$, and combinations thereof.

In one aspect are compositions which include at least one chemical product produced by anaerobically fermenting biomass using substantially purified anaerobic bacteria cultures. In an embodiment of this aspect, the substantially purified anaerobic bacteria cultures have not been subjected to heat-shocking processes, and in further or alternative embodiments, the substantially purified anaerobic bacteria cultures are used as inoculants in anaerobic fermentation apparatuses.

In another aspect are feedstocks for chemical industries which are chemical products produced by anaerobically fermenting biomass. In an embodiment of this aspect, the chemical industries utilizing such feedstocks include polymer industries, industrial synthesis industries, photographic industries, coatings industries, fertilizer industries, printing industries, and combinations thereof.

In another aspect are energy sources for a power generation systems which are gaseous chemical products and solvents produced by anaerobically fermenting biomass. In an embodiment of this aspect, the power generation systems may be fuel cells, internal combustion generators, turbine generators, Stirling engines, and combinations thereof. In further or alternative embodiments, the power generation systems are part of power stations. In further or alternative embodiments, the power stations are decentralized power stations. In further or alternative embodiments, the fuel cells may be alkaline fuel cells, phosphoric acid fuel cells, molten carbonate fuel cells, solid oxide fuel cells, proton exchange membrane fuel cells, and combinations thereof. In further or alternative embodiments, the fuel cells are used to generate electricity for residential consumption, commercial consumption, motor vehicle consumption, or combinations thereof. In still further or alternative embodiments, the electricity generated by such fuel cells may be used locally, added to the grid, or combinations thereof. In further or alternative embodiments, the turbine generators are used to generate electricity from steam created by heating water, wherein the heat is generated by combustion of compositions comprising chemical products produced by anaerobically fermenting biomass. In further or alternative embodiments, the electricity generated by such turbines may be used for residential consumption or commercial consumption. In still further or alternative embodiments, the electricity generated by such turbines may be used locally, added to the grid, or combinations thereof.

In another aspect are compositions which contain chemical products formed by admixing carbon oxides, catalysts, and hydrogen, in which the hydrogen has been produce by anaerobically fermenting biomass using substantially purified anaerobic bacteria cultures. In an embodiment of this aspect, the substantially purified anaerobic bacteria cultures have not been subjected to heatshocking processes. In further or alternative embodiments, the chemical product is methane. In further or alternative embodiments, the carbon oxide may be carbon monoxide, carbon dioxide, or combination thereof. In further or alternative embodiments, the catalysts contain activated nickel, and in still further or alternative embodiments the catalyst is NiO/MgO. In further or alternative embodiments, are energy sources for a power generation systems which contain such chemical products. In still further or alternative embodiments, the chemical product of such energy sources is methane. In further or alternative embodiments, the power generation system may be fuel cells, internal combustion generators, turbine generators, and combinations thereof. In further or alternative embodiments, the power generation systems are part of power stations. In further or alternative embodiments, the power stations are decentralized power stations. In further or alternative embodiments, the fuel cells may molten carbonate fuel cells, solid oxide fuel cells, and combinations thereof. In further or alternative embodiments, the fuel cells are used to generate electricity for residential consumption, commercial consumption, motor-vehicle consumption, or combinations thereof. In still further or alternative embodiments, the electricity generated by such fuel cells may be used locally, added to the grid, or combinations thereof. In further or alternative embodiments, the turbine generators are used to generate electricity from steam created by heating water, wherein the heat is generated by combustion of such compositions comprising chemical products produced by anaerobically fermenting biomass. In further or alternative embodiments, the electricity generated by such turbines may be used for residential consumption or commercial consumption. In still further or alternative embodiments, the electricity generated by such turbines may be used locally, added to the grid, or combinations thereof. In further or alternative embodiments, the chemical product may be used as an energy source for heat generation systems. In still further or alternative embodiments, the heat generation systems may be furnaces, stovetops, ovens, barbeques, and driers. In still further or alternative embodiments, such an energy source may be a replacement for, or a compliment to, natural gas and methane.

In another aspect are compositions which contain chemical products formed by hydrogenation of starting materials using hydrogen and catalysts, wherein the hydrogen is produced by anaerobically fermenting a biomass using substantially purified anaerobic bacteria cultures. Hydrogenation occurs by admixing starting materials and catalysts, with hydrogen. In an embodiment of this aspect, the substantially purified anaerobic bacteria cultures have not been subjected to heatshocking processes. In further or alternative embodiments, the chemical product is aniline and the starting material is nitrobenzene. In further or alternative embodiments, the catalysts may be NiS/CuS catalysts or Cu catalysts. In further or alternative embodiments, the aniline may be used in the synthesis of pharmaceuticals, polymers, dyes, or solvents.

In another aspect are compositions which contain chemical products formed by admixing minerals and volatile organic acids, wherein the volatile organic acids are produced by anaerobically fermenting a biomass using substantially purified anaerobic bacteria cultures. In an embodiment of this aspect, the substantially purified anaerobic bacteria cultures have not been subjected to heatshocking processes. In further or alternative embodiments, the volatile organic acid is acetic acid. In further or alternative embodiments, the mineral is dolomite and the chemical product is calcium magnesium acetate. In further or alternative embodiments, the calcium magnesium acetate may be used as/in anti-freeze agents, deicing agents, or anti-icing agents.

In another aspect are compositions which contain chemical products formed by admixing oxides, liquid ammonia and volatile organic acids, wherein the volatile organic acids are produced by anaerobically fermenting biomass using substantially purified anaerobic bacteria cultures. In an embodiment of this aspect, the substantially purified anaerobic bacteria cultures have not been subjected to heatshocking processes. In further or alternative embodiments, the volatile organic acid is acetic acid. In further or alternative embodiments, the oxide is zinc oxide and the chemical product is zinc ammonium acetate. In further or alternative embodiments, the calcium magnesium acetate may be used as/in fertilizer or seed germination enhancers.

Anaerobic Fermentation Apparatuses

In one aspect are anaerobic fermentation apparatuses which use populations of substantially purified anaerobic bacterial strains for anaerobically fermenting biomass into chemical products. The aforementioned anaerobic fermentation apparatuses include (a) sterilization and deoxygenation systems, (b) anaerobic digesters, each of which contains a population of substantially purified anaerobic bacteria and are equipped with anaerobic digester control systems, (c) plurality of pipelines and pumps for introducing and re-circulating biomass, and (d) removal pipelines connected to the anaerobic digesters for removing chemical products from the anaerobic digesters. In addition to this aspect, the population of substantially purified anaerobic bacterial strain has not been subjected to a heatshocking process.

In an embodiment of the aforementioned aspect, the anaerobic fermentation apparatuses further include pipelines in communication with the sterilization and deoxygenation systems having pumps which are used for transferring sterilized and deoxygenated biomass to concentrating systems. In further or alternative embodiments, the anaerobic fermentation apparatuses also incorporate pipelines in communication with concentrating systems and have pumps for transferring deoxygenated, concentrated, sterilized, detoxified, and/or pre-digested biomass to at least one anaerobic digester.

In further or alternative embodiments, the anaerobic fermentation apparatuses may incorporate anaerobic digesters, each of which may contain a population of substantially purified anaerobic photo-fermentation bacteria and are equipped with anaerobic digester control systems. In further or alternative embodiments, the anaerobic fermentation apparatuses may incorporate anaerobic digesters, each of which may contain a population of substantially purified anaerobic acetogenic bacteria and are equipped with anaerobic digester control systems. In further or alternative embodiments, the anaerobic fermentation apparatuses may incorporate anaerobic digesters, each of which contain may a population of substantially purified anaerobic solventogenic bacteria and are equipped with anaerobic digester control systems. In still further or alternative embodiments, the anaerobic fermentation apparatuses may incorporate anaerobic digesters, each of which may contain a population of substantially purified anaerobic proteolytic bacteria and are equipped with anaerobic digester control systems.

In further or alternative embodiments, the anaerobic fermentation apparatuses may be stand alone systems for anaerobically fermenting biomass into chemical products, or in still further or alternative embodiments, the anaerobic fermentation apparatuses may be components of assemblages for generating power.

In further or alternative embodiments, the sterilization and deoxygenation systems of the anaerobic fermentation apparatuses are used to sterilize and deoxygenate biomass by means of steam treatment processes, wherein the steam treatment processes may be pressurized steam treatment processes which use low pressure steam or high pressure steam. In further or alternative embodiments, the sterilization and deoxygenation systems are steam heat exchanger systems. In still further or alternative embodiments, the sterilization and deoxygenation systems are autoclaves.

In further or alternative embodiments, the sterilization and deoxygenation systems of the anaerobic fermentation apparatuses are assemblages which incorporate at least one vat, at least one source of steam, and at least one turbine. The sources of steam may be sources of high pressure steam, which include, but are not limited to, boilers. In further or alternative embodiments, the turbines of the sterilization and deoxygenation systems may be used to produce low pressure steam and to generate electricity, and in still further or alternative embodiments, such turbines include, but are not limited to, backpressure turbine generators which generate low pressure steam to sterilize and deoxygenate biomass and produce electricity as power for local energy consumer, or for addition to grid systems of centralized power stations. Such local energy consumer may include, but are not limited to, facilities for anaerobic fermentation, factories, buildings, facilities for processing farm produce, and combinations therein.

In further or alternative embodiments, the concentrating systems of the anaerobic fermentation apparatuses are centrifugation systems used to concentrate biomass by means of centrifugation processes. In further or alternative embodiments, the concentrating systems are reverse osmosis systems used to concentrate biomass by means of reverse osmosis processes.

In further or alternative embodiments, the removal pipelines connected to anaerobic digesters have at least one output pipeline for gaseous chemical products and at least one output pipeline for non-gaseous chemical products. In further or alternative embodiments, gaseous chemical products may be removed from anaerobic digesters using at least one output pipeline, and in still further or alternative embodiments, gaseous chemical products are removed from anaerobic digesters by means of a vacuum applied to at least one output pipeline. In further or alternative embodiments, gas scrubbers are connected to at least one output pipeline and gas compressors are connected to the scrubbers, and at least one gas storage tank. In further or alternative embodiments, non-gaseous chemical products may be removed from anaerobic digesters using at least one output pipeline, and in further or alternative embodiments, the non-gaseous chemical products are volatile organic acids which are removed from output pipelines by reverse osmosis systems which are coupled to the output pipelines and to at least one storage tank. Similarly, in further or alternative embodiments, the non-gaseous chemical product may be salts of volatile organic acids which may be removed from output pipelines by reverse osmosis systems which are coupled to output pipelines and at least one storage tank. In still further or alternative embodiments, the solid non-gaseous chemical products may be removed from output pipelines by filtration systems which are coupled to the output pipeline and to at least one storage tank. In addition, in further or alternative embodiments the solid chemical product is elemental sulfur which may be removed from output pipelines by filtration systems which are coupled to the output pipelines and at least one storage tank. In further or alternative embodiments, such filtration systems are cross-flow filtration systems. In still further or alternative embodiments, the non-gaseous chemical products may be solvents which are removed from the output pipelines by osmosis systems which are coupled to the output pipelines and to at least one storage tank.

In further or alternative embodiments, the gaseous chemical products which have been removed from the anaerobic digester via output pipelines may be isolated and purified by means of a differential compression process. In further or alternative embodiments, the volatile organic acids which have been removed from the anaerobic digester via output pipelines may be isolated and purified using distillation. In still further or alternative embodiments, the solvents which have been removed from the anaerobic digester via output pipelines may be isolated and purified using distillation. In further or alternative embodiments, the salts of volatile organic acids which have been removed from the anaerobic digester via output pipelines may be isolated and purified by reverse osmosis.

In further or alternative embodiments, anaerobic digester control systems combine at process control tools, metrology tools to acquire metrology data relating to anaerobic fermentation parameters; and process controllers operatively coupled to the process control tools and the metrology data, wherein the process controllers consists of decision making units, input/output boards, and database units to store the metrology data. Such anaerobic digester control systems may be used to optimally operate anaerobic digesters.

In further or alternative embodiments, process control tools are used to adjust operating parameters of the anaerobic digester, wherein the operating parameters are related to anaerobic fermentation parameters. In further or alternative embodiments, such process control tools are valves or any means for adjusting the temperature of the digester.

In further or alternative embodiments, the decision making units are used in feedback control processes to acquire metrology data from the input/output boards, then determine control adjustments to maintain anaerobic fermentation parameters within defined operational ranges, then modify the magnitude of the control adjustments, and return the modified control adjustments to the input/output boards, whereby by the modified control adjustments are sent to process control tools to adjust operating parameters, which are related to anaerobic fermentation parameters of the anaerobic fermentation digester. In further or alternative embodiments, the feedback control processes are continuous, automatic feedback control loops, while in still further or alternative embodiments, the feedback control processes are intermittent, manual feedback control loops. In still further or alternative embodiments, the process controller decision making units may be computers, PROMs, EPROMs, EEPROMs, and combinations thereof.

In further or alternative embodiments, the anaerobic fermentation parameters may be temperature, pH, pressure, gas flow, biomass concentration, and chemical products concentration, wherein the metrology tool used to monitor such parameters may be pH sensors, stirrers, oxidation-reduction monitors, nutrient concentration, pressure sensors, gas flow sensors, gas sensors, temperature sensors, gas chromatographic systems, flow injection analysis systems, High Performance Liquid Chromatographic systems, Mass specrophotometry, and combinations thereof. In further or alternative embodiments, the pH sensors are selected from glass membrane pH electrodes, solid state pH electrodes, optode pH sensors, and combinations thereof. In further or alternative embodiments, the temperature sensors selected from thermometers, thermopiles, thermocouples, and combinations thereof. In further or alternative embodiments, the metrology tools may be located on-line, or in further or alternative embodiments, the metrology tools may be located in-line.

In further or alternative embodiments, the anaerobic fermentation apparatuses may be incorporated into centralized power generation facilities, and in still further or alternative embodiments, the anaerobic fermentation apparatuses may be incorporated into decentralized power generation facilities.

In another aspect are assemblages combining sources of steam, turbines, and digesters. In an embodiment of this aspect, the sources of steam may be sources of high pressure steam. In further or alternative embodiments, the sources of high pressure steam may be boilers. In still further or alternative embodiments, the sources of high pressure steam are boilers heated by combustion of hydrogen, wherein the hydrogen has been produced by anaerobically fermenting biomass. In further or alternative embodiments, the digester may be at least one anaerobic digester. In further or alternative embodiments, the turbines of the assemblages may be used to produce low pressure steam and to generate electricity. In further or alternative embodiments, the low pressure steam produced by such turbines may be used for biomass sterilization and deoxygenation. In still further or alternative embodiments, the electricity generated by such turbines may be used as power for local energy consumers or for addition to grid systems of centralized power stations. In even further or alternative embodiments, the local energy consumers may be facilities for anaerobic fermentation, factories, buildings, homes, facilities for processing farm produce, and combinations thereof.

Knowledge Management System

In another aspect are methods for identifying bacterial species for use in the anaerobic production of hydrogen from a particular biomass. The methods involve collecting appropriate information from various bacterial species and deriving probabilistic models from the information, the probabilistic models being indicative of identification of bacterial species for use in the anaerobic production of hydrogen and other chemical products from particular biomass. In an embodiment of this aspect, the identification of bacterial species for use in the anaerobic production of hydrogen and other chemical products from particular biomass includes use of cultivation systems to identify various bacterial species and collecting appropriate information from the cultivation system. In further or alternative embodiments, the cultivation systems includes growing various bacterial species on particular substrates, under various growth conditions to optimize the bacterial hydrogen production. In further or alternative embodiments, the various growth conditions are selected from the group consisting of variation in temperature, pH, fermentation products, exposure to various natural gases or compounds, antibiotic efficacy, antibiotic resistance, compound stimulation-digestion, compound toxicity or survivability. In further or alternative embodiments, the collection of appropriate information comprises selecting response data from the scientific literature. In further or alternative embodiments, the appropriate information comprises characteristics, wherein such characteristics are bacteria growth on various substrates, bacteria sensitivity to various conditions and/or bacteria production of various metabolites. In still further or alternative embodiments, such characteristics are categorized into traits which include, but are not limited to, acetic acid major metabolic product, acetic acid minor metabolic product, acetone, ADH, ALP, alpha-fucosidase, alpha-galactosidase, ammonia production, alpha-glucosidase, arabinose, ArgA, *bacillus*, beta-galactosidase, beta-glucosidase, beta-glucuronidase, beta-NAG, beta-xylosidase, box car shape, butyric acid major metabolic product, butyric acid minor metabolic product, Butanol, CAMP, caproic acid major metabolic product, carbon dioxide production, catalase, cellobiose, cellulose, chartreuse fluorescence, chymotrypsin, $CO_2$ growth, coccus, desulfoviridin, double zone beta-hemolysis, esculin hydrolysis, ethanol production, F/F required, fructose, gelatin hydrolysis, glucose, glycogen, gram reaction, growth in bile, HisA, hydrogen production, hydrogen sulfide production, 1-arabinose, indole, isobutyric acid major metabolic product, isobutyric acid minor metabolic product, isocapronic acid major metabolic product, isocapronic acid minor metabolic product, isovaleric acid major metabolic product, isovaleric acid minor metabolic product, lactate converted to propionate, lactic acid major metabolic product, lactic acid minor metabolic product, lactose, leithinase, LeuA, lipase, maltose, mannitol, mannose, melezitose, melibiose, methane production, milk clot formed, milk digested, motile, N-Acetyl-beta-glucosaminidase, nitrate, ONPG(Beta-galactosidase), oxygen tolerance, PheA, phenylacetic acid minor metabolic product, pigment, pitting of agar, ProA, propionic acid major metabolic product, PyrA, raffinose, red fluorescence, reverse CAMP test, rhamnose, ribose, salicin, sensitive to colistin, sensitive to kanamycin, sensitive to SPS, sensitive to vancomycin, sorbitol, spore former, starch hydrolysis, strictly anaerobic, subterminal spore location, succinic acid major metabolic product, succinic acid minor metabolic product, sucrose, terminal spore location, threonine converted to propionate, trehalose, trypsin, TyrA, urease, valeric acid major metabolic product, valeric acid minor metabolic product, xylan, and xylose. Such categorization in the case of information regarding bacteria growth on various substrates may allow identification of bacteria strains which utilize specific substances as food sources, or it may allow the identification of optimal food sources for specific bacterial strains. In addition, categorization of the information regarding bacteria sensitivity to various conditions may allow for identification of optimal conditions for the anaerobic fermentation of various substances, while categorization of the information regarding bacteria production of various metabolites may allow for identification the metabolites produced by various bacterial strains using various food sources.

In further or alternative embodiments, the appropriate information may be bacterial response which may be positive, negative, a variable response, or non responsive. In still further or alternative embodiments, the bacterial response is measured by smell, color, growth, non-growth, death, symbiosis, inhibition, and non-symbiosis. In further or alternative embodiments, the appropriate information is collected in computer readable media. In further or alternative embodiments, the probabilistic models are derived using minimizing parameters based on the appropriate information.

In another aspect are program products for use in computers that executes program instructions recorded in a computer-readable media to produce candidate bacterial species for use in the anaerobic production of hydrogen and other chemical products from particular biomass, the program products comprising recordable media and a plurality of computer-readable program instructions on the recordable media that are executable by the computer to perform a method comprising receiving a plurality of bacterial species, where relationships between species are defined, receiving a plurality of appropriate information for the plurality of bacteria species, and generating the candidate bacterial species for use in the anaerobic production of hydrogen from a particular biomass by traversing the plurality of information received hi order to find the optimal match.

In further or alternative embodiments, the program products may collect appropriate information by conducting cultivation systems to identify various bacterial species or by selecting response data from the scientific literature. In further or alternative embodiments, the program product may have cultivation systems comprises growing various bacterial species on particular substrates, under various growth conditions to optimize the bacterial hydrogen production. In further or alternative embodiments, the program product may have various growth conditions selected from the group consisting of variation in temperature, pH, fermentation products, exposure to various natural gases or compounds, drug efficacy, compound toxicity or survivability.

In further or alternative embodiments, the program product may collect appropriate information involving bacteria growth on a substrate, bacteria sensitivity to a condition and/or bacteria production of metabolites, wherein the appropriate information is categorized into traits which include, but are not limited to, acetic acid major metabolic product, acetic acid minor metabolic product, ADH, ALP, alpha-fucosidase, alpha-galactosidase, alpha-glucosidase, arabinose, ArgA, *bacillus*, beta-galactosidase, beta-glucosidase, beta-glucuronidase, beta-NAG, beta-xylosidase, box car shape, butyric acid major metabolic product, butyric acid minor metabolic product, CAMP, caproic acid major metabolic product, catalase, cellobiose, chartreuse fluorescence, chymotrypsin, $CO_2$ growth, coccus, desulfoviridin, double zone beta-hemolysis, esculin hydrolysis, F/F required, fructose, gelatin hydrolysis, glucose, glycogen, gram reaction, growth in bile, HisA, 1-arabinose, indole, isobutyric acid major metabolic product, isobutyric acid minor metabolic product, isocapronic acid major metabolic product, isocapronic acid minor metabolic product, isovaleric acid major metabolic product, isovaleric acid minor metabolic product, lactate converted to propionate, lactic acid major metabolic product, lactic acid minor metabolic product, lactose, leithinase, LeuA, lipase, maltose, mannitol, mannose, melezitose, melibiose, milk clot formed, milk digested, motile, N-Acetyl-beta-glucosaminidase, nitrate, ONPG(Beta-galactosidase), oxygen tolerance, PheA, phenylacetic acid minor metabolic product, pigment, pitting of agar, ProA, propionic acid major metabolic product, PyrA, raffinose, red fluorescence, reverse CAMP test, rhamnose, ribose, salicin, sensitive to colistin, sensitive to kanamycin, sensitive to SPS, sensitive to vancomycin, sorbitol, spore former, starch hydrolysis, strictly anaerobic, subterminal spore location, succinic acid major metabolic product, succinic acid minor metabolic product, sucrose, terminal spore location, threonine converted to propionate, trehalose, trypsin, TyrA, urease, valeric acid major metabolic product, valeric acid minor metabolic product, xylan, and xylose.

In further or alternative embodiments, the appropriate information may be bacterial response which may be positive, negative, or non responsive. In further or alternative embodiments, the program product may measures bacterial response by smell, color, growth, non-growth, death, symbiosis, and non-symbiosis. In further or alternative embodiments, the program product may collect the appropriate information in computer readable media.

In another aspect are program products for use in computers that executes program instructions recorded on computer-readable media to obtain candidate bacterial species for use in the anaerobic production of hydrogen from a particular biomass, the program products comprise recordable media; and a plurality of computer-readable program instructions on the recordable media that are executable by the computer to perform a method comprising: a) determining a bacterial species of interest; b) determining the appropriate information for the bacterial species of interest; and c) repeating steps a-b for other bacterial species; and d) comparing appropriate information collected from step c to assess optimal candidate bacterial species for use in the anaerobic production of hydrogen from a particular biomass.

In an embodiment of the aforementioned aspect, the program product may collect appropriate information by conducting cultivation systems to identify various bacterial species or selecting response data from the scientific literature, wherein the appropriate information comprises information regarding bacteria growth on a substrate, bacteria sensitivity to a condition and/or bacteria production of metabolites, which may be further categorized into traits which include, but are not limited to, acetic acid major metabolic product, acetic acid minor metabolic product, ADH, ALP, alpha-fucosidase, alpha-galactosidase, alpha-glucosidase, arabinose, ArgA, *bacillus*, beta-galactosidase, beta-glucosidase, beta-glucuronidase, beta-NAG, beta-xylosidase, box car shape, butyric acid major metabolic product, butyric acid minor metabolic product, CAMP, caproic acid major metabolic product, catalase, cellobiose, chartreuse fluorescence, chymotrypsin, $CO_2$ growth, coccus, desulfoviridin, double zone beta-hemolysis, esculin hydrolysis, F/F required, fructose, gelatin hydrolysis, glucose, glycogen, gram reaction, growth in bile, HisA, I-arabinose, indole, isobutyric acid major metabolic product, isobutyric acid minor metabolic product, isocapronic acid major metabolic product, isocapronic acid minor metabolic product, isovaleric acid major metabolic product, isovaleric acid minor metabolic product, lactate converted to propionate, lactic acid major metabolic product, lactic acid minor metabolic product, lactose, leithinase, LeuA, lipase, maltose, mannitol, mannose, melezitose, melibiose, milk clot formed, milk digested, motile, N-Acetyl-beta-glucosaminidase, nitrate, ONPG(Beta-galactosidase), oxygen tolerance, PheA, phenylacetic acid minor metabolic product, pigment, pitting of agar, ProA, propionic acid major metabolic product, PyrA, raffinose, red fluorescence, reverse CAMP test, rhamnose, ribose, salicin, sensitive to colistin, sensitive to kanamycin, sensitive to SPS, sensitive to vancomycin, sorbitol, spore former, starch hydrolysis, strictly anaerobic, subterminal spore location, succinic acid major metabolic product, succinic acid minor metabolic product, sucrose, terminal spore location, threonine converted to propionate, trehalose, trypsin, TyrA, urease, valeric acid major metabolic product, valeric acid minor metabolic product, xylan, and xylose.

In further or alternative embodiments, the program product may involve a cultivation system which comprises growing various bacterial species on particular substrates, under various growth conditions to optimize the bacterial hydrogen production. In further or alternative embodiments, the various growth conditions are selected from the group consisting of variation in temperature, pH, fermentation products, exposure to various natural gases or compounds, drag efficacy, compound toxicity or survivability. In further or alternative embodiments, the appropriate information may be bacterial response that may be positive, negative, or non responsive, and which may be measured by smell, color, growth, non-growth, death, symbiosis, and non-symbiosis. In further or alternative embodiments, the appropriate information is collected in computer readable media.

Nutrient/Biomass Preparation

In another aspect are methods of anaerobically producing hydrogen and other chemical products comprising obtaining biomass material suitable as nutrients for isolated non-heatshocked anaerobic bacteria; concentrating or diluting the biomass material by at least a factor of 2; sterilizing the biomass material, deoxygenating the biomass material; and fermenting the concentrated (or diluted), sterilized, deoxygenated, detoxified, and/or pre-digested biomass material with the isolated non-heatshocked anaerobic bacteria under anaerobic conditions so as to produce hydrogen and other chemical products. In one embodiment, the biomass material is concentrated by at least a factor of 2; in an alternative embodiment, the biomass material is diluted by at least a factor of 2. In an embodiment of this aspect, the hydrogen is produced continuously. In further or alternative embodiments, the fermentation occurs in anaerobic digesters, landfills, trenches, or combinations thereof. In further or alternative embodiments, the concentration step is completed before initiating the sterilization step and/or the deoxygenation step. In further or alternative embodiments, the dilution step is completed before initiating the sterilization step and/or the deoxygenation step. In further or alternative embodiments, the concentration step is initiated after completion of the sterilization step and/or the deoxygenation step. In further or alternative embodiments, the concentration, sterilization and deoxygenation steps overlap. In further or alternative embodiments, the sterilization step is completed before initiating the concentration step and/or the deoxygenation step. In further or alternative embodiments, the sterilization step is initiated after completion of the concentration step and/or the deoxygenation step. In further or alternative embodiments, the biomass material is concentrated by at least a factor of 4. In further or alternative embodiments, the dilution step is initiated after completion of the sterilization step and/or the deoxygenation step. In further or alternative embodiments, the dilution, sterilization and deoxygenation steps overlap. In further or alternative embodiments, the sterilization step is completed before initiating the dilution step and/or the deoxygenation step. In further or alternative embodiments, the sterilization step is initiated after completion of the dilution step and/or the deoxygenation step. In further or alternative embodiments, the biomass material is diluted by at least a factor of 4.

In further or alternative embodiments, the biomass material is concentrated by centrifugation. In further or alternative embodiments, the biomass material is concentrated by reverse osmosis.

In further or alternative embodiments, the biomass material is sterilized with pressurized steam. In further or alternative embodiments, the biomass material is sterilized by autoclaving. In further or alternative embodiments, the biomass material is deoxygenated with pressurized steam. In further or alternative embodiments, the biomass material is deoxygenated by autoclaving. In further or alternative embodiments, the deoxygenated biomass material is further deoxygenated by adding a reducing agent. In further or alternative embodiments, the reducing agent is dithiothreitol, cysteine, thioglycollate, or sodium sulfide. In further or alternative embodiments, the biomass material is sterilized and deoxygenated with pressurized steam. In further or alternative embodiments, the biomass material is sterilized and deoxygenated by autoclaving. In further or alternative embodiments, the sterilized and deoxygenated biomass material is further deoxygenated by adding a reducing agent.

In further or alternative embodiments, the deoxygenated biomass material is suitable for producing hydrogen and other chemical products using isolated non-heatshocked anaerobic bacteria. In further or alternative embodiments, the biomass material is deoxygenated with oxygen scavengers. In further or alternative embodiments, the biomass material is deoxygenated with oxygen scavenger microorganisms. In further or alternative embodiments, the biomass material is deoxygenated with a cellular membrane preparation of oxygen scavenger microorganisms. In further or alternative embodiments, the deoxygenated biomass material contains less than about 100 parts per million of oxygen. In further or alternative embodiments, the deoxygenated biomass material contains less than about 50 parts per million of oxygen. In further or alternative embodiments, the deoxygenated biomass material contains less than about 20 parts per million of oxygen. In further or alternative embodiments, deoxygenated water is added to the concentrated, sterilized, deoxygenated, detoxified, and/or pre-digested biomass material to facilitate growth of the isolated non-heatshocked anaerobic bacteria. In further or alternative embodiments, the isolated non-heatshocked anaerobic bacteria are mixed with deoxygenated water prior to the fermentation step.

In another aspect are methods of anaerobically producing hydrogen which comprise (a) obtaining biomass material suitable as nutrients for isolated non-heatshocked bacteria selected from the group consisting of the following bacteria genera *Acetivibrio, Acetoanaerobium, Acetofilamentum, Acetogenium, Acetothermus, Acidaminobacter, Anaerobiospirillum, Anaerorhabdus, Anaerovibrio, Atopobium, Bacteroides, Bifidobacterium, Bilophila, Butyrivibrio, Campylobacter, Catonella, Centipeda, Dialister, Dichelobacter, Fervidobacterium, Fibrobacter, Fusobacterium, Halanaerobacter, Halanaerobium, Ilyobacter, Johnsonella, Lachnobacterium, Leptotrichia, Malonomonas, Megamonas, Mitsuokella, Oxalobacter, Pectinatus, Pelobacter, Porphyromonas, Prevotella, Propionibacterium, Propionigenium, Propionispira, Rikenella, Roseburia, Ruminobacter, Sebaldella, Selenomonas, Sporomusa, Succinimonas, Succinivibrio, Syntrophobacter, Syntrophomonas, Sutterella, Saponavida, Thermobacteroides, Thermosipho, Thermotoga, Tissierella, Wolinella, Zymophilus, Desulfobacter, Desulfobacterium, Desulfobulbus, Desulfococcus, Desulfomicrobium, Desulfomonas, Desulfomonile, Desulfonema, Desulfosarcina, Desulfotomaculum, Desulfovibrio, Desulfurella, Desulfuromonas, Thermodesulfobacterium, Acidaminococcus, Megasphaera, Syntrophococcus, Veillonella, Coprococcus, Peptococcus, Peptostreptococcus, Ruminococcus, Sarcina, Clostridium, Amoebobacter, Chromatium, Lamprobacter, Thiocapsa, Thiocystis, Thiodictyo, Thiopedia, Thiospirillum, Ectothiorhodospira, Rhodobacter, Rhodocyclus, Rhodomicrobium, Rhodopila, Rhodopseudomonas, Rhodospirillum, Erythrobacter, Methanobacterium, Methanobrevibacter, Methanococcu, Methanococcoides, Methanolobus, Methanolacinia, Methanomi-* crobium, Methanogenium, Methanospirillum, Methanoplanus, Methanothrix, Methanothermus, Methanocorpusculum, Methanoculleus, Methanohalobium, Methanohalophilus, Methanosarcina, Methanosphaera, Eubacterium, Abiotrophia, Atopobium, Gemella, Granulicatella, Finegoldia, Lactobacillus, Actinomyces, Arcanobacterium, Bulleidia, Collinsella, Cryptobacterium, Holdemania, Rothia, Pseudoramibacter, Mogibacterium, Slackia, and Eggerthella; (b) concentrating the biomass material by at least a factor of 2; (c) sterilizing the biomass, (d) deoxygenating the biomass material; and (e) fermenting the concentrated, sterilized, detoxified, deoxygenated and/or pre-digested biomass material with such isolated non-heatshocked anaerobic bacteria under anaerobic conditions so as to produce hydrogen. In an embodiment of this aspect, the hydrogen is produced continuously. In further or alternative embodiments, the fermentation occurs in anaerobic digesters, landfills, trenches, or combinations thereof. In further or alternative embodiments, the concentration step is completed before initiating the sterilization step and/or the deoxygenation step. In further or alternative embodiments, the concentration step is initiated after completion of the sterilization step and/or the deoxygenation step. In further or alternative embodiments, the concentration, sterilization and deoxygenation steps overlap. In further or alternative embodiments, the sterilization step is completed before initiating the concentration step and/or the deoxygenation step. In further or alternative embodiments, the sterilization step is initiated after completion of the concentration step and/or the deoxygenation step. In further or alternative embodiments, the biomass material is concentrated by at least a factor of 4.

In further or alternative embodiments, the biomass material is concentrated by a method selected from centrifugation, reverse osmosis, drying or a combination thereof. In further or alternative embodiments, the biomass material is sterilized by a method selected from pressurized steam or autoclaving. In further or alternative embodiments, the biomass material is deoxygenated by a method selected from pressurized steam, autoclaving, addition of a reducing agent, or a combination thereof. In further or alternative embodiments, the reducing agent is dithiothreitol, cysteine, thioglycollate, or sodium sulfide. In the resulting deoxygenated biomass material is suitable for producing hydrogen using the listed isolated non-heatshocked bacteria species of this aspect.

In further or alternative embodiments, the biomass material is deoxygenated using an agent selected from the group consisting of oxygen scavengers, oxygen scavenging microorganisms, cellular membrane preparation of oxygen scavenging microorganisms, and combinations thereof. In further or alternative embodiments, the deoxygenated biomass material contains less than about 20 parts per million of oxygen. In further or alternative embodiments, the deoxygenated water is added to the concentrated, sterilized, detoxified, deoxygenated, and/or pre-digested biomass material to facilitate growth of the listed isolated non-heatshocked bacteria of this aspect.

In another aspect are methods of anaerobically producing hydrogen comprising (a) obtaining a biomass material suitable as a nutrient for isolated non-heatshocked bacteria selected from the group consisting of anaerobic bacteria (see above); (b) concentrating the biomass material by at least a factor of 2 using centrifugation, reverse osmosis or a combination thereof; (c) sterilizing the biomass, (d) deoxygenating the biomass material; and (e) fermenting the concentrated, sterilized, detoxified, deoxygenated and/or pre-digested biomass material with the listed isolated non-heatshocked anaerobic bacteria under anaerobic conditions so as to produce hydrogen.

In an embodiment of this aspect, the listed bacteria are collected from bovine rumen, soil samples, sludge, anaerobic bacteria cultures, aerobic bacteria cultures, anaerobic sediments from fresh or brackish waters, sewage, animals, animal feces, insect digestive tract; dental samples, hydrothermal soils, hydrothermal pools or deep water hydrothermal vents. In further or alternative embodiments, the hydrogen is produced continuously. In further or alternative embodiments, the fermentation occurs in anaerobic digesters, landfills, trenches, or combinations thereof. In further or alternative embodiments, the concentration step occurs prior to, after, or simultaneously with the sterilization and/or deoxygenation steps. In further or alternative embodiments, the biomass material is concentrated by at least a factor of 4. In further or alternative embodiments, the biomass material is deoxygenated by a method selected from pressurized steam, autoclaving, addition of reducing agents, or combinations thereof. In further or alternative embodiments, the reducing agent is dithiothreitol, cysteine, thioglycollate, or sodium sulfide. In further or alternative embodiments, the resulting deoxygenated biomass material is suitable for producing hydrogen using the listed isolated non-heatshocked bacteria of this aspect.

In further or alternative embodiments, the biomass material is deoxygenated using an agent selected from the group consisting of oxygen scavengers, oxygen scavenging microorganisms, cellular membrane preparation of oxygen scavenging microorganisms, and combinations thereof. In further or alternative embodiments, the deoxygenated biomass material contains less than about 20 parts per million of oxygen. In further or alternative embodiments, the deoxygenated water is added to the concentrated, sterilized, detoxified, deoxygenated, and/or pre-digested biomass material to facilitate growth of the listed isolated non-heatshocked bacteria of this aspect.

In another aspect are methods of anaerobically producing hydrogen comprising obtaining a biomass material suitable as a nutrient for isolated non-heatshocked Clostridia, concentrating the biomass material by at least a factor of 2 via centrifugation, reverse osmosis or a combination thereof; sterilizing the biomass material by a method selected from pressurized steam or autoclaving, deoxygenating the biomass material by a method selected from pressurized steam, autoclaving, addition of reducing agents, or combinations thereof, wherein the deoxygenated biomass material contains less than about 20 parts per million of oxygen; and fermenting the concentrated, deoxygenated, detoxified, and/or pre-digested biomass material with the isolated non-heatshocked anaerobic bacteria under anaerobic conditions in an anaerobic digestor so as to produce hydrogen.

In an embodiment of this aspect, the hydrogen is produced continuously. In further or alternative embodiments, the fermentation occurs in anaerobic digester, landfills, trenches, or combinations thereof. In further or alternative embodiments, the concentration step occurs prior to, after, or simultaneously with the sterilization and/or deoxygenation steps. In further or alternative embodiments, the biomass material is concentrated by at least a factor of 4. In further or alternative embodiments, the reducing agent is dithiothreitol, cysteine, thioglycollate, or sodium sulfide. In the resulting deoxygenated biomass material is suitable for producing hydrogen using isolated non-heatshocked Clostridia.

In further or alternative embodiments, the biomass material is further deoxygenated using an agent selected from the group consisting of oxygen scavengers, oxygen scavenging microorganisms, cellular membrane preparation of oxygen scavenging microorganisms, and combinations thereof. In further or alternative embodiments, the deoxygenated water is added to the concentrated, sterilized, deoxygenated, detoxified, and/or pre-digested biomass material to facilitate growth of the isolated non-heatshocked *Clostridia*.

In another aspect are methods of anaerobically producing hydrogen comprising obtaining a biomass material suitable as a nutrient for isolated non-heatshocked *Clostridia*, wherein the biomass material comprises molasses, raw paper, agricultural waste, or mulch; concentrating the biomass material by at least a factor of 2 via centrifugation, reverse osmosis or a combination thereof; sterilizing the biomass material by a method selected from pressurized steam or autoclaving, deoxygenating the biomass material by a method selected from pressurized steam, autoclaving, addition of reducing agents, or combinations thereof, wherein the deoxygenated biomass material contains less than about 20 parts per million of oxygen; and fermenting the concentrated, sterilized, deoxygenated, detoxified, and/or pre-digested biomass material with the isolated non-heatshocked anaerobic bacteria under anaerobic conditions in an anaerobic digester so as to produce hydrogen. In an embodiment of this aspect, the hydrogen is produced continuously. In further or alternative embodiments, the fermentation occurs in anaerobic digesters, landfills, trenches, or combinations thereof. In further or alternative embodiments, the concentration step occurs prior to, after, or simultaneously with the sterilization and/or deoxygenation steps. In further or alternative embodiments, the biomass material is concentrated by at least a factor of 4.

In further or alternative embodiments, the reducing agent is dithiothreitol, cysteine, thioglycollate, or sodium sulfide. In further or alternative embodiments, the resulting deoxygenated biomass material is suitable for producing hydrogen using isolated non-heatshocked *Clostridia*. In further or alternative embodiments, the biomass material is further deoxygenated using an agent selected from the group consisting of oxygen scavengers, oxygen scavenging microorganisms, cellular membrane preparation of oxygen scavenging microorganisms, and combinations thereof. In further or alternative embodiments, the deoxygenated water is added to the concentrated, sterilized, deoxygenated, detoxified, and/or pre-digested biomass material to facilitate growth of the isolated non-heatshocked *Clostridia*.

In another aspect are methods for producing a nutrient suitable for non-heatshocked anaerobic bacteria to produce hydrogen comprising removing substantially all of the oxygen from a biomass by a method selected from pressurized steam, autoclaving, addition of a reducing agent, or combinations thereof.

In another aspect are nutrients suitable for non-heatshocked anaerobic bacteria to produce hydrogen comprising prepared by removing substantially all of the oxygen from a biomass by a method selected from pressurized steam, autoclaving, addition of a reducing agent, or combinations thereof. In an embodiment of this aspect, the nutrients are further prepared by concentrating the biomass using centrifugation, reverse osmosis or a combination thereof, and sterilizing the biomass by means of pressurized steam or autoclaving.

Isolation/Enrichment System

In another aspect are methods for selecting bacteria for use in anaerobic hydrogen production comprising isolating anaerobic bacterial strains for their ability to use biomass as nutrients and measuring collected hydrogen gas produced, wherein the anaerobic bacteria do not require heatshocking in order to anaerobically produce hydrogen and other chemical products from the biomass. In an embodiment of their aspect, the bacteria are placed into a sealed chamber with substantially deoxygenated water and various types of biomass. In further or alternative embodiments, the sealed chamber ultimately hosts an anaerobic environment. In further or alternative embodiments, the sealed chamber can provide a multiplicity of growth conditions. In further or alternative embodiments, the multiplicity of growth conditions are selected from the group consisting of, variation in temperature, pressure, pH, fermentation products, exposure to various natural gases or compounds, drug efficacy, drug resistance, compound toxicity or survivability. In further or alternative embodiments, the sealed chamber has a shape selected from the group consisting of a circular, cylindrical, spherical, square, or rectangular form. In further or alternative embodiments, the sealed chamber has a volume of 100 $cm^3$ to 50,000 $cm^3$.

In further or alternative embodiments, isolated non-heatshock anaerobic bacteria are taken from the sealed chamber and further selected by cultivation systems. In further or alternative embodiments, the cultivation systems comprise growing various bacterial species on particular substrates, under various growth conditions to optimize the bacterial hydrogen production. In further or alternative embodiments, the isolated non-heatshock anaerobic bacteria are selected by its production of hydrogen, including by way of example only, at least 5%, at least 10%, at least 15%, at least 20%, at least 25%, or at least 30% of the total theoretical amount of hydrogen that could be produced from a particular biomass. In further or alternative embodiments, the isolated non-heatshock anaerobic bacteria are selected by its production of 2 moles of hydrogen per mole of substrate produced. In further or alternative embodiments, the various growth conditions are selected from the group consisting of variation in temperature, pressure, pH, fermentation products, exposure to various natural gases or compounds, drug efficacy, compound toxicity or survivability.

In further or alternative embodiments, the isolated non-heatshock anaerobic bacteria are taken from the sealed chamber and further selected in cultivation systems after 1-7 days. In further or alternative embodiments, the isolated non-heatshock anaerobic bacteria are taken from the sealed chamber and further selected in cultivation systems after 1-20 weeks.

In another aspect are apparatuses for selecting bacteria for use in anaerobic hydrogen production which comprise sealed chambers capable for providing anaerobic environments and multiplicities of growth conditions. In an embodiment of this aspect, the bacteria are collected from bovine rumen, soil samples, sludge, anaerobic bacteria cultures, aerobic bacteria cultures, anaerobic sediments from fresh or brackish waters, sewage, animals, animal feces, insect digestive tract, dental samples, hydrothermal soils, hydrothermal pools or deep water hydrothermal vents. In further or alternative embodiments, the apparatuses further contain substantially deoxygenated water.

In further or alternative embodiments, the multiplicities of growth conditions are selected from the group consisting of variation in temperature, pressure, pH, fermentation products, exposure to various natural gases or compounds, drug efficacy, compound toxicity or survivability. In further or alternative embodiments, the sealed chambers have shapes selected from the group consisting of circular, cylindrical, spherical, square, or rectangular forms. In further or alternative embodiments, the sealed chambers further have shapes having volumes of 100 $cm^3$ to 50,000 $cm^3$. In further or alternative embodiments, the apparatuses further comprise at least one bacterial strain that produces hydrogen and other chemical products anaerobically. In further or alternative embodiments, the apparatuses further contain particular biomass samples the bacteria use as nutrients for producing hydrogen gas and other chemical products.

In further or alternative embodiments, the bacteria selected from the sealed chambers are removed without substantially disturbing the anaerobic environment. In further or alternative embodiments, the bacteria are selected from the sealed chambers by use of needles or by means of a vacuum. In further or alternative embodiments, the apparatus comprises at least two substantially parallel glass plates. In further or alternative embodiments, the apparatus further comprises a seal on at least one side that is penetrable by needles.

Use of Bacteria and Bacterial Cultures to Produce Hydrogen and Other Chemical Products In another aspect are bacterial cultures which comprise purified bacterial strains, in which the bacterial strains have not undergone a heatshocking process and they produce hydrogen by anaerobically fermenting biomass. In further or alternative embodiments, the biomass has been deoxygenated. In further or alternative embodiments, are the biomass has been sterilized. Further or alternative embodiments are the biomass has been concentrated. In further or alternative embodiments, the biomass has been deoxygenated and concentrated. In further or alternative embodiments, the biomass has been sterilized, deoxygenated, concentrated, detoxified, and/or pre-digested. In further or alternative embodiments, the bacterial strains have been selected by means of a Knowledge Management System. In further or alternative embodiments, the bacterial strains have been selected by means of isolation/enrichment systems. In further or alternative embodiments, the bacterial strains have been isolated by means of isolation/enrichment systems. In further or alternative embodiments, the bacterial strains have been isolated by means of isolation/enrichment systems and have been selected by means of a Knowledge Management System. In further or alternative embodiments, the biomass comprises material from at least one member of the genus *Capsicum*. In still further or alternative embodiments, the member of the genus *Capsicum* is selected from the group consisting of *Capsicum anuum, Capsicum baccatum, Capsicum chinense, Capsicum gemnifolium, Capsicum frutescens, Capsicum pubescens*, and combinations thereof. In further or alternative embodiments, the biomass comprises material from at least one member of the genus *Allium*. In still further or alternative embodiments, the member of the genus *Allium* is selected from the group consisting of *Allium sativum, Allium cepa, Allium schoenoprasum, Allium tuberosum, Allium ampeloprasum*, and combinations thereof. In further or alternative embodiments, the biomass comprises sugar products. In further or alternative embodiments, the sugar products include material from at least one member of the genus *Saccharum*. In still further or alternative embodiments, the member of the genus *Saccharum* is a species selected from the group consisting of *Saccharum spontaneum, Saccharum robustum, Saccharum officinarum, Saccharum barberi, Saccharum sinense, Saccharum edule*, and combinations thereof. In further or alternative embodiments, the biomass comprises cellulose products. In still further or alternative embodiments, the cellulose products includes wood pulp. In further or alternative embodiments, the biomass comprises material from at least one species selected from the group consisting of *Solanum Esculentum, Solarium melongena, Solarium tuberosum, Lycopersicon esculentum, Beta vulgaris*, and combinations thereof. In further or alternative embodiments, the bacteria cultures are used to produce hydrogen and other chemical products. In further or alternative embodiments, the chemical products are selected from the group consisting of gases, solids, solvents, volatile organic acids, salts of volatile organic acids, and combinations thereof. In further or alternative embodiments, the chemical product is a gas selected from the group consisting of carbon dioxide, carbon monoxide, hydrogen sulfide, ammonia, nitrogen, and combinations thereof. In further or alternative embodiments, the chemical product is a solid that comprises sulfur. In further or alternative embodiments, the solid is elemental sulfur. In further or alternative embodiments, the solvents are selected from the group consisting of acetone, butanol, ethanol, propanol, isopropanol, 1,2-propanediol, and combinations thereof. In further or alternative embodiments, the volatile organic acids are selected from the group consisting of formic acid, acetic acid, propionic acid, butyric acid, valeric acid and combinations thereof. In further or alternative embodiments, the salts of volatile organic acids comprise anions selected from the group consisting of formate, acetate, propionate, butyrate, valerate, and combinations thereof. In further or alternative embodiments, the salts of volatile organic acid comprise cations selected from the group consisting of alkali metal ions, alkaline earth ions, ammonium ions, and combinations thereof. In further or alternative embodiments, the cations are $Na^+$, $K^+$, $Ca^{2+}$, $Mg^{2+}$, $NH_4^+$, and combinations thereof. In further or alternative embodiments, the bacteria cultures comprise substantially purified single bacterial strains. In further or alternative embodiments, the substantially purified single bacterial strains are at least 95% purified. In further or alternative embodiments, the substantially purified single bacterial strains are at least 99% purified. In further or alternative embodiments, the substantially purified single bacterial strains are at least 99.5% purified.

In further or alternative embodiments, the Knowledge Management System comprises a program product for use in a computer that executes program instructions recorded in a computer-readable media to obtain candidate bacterial species for use in the anaerobic production of hydrogen from a particular biomass. In further or alternative embodiments, the program product comprises a recordable medium and a plurality of computer-readable program instructions on the recordable media that are executable by the computer to perform a method comprising: a) determining a bacterial species of interest; b) determining the appropriate information for the bacterial species of interest; c) repeating steps a-b for other bacterial species; and d) comparing appropriate information collected from step c to assess optimal candidate bacterial species for use in the anaerobic production of hydrogen from a particular biomass. In further or alternative embodiments, the appropriate information is collected by conducting cultivation systems to identify various bacterial species. In further or alternative embodiments, the cultivation systems comprise growing various bacterial species on particular substrates, under various growth conditions to optimize the bacterial hydrogen production.

In further or alternative embodiments, the isolation/enrichment system is a sealed chamber containing substantially deoxygenated water and at least one biomass sample used to anaerobically ferment the at least one biomass. In further or alternative embodiments, the isolation/enrichment system ultimately hosts an anaerobic environment. The isolation/enrichment system can provide a multiplicity of growth conditions. In further or alternative embodiments, the isolation/enrichment system has a shape selected from the group consisting of a circular, cylindrical, spherical, square, or rectangular form.

In further or alternative embodiments, the bacterial strains are used to produce hydrogen by anaerobically fermenting biomass in anaerobic fermentation apparatuses. In further or alternative embodiments, the anaerobic fermentation apparatuses comprises: sterilization and deoxygenation systems; anaerobic digesters containing a population of substantially purified anaerobic bacteria and equipped with an anaerobic digester control systems; plurality of pipelines and pumps for introducing and re-circulating biomass, and removal pipelines connected to the anaerobic digesters for removing chemical products from the anaerobic digesters. In further or alternative embodiments, the anaerobic digester control systems are used to optimally operate the anaerobic digesters and which comprise: process control tools; metrology tools to acquire metrology data relating to anaerobic fermentation parameters; process controllers operatively coupled to the process control tools and the metrology data, wherein the process controllers comprise decision making units, input/output boards, and database units to store the metrology data.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

BRIEF DESCRIPTION OF THE DRAWINGS

FIG. 3 presents one potential screen shot of a display page from the Knowledge Management System that lists bacterial species and traits.

FIG. 4 presents one potential screen shot of a display page from the Knowledge Management System showing a preferred test that displays specific traits the bacteria are tested for a response.

FIG. 5 presents one potential screen shot of a display page from the Knowledge Management System detailing appropriate information collected on the bacteria *Bilophila wadsworthia*.

DETAILED DESCRIPTION OF THE INVENTION

Glossary of Certain Terms

Figure 1:
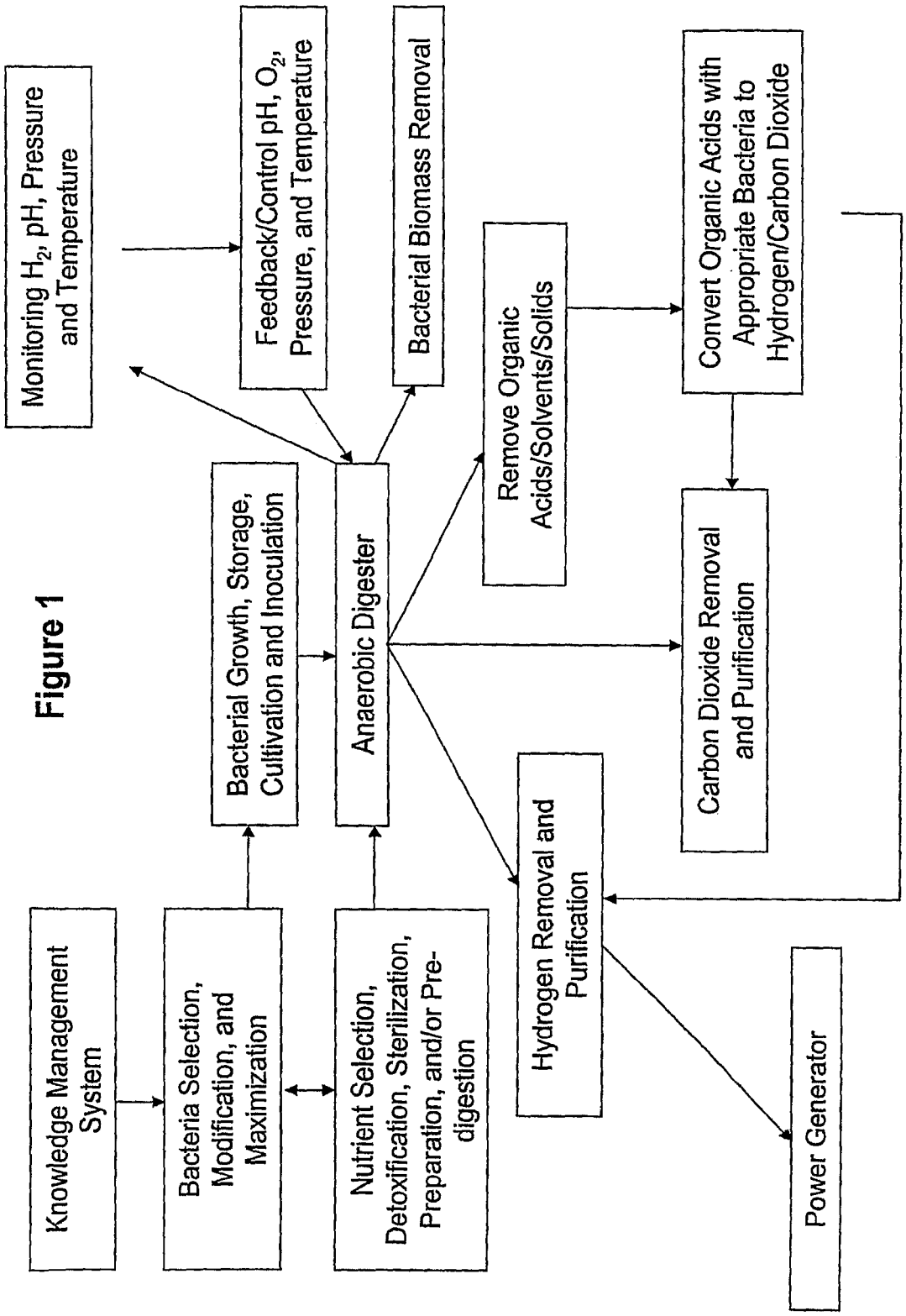
FIG. 1 presents one potential schematic showing the various aspects of the present invention.

The term "anaerobic" or "anoxic", as used herein, refers to an environment in which the oxygen has been substantially removed. By way of example only, the oxygen concentration may be less than 10000 ppm, or the oxygen concentration may be less than 1000 ppm, or the oxygen concentration may be less than 100 ppm, or the oxygen concentration may be less than 50 ppm, or the oxygen concentration may be less than 20 ppm The term "anaerobic fermentation", as used herein, refers to an anaerobic process in which biomass is degraded to chemical products such as, by way of example only, hydrogen, carbon dioxide, volatile organic acids, hydrogen sulfide, methane, sulfur, and carbon monoxide.

The term "anaerobic respiration", as used herein, refers to a process in which organic substrates are degraded to $CO_2$, but using a substance other than oxygen as the terminal electron acceptor. Some bacteria respire by using nitrate or sulfate ions as the terminal electron acceptor during respiration.

The term "assemblage" as used herein, refers to combination of components interconnected to achieve a desired function. The assemblage may be a stand alone system or a system incorporated into another assemblage. The function of the assemblage includes, but is not limited to, the production of chemical products by anaerobically fermenting biomass, the monitoring and control of anaerobic fermentation systems, and generation power and low pressure steam.

The terms "biomass", as used herein, refers to any animal or plant derived material that contains one or more components that can be converted, bioconverted or biodegraded into a useful material by anaerobic fermentation.

The term "bacteria culture", as used herein, refers to growing of bacteria in a specially prepared nutrient medium.

The term "energy crops", as used herein, refers to plants which are grown for use as a source of biomass for fuel.

The term "feedstock", as used herein, refers to a source of chemical products used industrially to generate new chemical products and compositions, and it also refers to biomass sources.

The term "fermentation", as used herein, refers to a biological process in which organic compounds are partially degraded; for example, yeasts ferment sugars to alcohol.

The terms "heatshocking" and "heatshocking process", as used herein, refers to the process of heating a microbial community, such as an inoculum or a sample containing multiple bacterial strains, to eliminate undesired strains, such as non-spore forming (vegetative) bacteria, e.g. methanogens, with desired strains, such as spore forming bacteria, surviving the procedure for future growth in better conditions. A non-limiting example of a heatshocking process is to heat up the mixture of bacteria to 105° C. for up to 2 hours.

The terms "heatshocking" and "heatshocking process", as used herein, may also refer to the induction of specific chemical pathways and/or a redirection of protein synthesis that involves diversion from induction and synthesis of other proteins.

The term "heatshocked", as used herein, refers to having undergone a heatshocking process.

The term "metrology tool", as used herein, refers to as measurement tool, with the information obtained referred to herein as "metrology data".

The term "substantially deoxygenated," as used herein, refers to a biomass or bacteria culture media in which there has been a reduction of the oxygen concentration. By way of example only, the oxygen concentration may be less than 10000 ppm, or the oxygen concentration may be less than 1000 ppm, or the oxygen concentration may be less than 100 ppm, or the oxygen concentration may be less than 50 ppm, or the oxygen concentration may be less than 20 ppm. In embodiments when "substantially deoxygenated" refers specifically to a reduction of the concentration of oxygen in an aqueous solution, then the term "substantially deoxygenated" means less than 5 ppm of oxygen in the aqueous solution, including less than 4 ppm of oxygen, less than 3 ppm of oxygen, less than 2 ppm of oxygen, and less than 1 ppm of oxygen.

The term "substantially parallel," as used herein, refers to the distance between walls of the isolation/enrichment system which may differ by a certain amount along the length of the isolation/enrichment system. By way of example only, the distance between walls of the isolation/enrichment system may differ up to 5% along the length of the isolation/enrichment system, or the distance between walls of the isolation/enrichment system may differ up to 1% along the length of the isolation/enrichment system, or the distance between walls of the isolation/enrichment system may differ up to 0.5% along the length of the isolation/enrichment system. Perfectly parallel walls would have no difference in width along the length of the isolation/enrichment system.

The term "substantially purified," as used herein, refers to a bacterial culture in which there has been a reduction of some biological component in the culture media such as, by way of example only, viruses, pathogens, toxins and bacteria strains, other than the bacterial strain of interest.

Hydrogen Production

One approach to hydrogen production that may prove economically viable uses biological conversion of energy crops and industrial and agricultural wastes and residues into hydrogen and other chemical products. Hydrogen gas is an environmentally friendly energy source, as it may be used to generate electricity without producing greenhouse gas emissions. Currently, most hydrogen is produced by "steam reforming" of methane, which predominantly relies on natural gas as a source of methane and energy. In this process, natural gas and a chemical catalyst are mixed with steam at high temperatures and pressure to form hydrogen and carbon dioxide. In this process a non-renewable energy source is used to generate hydrogen, thus; it would be ideal to replace the fossil fuels with renewable energy sources, such as hydrogen production via biomass fermentation. Potential hydrogen production may be derived from renewable energy sources such as, but not limited to, energy crops, surplus agricultural products, waste from sugar production and processing facilities, animal waste from zoos, waste from fruit processing industries, waste from pulp and paper mills, silvaculture residues, waste from wood processing, waste from agricultural product processing, food waste, solids isolated from fermentation cultures, municipal sewer waste, animal manure, animal urine, animal parts, fish parts, and combinations thereof.

The future energy economy may have an important role for hydrogen as a clean, carbon dioxide neutral energy source for use in, by way of example only, fuel cell vehicles and for decentralized electricity generation in stationary fuel cell systems. In fuel cells, hydrogen can be converted to electricity very efficiently, producing only water as a waste product, thus drastically reducing carbon dioxide, nitric oxide, particulate and other emissions that accompany the use of fossil fuels. Although the use of hydrogen produced from fossil sources can lead to a substantial reduction of emissions, the energy efficiency of the production-to-end-use chain (from natural gas to hydrogen to electricity) is limited. This is due to energy losses in the hydrogen production phase with concomitant carbon dioxide capture. In the long run, hydrogen would ideally be produced from renewable sources such as the electrolysis of water with renewable electricity, or by means of biomass gasification, or biological fermentation or photobiological hydrogen production. With large-scale implementation of renewable energy production, hydrogen can be a clean carrier of energy for storage and transport.

Hydrogen can be produced from a variety of feedstocks using a variety of process technologies. Feedstock options include fossil resources such as coal, natural gas, and petroleum, and renewable resources such as biomass, sunlight and wind. Process technologies include thermochemical, biological, electrolytic and photolytic. Associated with each potential feedstock or energy source are unique challenges and benefit trade-offs. Fossil feedstocks, for example, are widely available and relatively well understood and accepted, but until carbon sequestration becomes feasible, greenhouse gas emissions make fossil feedstocks environmentally difficult. Biomass, on the other hand, has very small or even negative net carbon emissions, but has presented challenges with biomass collection, transportation, availability, and storage. Hydrogen produced from biomass fermentation has not been cost competitive with gasoline because biomass and capital costs are high. Improved biomass/agriculture technology (higher yields per acre, etc.); lower cost biomass collection, transportation, and storage options; and improved biomass preparation are needed. In addition, biomass sources are often seasonal in nature, therefore biomass-flexible processes and/or cost effective biomass storage are needed for year round operation.

All renewable energy sources are ultimately based on solar energy which is made available through photovoltaic cells, wind energy or stored as chemical energy in biomass. Thus, biomass essentially stores solar energy in chemical form, wherein the potential energy is releases in the form of hydrogen during anaerobic fermentation. In addition, hydrogen production may also result from direct photobiological processes. Biomass sources available for conversion into hydrogen include, but are not limited to, dedicated bioenergy crops and/or less expensive residues, such as organic waste from regular agricultural farming and wood processing (biomass residues). In contrast, direct photobiological hydrogen production, does not require biomass, as water is directly cleaved by photosynthetic microorganisms. Regardless, hydrogen production by these biological means is attractive due to the renewable energy nature of solar energy.

A distinction can be made between the use of dry biomass (such as wood) and the use of wet biomass sources such as the organic fraction of domestic waste, agro-industrial wastes and slurries, and wastewater. Dry biomass is used for thermal conversion processes that require minimal water content such as green electricity generation (via combustion or gasification) or the production of renewable diesel fuel through gasification, followed by Fischer-Tropsch synthesis. Wet biomass and residues are typically less suitable for thermal conversion because transport and drying require a considerable amount of energy, which leads to a limited or even negative overall carbon dioxide reduction. The available amount of wet biomass and residues is however considerable, such that their use as sources for renewable energy production is desirable. Biological conversion processes are particularly useful for this application because they are catalyzed by microorganisms in an aqueous environment at low temperature and pressure. Furthermore these techniques are well suited for decentralized energy production in small-scale installations in locations where biomass or wastes are available, thus avoiding energy expenditure and costs for transport. The general expectation is that biological processes may play a substantial role in the production of renewable gaseous and liquid biofuels including methane, hydrogen, bioethanol and ABE (Acetone-Butanol-Ethanol).

Hydrogen production from biomass has been thought to be an expensive process. This is reflected when comparing the higher costs for biomass, distribution, and fixed capital costs relative to other production methods such as natural gas reforming. In addition, due to the heterogeneity of biomass, the localized production of biomass, and the relatively high costs of gathering and transporting biomass sources, digester complexes dedicated for biomass gasification are limited to midsize-scale operations. Additionally, factors not associated in the economic analysis are fertilizer costs, the environmental impact associated with the production, harvest, and transport of biomass, or any potential degradation in land quality associated with intensive bioenergy crop farming. Increased efficiency of continuous hydrogen production may be obtained by improvements in systems, methods and compositions used for anaerobic bacterial fermentation. The ability to effectively utilize a variety of biomass types, and the development of localized energy production from decentralized fuel cell power stations, may ultimately decrease biomass harvest and transportation issues.

Production of Hydrogen and Other Chemical Products from Biomass

The production of hydrogen is a ubiquitous, natural phenomenon under anaerobic conditions. A wide variety of bacteria, from swamps, sewage, hot springs, and the rumen of cattle are able to convert organic matter to hydrogen, carbon dioxide and other chemical products including, but not limited to, acetic acid, butryric acid, lactate, and ethanol. In general, these bacteria live in the close proximity to other bacteria which consume the chemical products, including hydrogen, producing their own endproducts like methane and carbon dioxide. In this way, a stable ecosystem is formed wherein hydrogen consumers remove hydrogen, and allow continued growth of hydrogen producers, which would otherwise be inhibited by high concentrations of hydrogen.

In anaerobic environments, hydrogen is commonly produced during microbial breakdown of organic compounds. When organic compounds are the sole carbon and energy source providing metabolic energy under anaerobic conditions, the process is termed "dark hydrogen fermentation", or "dark fermentation". When light is required to provide additional energy, the process belongs to the category of photobiological processes and is termed "photo-fermentation".

When bacteria grow on organic substrates (heterotrophic growth), these substrates are degraded by oxidation to provide building blocks and metabolic energy for growth. This oxidation generates electrons which need to be disposed of in order to maintain electrical neutrality. In aerobic environments, oxygen is reduced and water is the product, however, in anaerobic environments no oxygen is present and therefore other compounds act as electron acceptors. For instance, protons accept electrons and are thereby reduced to molecular hydrogen ($H_2$). In "dark fermentation" a wide variety of bacteria use the reduction of protons to dispose of reducing equivalents which results from primary metabolism. Other examples of alternative electron acceptors in anaerobic environments are nitrate with nitrogen gas ($N_2$) as the product or sulfate with dihydrogensulfide ($H_2S$) as the reduced product. Even organic compounds can act as electron acceptors. For instance, the microbial production of butanol occurs through the reduction of butyric acid. The capacity to reduce other electron acceptors than oxygen requires the presence of a specific enzyme system in the micro-organisms: hydrogen producing bacteria possess hydrogenase enzymes; nitrate reducing bacteria possess an elaborate set of enzymes catalyzing the stepwise reduction of nitrate to nitrogen etc.

Anaerobic microbiological decomposition is a process in which micro-organisms derive energy and grow by metabolizing organic material in an oxygen-free environment resulting in the production of various end-products. The anaerobic digestion process can be subdivided into four phases, each requiring its own characteristic group of micro-organisms: hydrolysis (conversion of non-soluble biopolymers to soluble organic compounds), acidogenesis (conversion of soluble organic compounds to volatile organic acids, also referred to as volatile fatty acids, and carbon dioxide), acetogenesis (conversion of carbohydrates or volatile organic acids to acetate and hydrogen), and methanogenesis (conversion of organic acids or acetate and carbon dioxide plus hydrogen to methane gas). The acidogenic bacteria excrete enzymes for hydrolysis and convert soluble organics to volatile organic acids and alcohols. Volatile organic acids and alcohols are then converted by acetogenic bacteria into acetic acid or hydrogen and carbon dioxide. Methanogenic bacteria then use acetic acid, hydrogen and carbon dioxide to produce methane.

Bio-methane production through anaerobic digestion of wastes and wastewater using mixtures of bacteria species is an established technology. The final biogas product is a mixture of methane (55-75 vol. %) and carbon dioxide (25-45 vol. %) which can be used for heating, upgrading to natural gas quality or co-generation of electricity and heat. The biogas yield varies with the type and concentration of the biomass and process conditions. However, there are many disadvantages of conventional anaerobic treatment for methane production, including a high sensitivity of methanogenic bacteria to a large number of chemical compounds, the first start-up of an installation without the presence of proper seed sludge can be time-consuming due to the low growth yield of anaerobic bacteria, and the anaerobic treatment can be accompanied by odor due to the formation of sulfide when treating wastewater containing sulfurous compounds. During this methane production through anaerobic digestion of wastewater and residues (including sewage sludge, manure and the organic fraction of municipal waste) hydrogen is an intermediary product, which is not available because it is rapidly taken up and converted into methane by methane-producing microorganisms. Also present are organisms that compete for nutrients and create undesirable end products. The final gas produced in this method is also contaminated with hydrogen sulfide, ammonia, and siloxanes which damage energy producing equipment. This method can also be time consuming and resource intensive due to extended hydraulic retention times. Thus, to achieve efficient hydrogen production from anaerobic fermentation, as achieved using the methods disclosed herein, methanogenic bacteria mixed with hydrogen producing bacteria, thereby eliminating the possibility of hydrogen consumption. The methods described herein decouple hydrogen formation and consumption such that hydrogen is available as the final product.

Anaerobic Production of Hydrogen and Other Chemical Products from Biomass

The present approach takes advantage of emulating a natural environment for anaerobic bacterial growth in order to achieve optimal hydrogen production. This is contrary to previous less efficient attempts at hydrogen production using anaerobic fermentation by genetically modifying bacteria or by forcing bacteria to exist in unnatural environments and coaxing them to produce hydrogen. FIG. 1 depicts one approach of the methods described herein, wherein hydrogen is produced under anaerobic conditions, using anaerobic bacteria to anaerobically ferment different types of biomass. Central to the approach is the Anaerobic Digester, in which the natural environment for anaerobic bacterial growth is emulated to achieve optimal hydrogen production. The digester operating parameters (such as, by way of example only, pH, pressure and temperature) are monitored and adjusted accordingly in order to control and maintain the appropriate environment. Similarly, the concentrations of the fermentation products are monitored and the products removed from the digester in order to maintain optimal anaerobic fermentation conditions in the digester, with optimal hydrogen production. By way of example only, such products removed may include organic acids/solvents/solids, bacterial biomass, carbon dioxide and hydrogen.

One aspect of the approach, shown in FIG. 1, is the selective isolation of anaerobic bacteria, which use particular types of biomass, and are abundant hydrogen producers. This selection, modification and maximization is achieved by utilizing an anaerobic bacteria isolation/enrichment system in which a variety of food sources are arranged, and the system is deoxygenated and inoculated with a mixture of bacteria obtained from different sources. The bacteria are allowed to grow in the isolation/enrichment system, and those that thrive on a particular biomass are removed and evaluated for specific substrate utilization and end products generated. These bacteria are placed in a separate cultivation system for continued growth using the optimal biomass indicated from the isolation/enrichment system. The cultivation systems allow for the isolation of bacteria on particular substrates under various growth conditions to optimize hydrogen production. Various growth conditions may include variation in temperature, pH, fermentation products, exposure to various natural gases or compounds, drug efficacy, compound toxicity or survivability. The cultivation system aids in determining the primary food source for particular bacteria strains and the optimal growing conditions. The isolated bacteria are then harvested from the cultivation system and stored for later use as inoculum for hydrogen production in anaerobic digesters. Of importance to the successful operation of the anaerobic digester is the selection of nutrients for a particular bacteria species, and the preparation, detoxification, sterilization and/or pre-digestion of nutrients prior to introduction into the digester. The selection of nutrients is known from the enrichment/incubation process, in which the bacteria species was originally isolated. Finally, the information obtained for a particular species of bacteria, such as, by way of example only, optimal biomass, optimal growth pH, optimal growth temperature, and fermentation products, are compiled into a database. A Knowledge Management System, which includes the database of information, can be later utilized to identify an optimal bacterial species for use in producing hydrogen from a particular biomass, rather than trying to genetically engineer the bacteria to ferment the biomass. However, bacteria may be obtained by genetic modification of known bacterial strains and evaluated in the isolation/enrichment system. The genetic modification of the bacterila strains may results from transformation procedures, bacterial conjugation, transduction, interaction of bactrial strains with mutagens and combinations thereof. The mutagens used may include, but are not limited to, chemicals, ultraviolet light, and radioactive element.

By way of example volatile fatty acids produced include formic, acetic, propionic, isobutyric, butyric, isovaleric, valeric, isocaproic, caproic, and heptanoic acids. By way of example alcohol products from fermentation include ethanol, ethanol, propanol, isobutanol, butanol, isopentanol, pentanol, acetone, propanol, isopropanol, and 1, 2-propanediol. By way of example non-volatile products from fermentation include pyruvic, lactic, oxalacetic, oxalic, methyl malonic, malonic, fumaric, succinic.

Knowledge Management System

Figure 2:
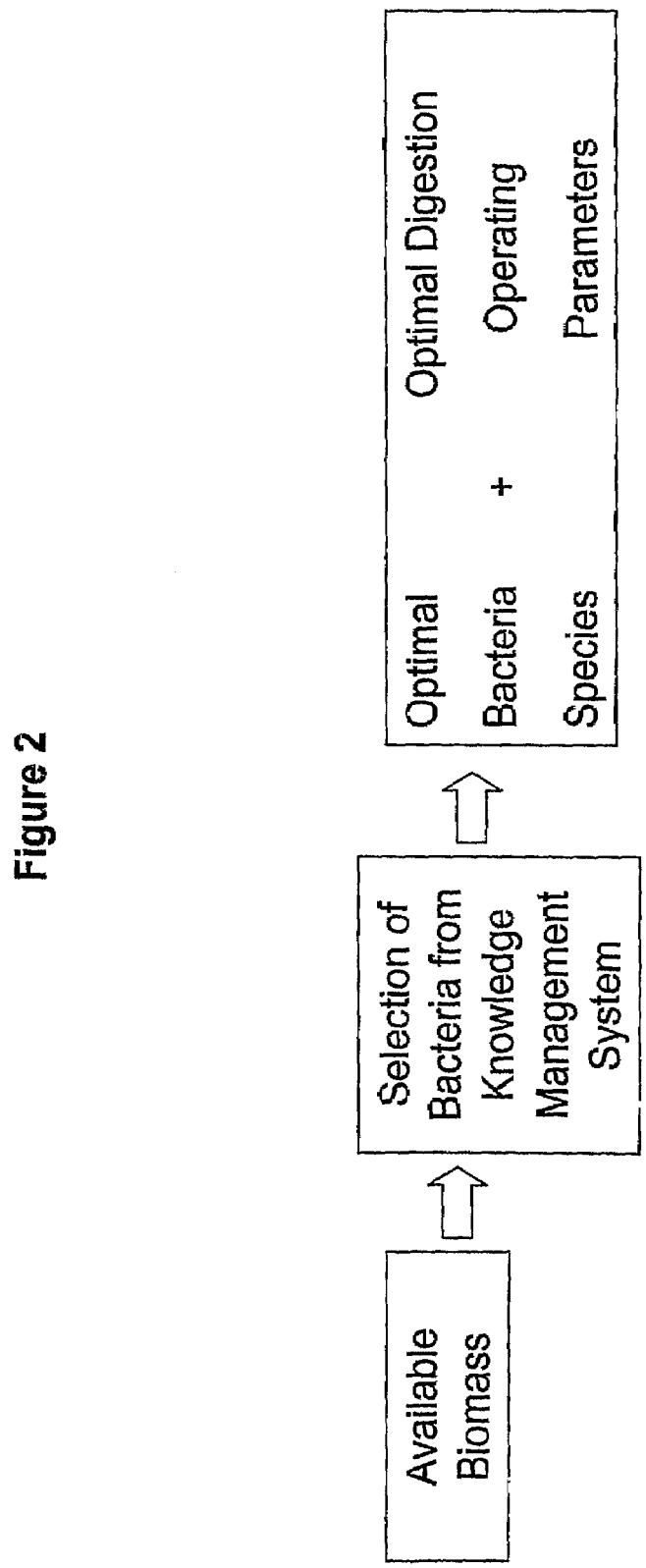
FIG. 2 presents one potential schematic illustrating the use of the Knowledge Management System for utilization of a particular biomass.

One aspect of the methods described herein is the creation of a database by compilation of information regarding the hydrogen producing characteristics of various isolated bacteria genera and species, along with optimal biomass used by the respective bacteria and optimal conditions. This database is incorporated into a Knowledge Management System, which is an effective tool for exploitation of anaerobic hydrogen production as an alternative energy source. The type of biomass available for hydrogen production via anaerobic fermentation may vary. As shown in FIG. 2, the Knowledge Management System allows for the identification of bacteria, with known hydrogen producing characteristics for a particular biomass, and the optimal digester operating parameters for anaerobic fermentation of the specific biomass available. This system therefore can minimize the time required for the discovery, research, and development process, and thereby increase the efficiency of an energy plant based on anaerobic fermentation.

The Knowledge Management System software includes user friendly options that aid the user in navigating the system. Such options include creating new identifications, opening identifications, saving an identification, opening a session, saving a session, importing data, finding an organism, finding an indicator test, finding a reference, finding a photo, comparing organisms, showing related organisms, finding common traits, adding organisms, adding traits, adding the source, user login, user logout, checkout of organisms, checking of organisms, testing the server, reports on identifiability, column sorting, preferred tests, sorting organisms, starting over, and switch to relatedness mod. The Knowledge Management System houses data that can be quickly accessed and manipulated into a user friendly form such as a graph or spreadsheet. In particular, the Knowledge Management System can narrow down which bacteria uses particular nutrients for producing a specific amount of hydrogen.

Figure 3:
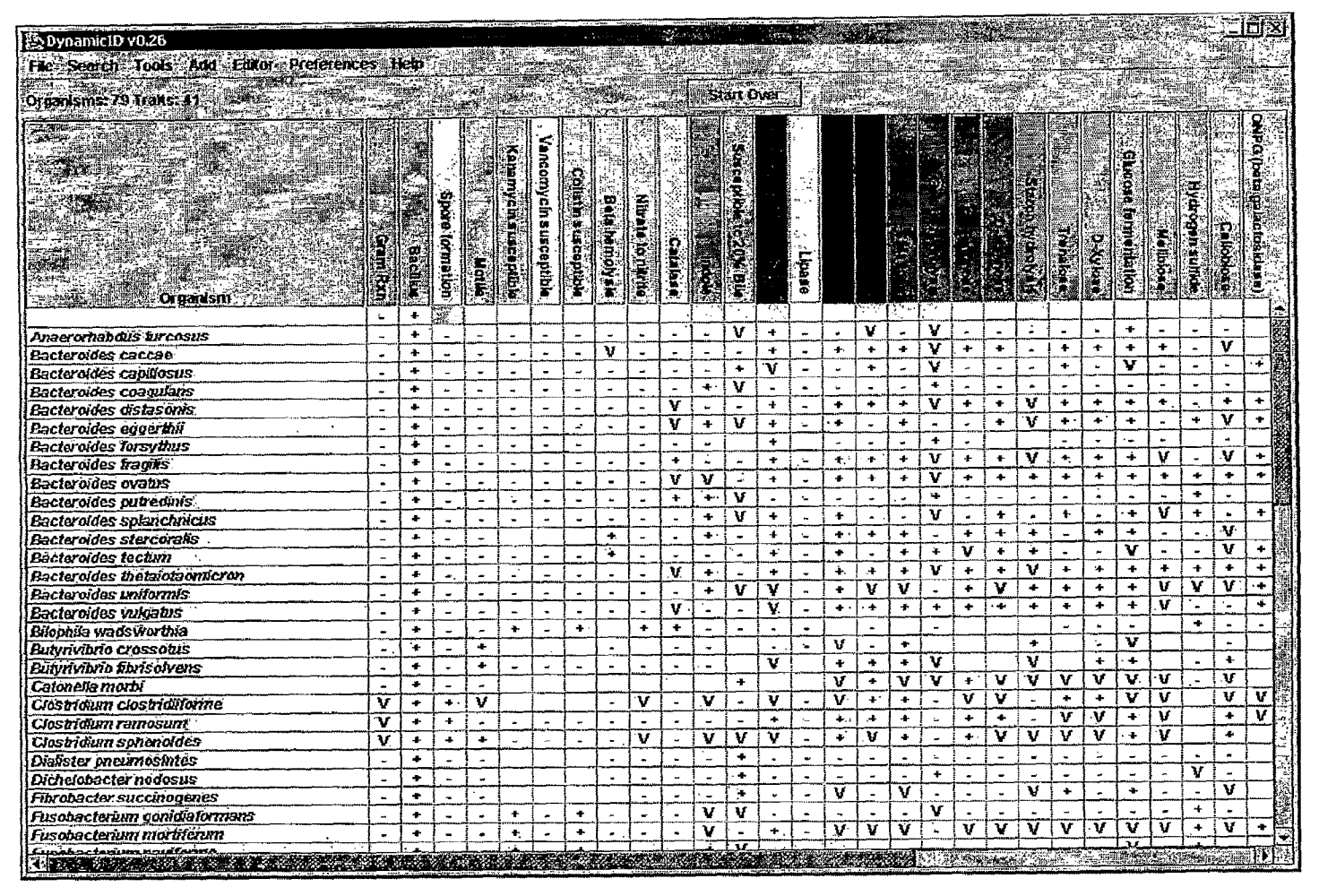
Figure 4:
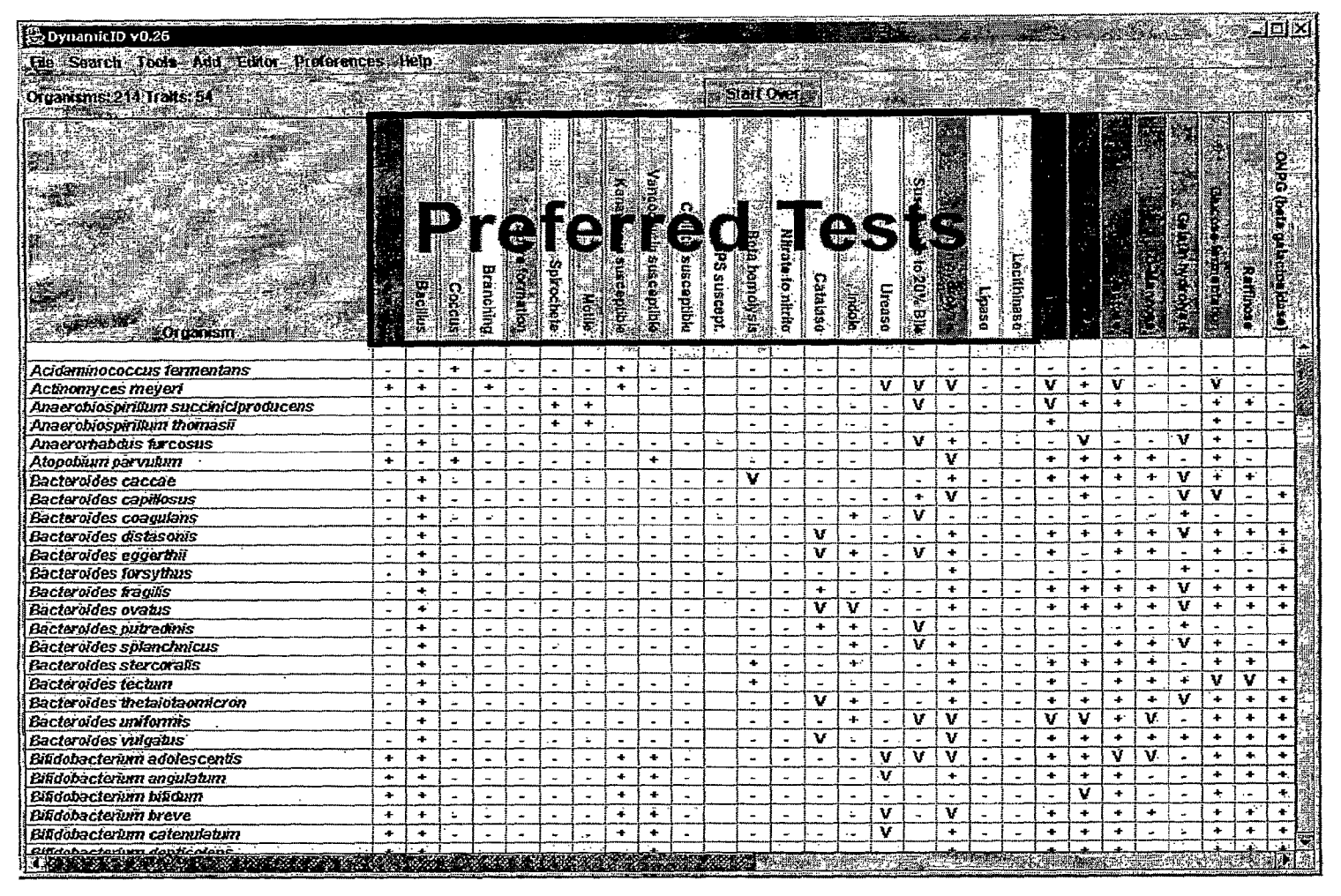

FIG. 3 is an example of a screen shot from the Knowledge Management System that displays various traits that were determined by indicator tests listed along the top row of columns and the various organisms listed in the first left hand column. FIG. 4 is an example of a screen shot from the Knowledge Management System that displays a Preferred Test which groups only a particular subset of traits. FIG. 5 is an example of a screen shot from the Knowledge Management System that displays appropriate information for the bacteria *Bilophila wadsworthia*. Such information may include habitat, growth rate, identification, where it is normally associated or found, information from in vitro, in vivo, and molecular studies, subgroups or strains, growth conditions, diameter, form, elevation, margin, color, density, general information, colony morphology, cellular morphology, references, photos of gram stain, photos of blood plates, and photos of BBE/LKV plates.

The Knowledge Management System houses appropriate information for each bacterial species. Appropriate information may be collected from scientific literature and may consist of information regarding bacteria growth on various substrates, bacteria sensitivity to a condition and/or bacteria production of metabolites. Such traits may also be assayed for by indicator tests. By way of example, such traits may include growth, reactions or production from: acetic acid major metabolic product, acetic acid minor metabolic product, ADH, ALP, alpha-fucosidase, alpha-galactosidase, alpha-glucosidase, arabinose, ArgA, *bacillus*, beta-galactosidase, beta-glucosidase, beta-glucuronidase, beta-NAG, beta-xylosidase, box car shape, butyric acid major metabolic product, butyric acid minor metabolic product, CAMP, caproic acid major metabolic product, catalase, cellobiose, chartreuse fluorescence, chymotrypsin, $CO_2$ growth, coccus, desulfoviridin, double zone beta-hemolysis, esculin hydrolysis, F/F required, fructose, gelatin hydrolysis, glucose, glycogen, gram reaction, growth in bile, HisA, I-arabinose, indole, isobutyric acid major metabolic product, isobutyric acid minor metabolic product, isocapronic acid major metabolic product, isocapronic acid minor metabolic product, isovaleric acid major metabolic product, isovaleric acid minor metabolic product, lactate converted to propionate, lactic acid major metabolic product, lactic acid minor metabolic product, lactose, leithinase, LeuA, lipase, maltose, mannitol, mannose, melezitose, melibiose, milk clot formed, milk digested, motile, N-Acetyl-beta-gulcosaminidase, nitrate, ONPG (Beta-galactosidase), oxygen tolerance, PheA, phenylaceric acid minor metabolic product, pigment, pitting of agar, ProA, propionic acid major metabolic product, PyrA, raffinose, red fluorescence, reverse CAMP test, rhamnose, ribose, salicin, sensitive to colistin, sensitive to kanamycin, sensitive to SPS, sensitive to vancomycin, sorbitol, spore former, starch hydrolysis, strictly anaerobic, subterminal spore location, succinic acid major metabolic product, succinic acid minor metabolic product, sucrose, terminal spore location, threonine converted to propionate, trehalose, trypsin, TyrA, urease, valeric acid major metabolic product, valeric acid minor metabolic product, xylan, and xylose. Bacterial response may include positive, negative, or no response. Bacterial response may also be measured by smell, color, growth, non-growth, death, symbiosis and non-symbiosis.

The Knowledge Management System software also includes statistical modeling programs which aid in identifying an optimal biomass for anaerobic bacterial hydrogen production. Such methods include Hidden Markov Models, phylogenetic inferences which include clustering methods such as (UPGMA) Unweighted Pair Group Methods using Arithmetic averages, distance and parsimony methods, maximum likelihood estimation and Chomsky hierarchy. For example, given a set of growth conditions by which indicator tests have been performed to identify traits of bacteria, use of probabilistic modeling may infer whether using different growth conditions deter or optimize production of hydrogen. Also use of phylogenetic trees may aid to infer relationships between bacterial species and assist in determining for example the likelihood of whether certain unperformed indicator tests will result in either similar or dissimilar results compared to that of a related bacteria species.

Also provided are systems that automate the optimal biomass detection process for particular bacterial genera and species using a computer programmed for identifying positive and negative results based upon the methods provided herein. The methods herein can be implemented, for example, by use of the following computer systems and using the following calculations, systems and methods. An exemplary automated testing system includes various identification workstation that includes analytical instruments, such as a CCD camera or a microscope or other instruments for capturing the image of a bacterial sample or instruments that can measure bacterial physiological changes, and a computer for data analysis which is capable of communicating with the analytical instrument.

In an exemplary embodiment, the computer is a desktop computer system, such as a computer that operates under control of the "Microsoft Windows: operation system of Microsoft Corporation or the "Macintosh" operating system of Apple Computer, Inc., that communicates with the instrument using a known communication standard such as a USB, parallel or serial interface.

Figure 6:
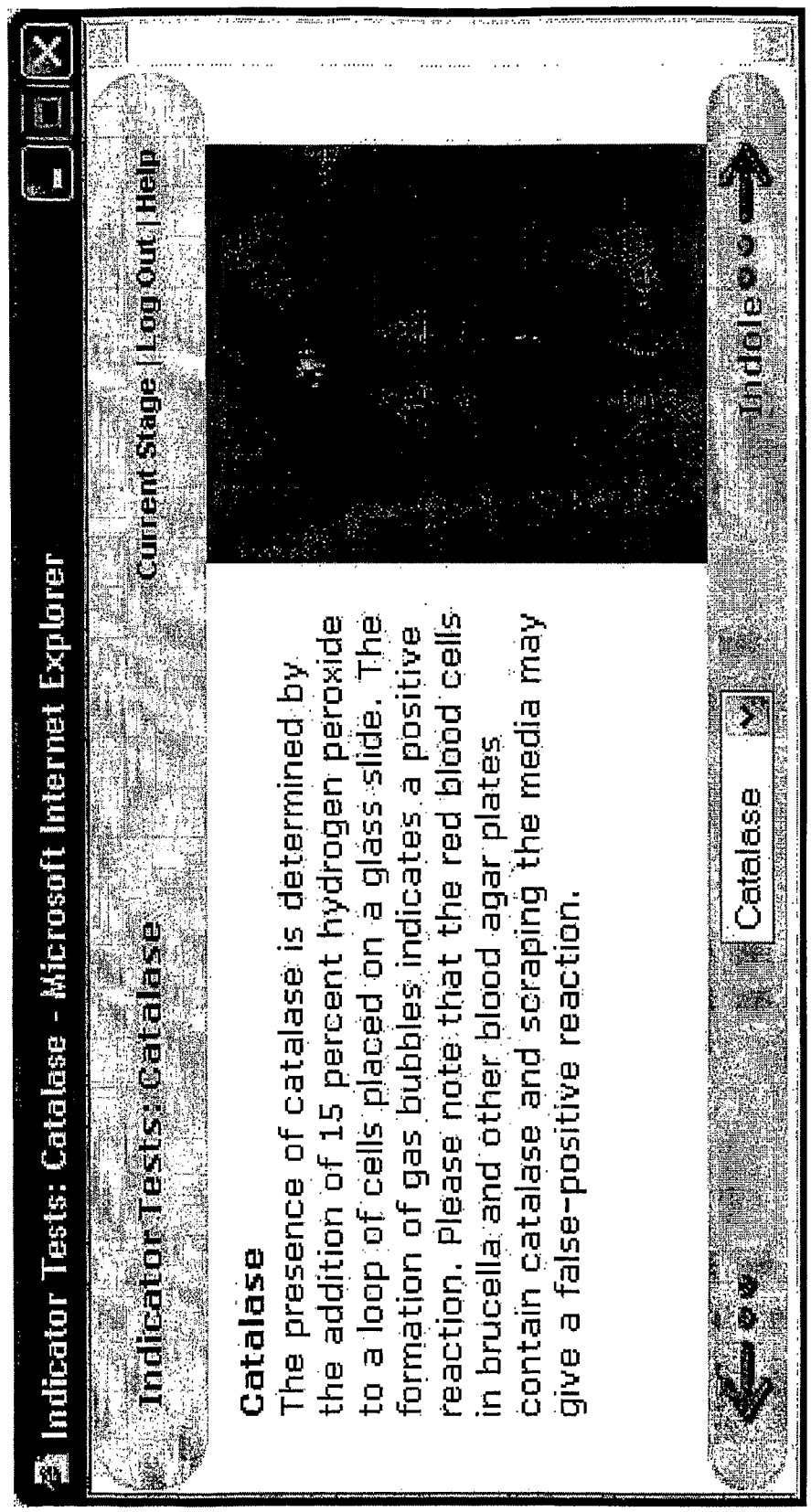
FIG. 6 presents one potential screen shot of a display page from the Knowledge Management System detailing a description of a catalase indicator test.

For example, systems for analysis of bacterial samples are provided. The system includes a processing station that performs the various indicator tests. For example, the system may include a processing station that performs the nitrate indicator test and a catalase indicator test. The nitrate indicator test determines an organism's ability to reduce nitrate to nitrite. A nitrate disk is placed on the plate at the time of inoculation. After 24-48 hours, reagents A (Sulfanilic acid dissolved in glacial acetic acid) and B (1,6-Cleve's acid dissolved in glacial acetic acid) are added and a positive test is indicated by a bright magenta color. If no color is seen within a few minutes, zinc dust is added to make sure the nitrate has not reduced beyond nitrite. Zinc dust, too, reduces nitrate to nitrite. Magenta coloration at this point is interpreted as a negative result because it indicates that the nitrate was not previously reduced by the organism. No color change after the addition of zinc is a positive result, because the organism reduced the nitrate beyond nitrite. The catalase indicator test, an example of which is shown in FIG. 6, is when the presence of catalase is determined by the addition of 15 percent hydrogen peroxide to a loop of cells placed on a glass slide. The formation of gas bubbles indicates a positive reaction. The red blood cells in *brucella* and other blood agar plates contain catalase and scraping the media may give a false-positive reaction.

The system may also include a spectral analysis system that analyzes the bacterial color changes from a CCD camera which processes results from a nitrate indicator test or a gas formation analysis system that analyzes formation of gas by bacteria from a CCD camera which processes results from a catalase indicator test; and a complete data analysis system, such as a computer programmed to identify which biomass is optimal for a particular bacteria to produce hydrogen anaerobically. The system can also include a control system that determines when processing at each station is complete and, in response, moves the sample to the next test station, and continuously processes samples one after another until the control system receives a stop instruction.

Figure 7:
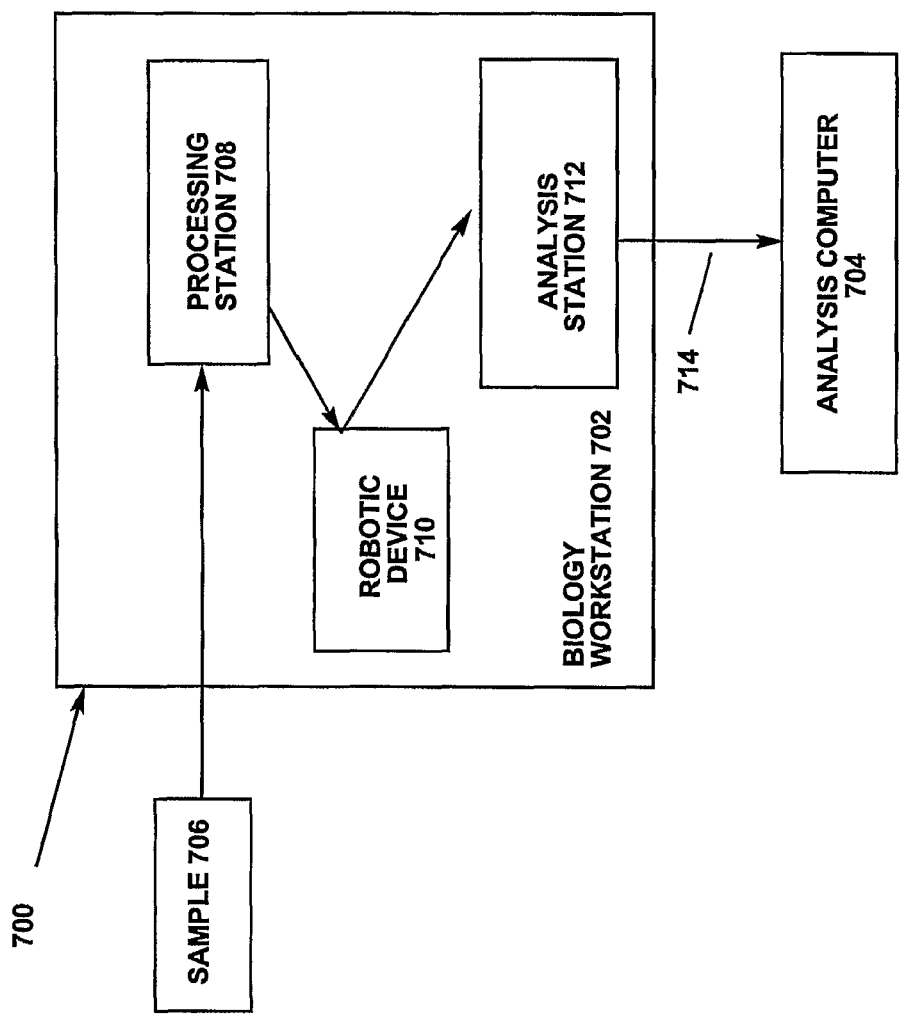
FIG. 7 presents one potential bock diagram of a system in the Knowledge Management System that performs sample processing and analysis in a biological workstation.

FIG. 7 is an example of a block diagram of a system that performs sample processing and biological workstation 702 and an analysis computer 740. At the biological workstation, one or more samples 706 are received and prepared for analysis at a sample processing station 708, where the above-described indicator tests can take place. The samples are then moved to an analysis station 712, where analysis of the bacteria such as spectral or gas formation analysis can be processed and recorded. The samples are moved from the processing station 708 to the analysis station 712 by either a computer-controlled robotic device 710 or by manual processing, not shown.

The robotic device can include subsystems that ensure movement between all of the stations that preserve the integrity of the samples 706 and ensure valid test results. The subsystems can include, for example, a mechanical lifting device or arm that can pick up a sample from the sample processing station 708 and then move to and deposit the processed sample for analysis at the analysis station 712.

The analysis station 712 produces data that identifies and quantifies the positive and negative results of the indicator tests of the sample 706 being measured. Those skilled in the art will be familiar with the biological monitoring systems, such as microscopes, that can be used to identify positive or negative bacterial reactions or a CCD camera, which can be used to image the results. The data is provided from the analysis station 712 to the analysis computer 704, either by manual entry of measurements results into the analysis computer or by communication between the analysis station and the analysis computer. For example, the analysis station 712 and the analysis computer 704 can be interconnected over a network 714 such that the data produced by the analysis station can be obtained by the analysis computer. The network 714 can comprise a local area network (LAN), or a wireless communication channel, or any other communications channel that is suitable for computer-to-computer data exchange.

The processing function of the analysis computer 704 and the control function of the biology workstation 702 can be incorporated into a single computer device, if desired. In that configuration, for example, a single general purpose computer can be used to control the robotic device, not shown, and to perform the data processing of the data analysis computer 704. Similarly, the operations of the analysis station 712, the sample processing operations of the sample processing station 708, or the other additional stations, not shown, can be performed under the control of a single computer.

Thus, the processing and analysis functions of the stations and computer 708, 712, and 704 can be performed by a variety of computing devices, if the computing devices have a suitable interface to any appropriate subsystems (such as a mechanical arm of the robotic device, not shown) and have suitable processing power to control the systems and perform the data processing.

The data analysis computer 704 can be part of the analytical instrument or another system component or it can be at a remote location. The computer system can communicate with the instrument, for example, through a wide area network or local area communication network or other suitable communication network. The system with the computer is programmed to automatically carry out steps of the methods herein and the requisite calculations. For embodiments that use color changing patterns (for a reference) based on the indicator test used in the processing station, a user enters the spectral identification for the bacteria sample. These data can be directly entered by the user from a keyboard of from other computers or computer systems linked by network connection, or on removable storage medium such as a data CD, minidisk (MD), DVD, floppy disk, jump disk or other suitable storage medium. Next, the user initiates execution software that operates the system in which the spectral identification is constructed for the bacteria imaged.

Figure 8:
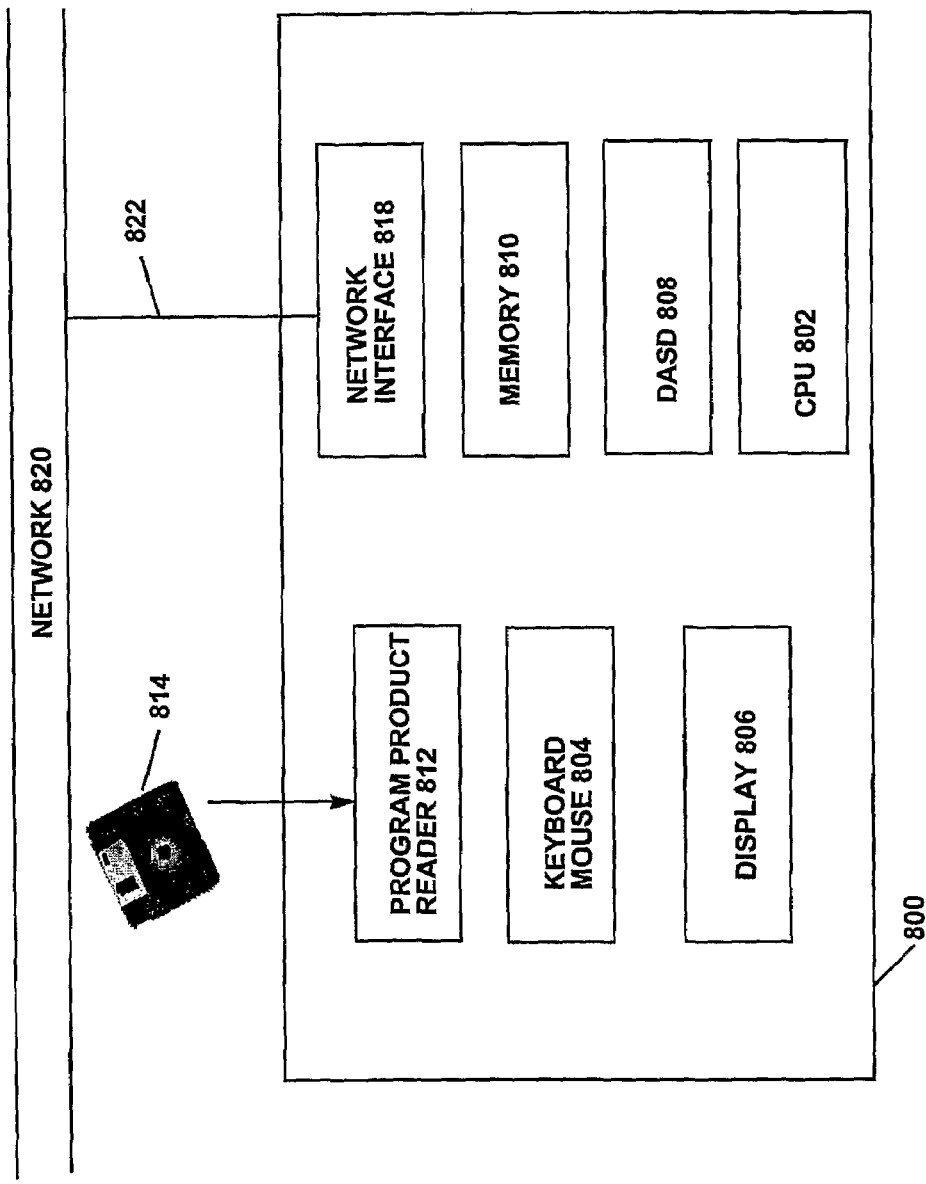
FIG. 8 presents one potential block diagram of a computer in the Knowledge Management System, illustrating the hardware components included in a computer that can provide the functionality of workstations and computers.

FIG. 8 is a block diagram of a computer in the system 800 of FIG. 7, illustrating the hardware components included in a computer that can provide the functionality of the stations and computers 708, 712, and 704. Those skilled in the art will appreciate that the stations and computers illustrated in FIG. 7 can all have a similar computer construction, or can have alternative constructions consistent with the capabilities and respective functions described herein. The FIG. 8 construction is especially suited for the data analysis computer 704 illustrated in FIG. 7.

FIG. 8 displays an exemplary computer 800 such as might comprise a computer that controls the operation of any of the stations and analysis computers 708, 712, and 704. Each computer 800 operates under control of a central processor unit (CPU) 802, such as a "Pentium" microprocessor and associated integrated circuit chips, available from Intel Corporation of Santa Clara, Calif., USA. A computer user can input commands and data from a keyboard and computer mouse 804, and can view inputs and computer outputs at a display 806. The display is typically a video monitor or flat panel display. The computer 800 also includes a direct access storage device (DASD) 808, such as a hard disk drive. The computer includes a memory 810 that typically comprises volatile semiconductor random access memory (RAM). Each computer includes a program product reader 812 that accepts a program product storage device 814, from which the program product reader can read data (and to which it can optionally write data). The program product reader can comprise, for example, a disk drive, and the program product storage device can comprise removable storage media such as a magnetic floppy disk, a CD-R disc, a CD-RW disc, or DVD disc.

Each computer 800 can communicate with the other FIG. 7 systems over a computer network 820 (such as, for example, the local network 714 or the Internet or an intranet) through a network interface 818 that enables communication over a connection 822 between the network 820 and the computer. The network interface 818 typically comprises, for example, a Network Interface Card (NIC) that permits communication over a variety of networks, along with associated network access subsystems, such as a modem.

The CPU 802 operates under control of programming instructions that are temporarily stored in the memory 810 of the computer 800. When the programming instructions are executed, the computer performs its functions. Thus, the programming instructions implement the functionality of the respective workstation or processor. The programming instructions can be received from the DASD 808, through the program product storage device 814, or through the network connection 822. The program product storage drive 812 can receive a program product 814, read programming instructions recorded thereon, and transfer the programming instructions into the memory 810 for execution by the CPU 802. As notes above, the program product storage device can comprise any one of multiple removable media having recorded computer-readable instructions, including magnetic floppy disks and CD-ROM storage discs. Other suitable program product storage devices can include magnetic tape and semiconductor memory chips. In this way, the processing instructions necessary for operation in accordance with the methods and disclosure herein can be embodied on a program product.

Alternatively, the program instructions can be received into the operating memory 810 over the network 820. In the network method, the computer 800 receives data including program instructions into the memory 810 through the network interface 818 after network communication has been established over the network connection 822 by well-known methods that will be understood by those skilled in the art without further explanation. The program instructions are then executed by the CPU 802 thereby comprising a computer process.

It should be understood that all the stations and computers of the system 700 illustrated in FIG. 7 can have a construction similar to that shown in FIG. 8, so that details described with respect to the FIG. 8 computer 800 will be understood to apply to all computers of the system 700. It should be appreciated that any of the communicating stations and computers can have an alternative construction, so long as they can communicate with the other communicating stations and computers illustrated in FIG. 7 and can support the functionality described herein. For example, if a workstation is unable to receive program instructions from a program product device, then it is not necessary for that workstation to include that capability, and that workstation will not have the elements depicted in FIG. 8 that are associated with that capability.

Bacteria Selection, Modification and Maximization

The various species of bacteria and various forms of biomass described herein may be used in all aspects of anaerobic production of hydrogen and other chemical products presented herein. For example, the various species of bacteria may be used in the anaerobic fermentation apparatuses described herein, using any form of biomass presented as a food source.

In contrast to known anaerobic methods, which generate hydrogen from mixed bacteria cultures obtained from soil or other samples, the methods described herein produces hydrogen using specific isolated anaerobic bacteria strains, chosen for the ability of particular strains to utilize specific biomass/ nutrients as food sources. The approach is to isolate and culture specific bacterial strains which are high hydrogen producers for particular biomass. By way of example only, a particular bacteria strain may yield large quantities of hydrogen from cellulosic material, whereas a different isolated strain may yield large quantities of hydrogen from sewage. Thus, selection and isolation of specific bacterial strains with enhanced fermentation properties for specific biomass allows for optimization of hydrogen production as the type of substrate available varies.

The Winogradsky column can be used to demonstrate the metabolic diversity of prokaryotes, and how the activities of different microorganisms enable other organisms to grow in an interdependent or symbiotic manner. In addition, the column demonstrates how elements, such as sulphur, nitrogen, carbon and other elements are cycled in natural environments. These columns are complete, self-contained recycling systems, driven only by energy from light. All life on earth can be categorized in terms of the organism's carbon and energy source. Energy can be obtained from light reactions (phototrophs) or from chemical oxidations of organic or inorganic substances (chemotrophs); the carbon for cellular synthesis can be obtained from $CO_2$ (autotrophs) or from preformed organic compounds (heterotrophs). Combining these categories, we get the four basic life strategies: photoautotrophs (e.g. plants), chemoheterotrophs (e.g. animals, fungi), photoheterotrophs and chemoautotrophs. Only in the bacteria do we find all four basic life strategies. The prokaryotic bacteria and archaea exhibit an astonishing metabolic diversity, which far exceeds that of animals, plants, fungi and other higher organisms, and Winogradsky columns also demonstrate how microorganisms occupy highly specific microsites according to their environmental tolerances and their carbon and energy requirements.

A typical Winogradsky column is usually a glass or plastic tube, about 30 cm tall and 5 cm diameter. Mud from the bottom of a lake or river, supplemented with cellulose (e.g. newspaper), sodium sulphate and calcium carbonate, is then added to the lower one-third of the tube, and the remainder of the tube is filled with water from the lake or river. The tube is then capped (not sealed), allowing air flow to the top of the water column, and placed near a window with supplementary strip lights. All the organisms are present initially in low numbers, but after incubation for 2 to 3 weeks the different types of microorganisms proliferate and occupy distinct zones where the environmental conditions favor their specific activities. The large amount of cellulose added initially promotes rapid microbial growth which soon depletes the oxygen in the sediment and in the water column. Only the very top of the column remains aerated because oxygen diffuses very slowly through water from the capped tube opening. The only organisms that can grow in the anaerobic conditions are those that ferment organic matter and those that perform anaerobic respiration. For example, Clostridium species are strictly anaerobic and start to grow when the oxygen is depleted in the sediment. Cellulose-degrading *Clostridium* species degrade the cellulose to glucose and then ferment the glucose producing a range of simple organic compounds (e.g. acetic acid), carbon dioxide, and hydrogen as the fermentation end products. Sulphur-reducing bacteria, such as *Desulfovibrio*, utilize these fermentation products by anaerobic respiration, using either sulphate or other partly oxidised forms of sulphur (e.g. thiosulphate) as the terminal electron acceptor, generating large amounts of $H_2S$ by this process. The $H_2S$ can react with any iron in the sediment, producing black ferrous sulphide, and some of the $H_2S$ diffuses upwards into the water column, where it is utilized by other organisms. The diffusion of $H_2S$ from the sediment into the water column enables anaerobic photosynthetic bacteria to grow, resulting in a zone of green sulphur bacteria immediately above the sediment, followed by a zone of purple sulphur bacteria. The green and purple sulphur bacteria gain energy from light reactions and produce their cellular materials from $CO_2$ in much the same way as plants do. However, $H_2S$ is used as the reductant instead of water and rather than generate oxygen during photosynthesis elemental sulphur is formed. The purple sulphur bacteria (e.g. *Thiocapsa*) typically have large cells and they deposit sulphur granules inside the cells, whereas green sulphur bacteria have smaller cells and typically deposit sulphur externally. Note that the sulphur (or sulphate formed from it) produced by these photosynthetic bacteria returns to the sediment where it can be recycled by *Desulfovibrio* as part of the sulphur cycle in natural waters. Most of the water column above the photosynthetic bacteria is coloured bright red by a large population of purple non-sulphur bacteria. These include species of *Rhodopseudomonas, Rhodospirillum* and *Rhodomicrobium*. These bacteria are photoheterotrophs, as they grow in anaerobic conditions, gaining their energy from light reactions but using volatile organic acids (e.g. acetic acid) as their carbon source for cellular synthesis. The volatile organic acids that they use are the fermentation products of other anaerobic bacteria (e.g. *Clostridium* species), but the purple non-sulphur bacteria are intolerant of high $H_2S$ concentrations, so they occur above the zone where the green and purple sulphur bacteria are found. Nearer the top of the water column the purple non-sulphur bacteria disappear due to the oxygenated water. A variety of microorganisms can grow in the oxygenated zone at the top of the water column; in particular sulphur-oxidising bacteria, and cyanobacteria. Any $H_2S$ that diffuses into the aerobic zone can be oxidized to sulphate by sulphur-oxidising bacteria. These bacteria are chemosynthetic or chemoautotrophic organisms, since they gain energy from oxidation of $H_2S$, and they synthesize their own organic matter from $CO_2$. Similar types of organism occur in soils, gaining energy from the oxidation of ammonium to nitrate, which then leaches from the soil and can accumulate in water supplies. The photosynthetic cyanobacteria also grow in the aerobic zones, and are the only bacteria that have oxygen-evolving photosynthesis like that of plants. Once the cyanobacteria start to grow they oxygenate the water, which forces the anaerobic bacteria toward the bottom, thereby allowing the cyanobacteria and other aerobes to occupy a larger portion of the Winogradsky column.

The Winogradsky column is essentially a miniature ecosystem, wherein the metabolic diversity of bacteria allows for interdependent relationships to exist throughout the column. The fermentation products of one species are consumed by another, thereby cycling various elements, such as sulphur, nitrogen, and carbon, and maintaining the life cycle. Without manipulating the growth of one species over another, the Winogradsky column demonstrates how microorganisms occupy highly specific locations according to their environmental tolerances and their carbon and energy requirements. The initial food source is common throughout the initial sediment, and the variety of species required for the development of the "ecosystem" is initially present.

The apparatus, methods and processes for bacterial isolation and enrichment described herein include anaerobic bacteria isolation/enrichment systems designed to be ultimately anaerobic and to optimize growth of bacteria species depending on the food source provided. In this manner bacteria with optimal fermentation properties are selected out for maximum hydrogen production. In addition, the apparatus, methods and processes for bacterial isolation and enrichment described herein may also allow for the growth and isolation of anaerobic bacteria which utilize fermentation products of other species as food sources, thereby increasing hydrogen production. These features illustrate the difference between the apparatus, methods and processes for bacterial isolation and enrichment described herein, and a Winogradsky column.

Figure 9:
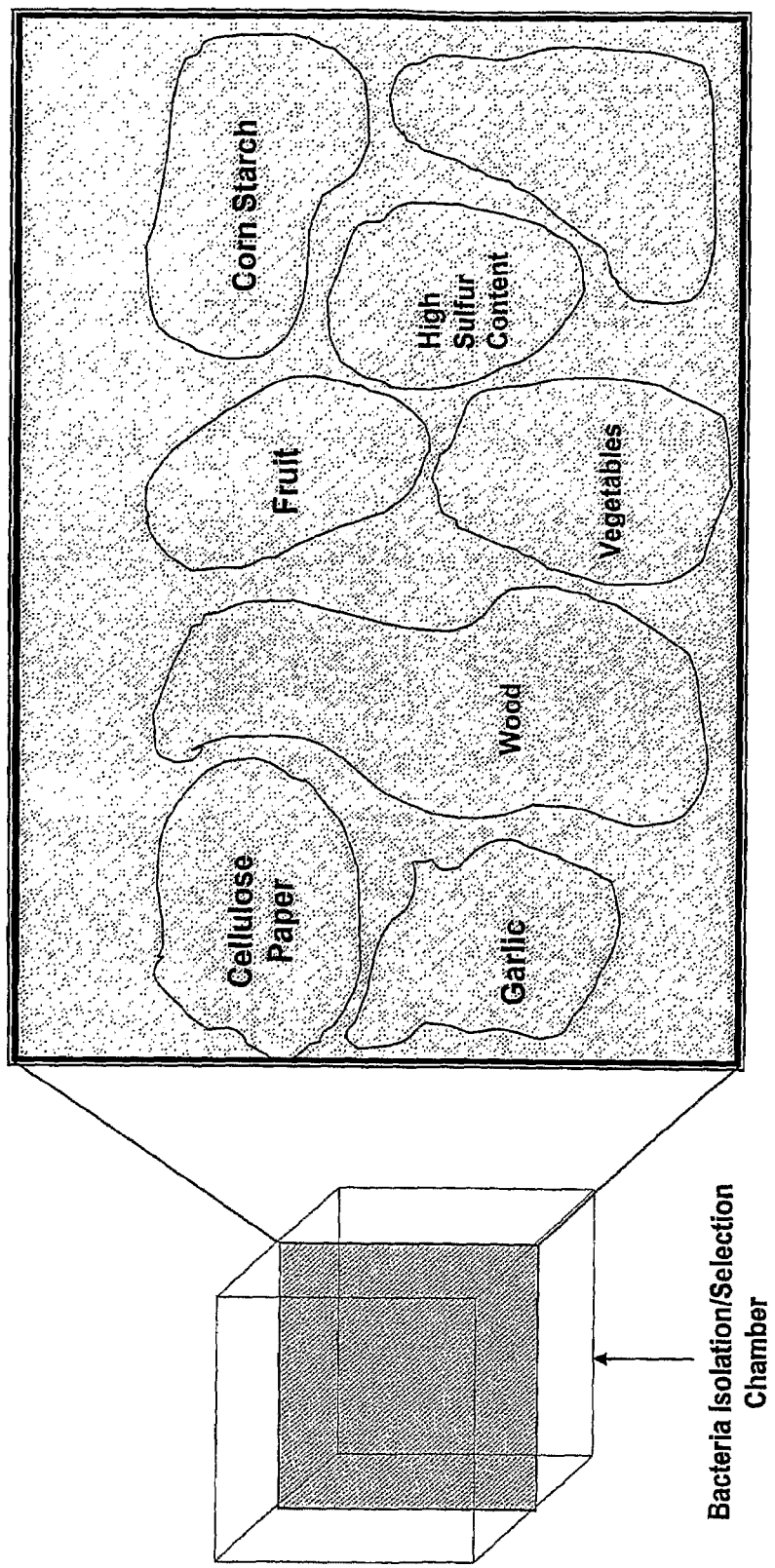
FIG. 9 presents one potential diagram of one embodiment of the isolation/enrichment system used to isolate anaerobic bacteria.

The isolation/enrichment system can take any shape, including, but not limited to, circular, cylindrical, spherical, square, or rectangular form, and may have a volume ranging from 100 cm$^3$ to 50,000 cm$^3$. One embodiment of the anaerobic bacteria isolation/enrichment system described herein is shown in FIG. 9. Here, the isolation/enrichment system resembles an ant farm or an aquarium, wherein two parallel glass plates with a spacer are sealed on three sides to create an open trough. The top of the trough may eventually be closed and sealed to ensure anaerobic conditions remain within the sealed chamber, although, venting systems may be used to prevent pressure build up due to gas evolution during fermentation.

Preparation of the anaerobe bacteria isolation/enrichment system involves obtaining various potential food sources, such as, by way of example only, vegetable materials, garlic material, shredded hay, grass clippings, shredded newspaper, sawdust, corn starch, oatmeal, and arranging these food sources at various locations throughout the isolation/enrichment. In addition, any of the biomass known in the art may also be used. The anaerobe bacteria isolation/enrichment system is filled with deoxygenated water, inoculated with a mixture of bacteria species, and the top is then sealed. The head space above the deoxygenated water is purged to remove any oxygen present. The mixture of bacteria species used in the anaerobe bacteria isolation/enrichment system may be obtained from cattle rumen, a sample of soil, sludge, an anaerobic bacteria culture, an aerobic bacteria culture, anaerobic sediments from fresh or brackish waters, sewage, animal feces, hydrothermal soils and pools, deep water hydrothermal vents or other potential source of anaerobic bacteria. The bacteria in the isolation/enrichment system may thrive on a particular food source as they continue to grow under anaerobic conditions. The bacteria isolated in this system may include, by way of example only, species such as *Abiotrophia defectiva, Acidaminococcus fermentans, Actinobaculum schalii, Actinomyces europaeus, Actinomyces funkei, Actinomyces georgiae, Actinomyces gerensceriae, Actinomyces graevenitzii, Actinomyces israelii, Actinomyces meyeri, Actinomyces naeslundi, Actinomyces neuii* species *anitratus, Actinomyces neuii* species *neuii, Actinomyces ondontolyticus, Actinomyces radicidentis, Actinomyces radingae, Actinomyces turicensis, Actinomyces urogenitalis, Actinomyces viscosis, Anaerorhabdus furcosa, Arcanobacterium bernardiae, Arcanobacterium hemolyticum, Arcanobacterium pyogenes, Atopobium minutum, Atopobium parvulum, Atopobium rimae, Atopobium vaginae, Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredenis, Bacteroides pyogenes, Bacteroides splanchnicus, Bacteroides stercoris, Bacteroides tectus, Bacteroides thetaiotaomicron, Bacteroides uniformis, Bacteroides ureolyticus, Bacteroides vulgatus, Bifidobacterium adolescentis, Bifidobacterium angulatum, Bifidobacterium bifidum, Bifidobacterium breve, Bifidobacterium catenulatum, Bifidobacterium denticolens, Bifidobacterium dentium, Bifidobacterium infantis, Bifidobacterium inopinatum, Bifidobacterium longum, Bifidobacterium pseudocatenulatum, Bilophila wadsworthia, Bulleidia extcructa, Campylobacter gracilis, Campylobacter hominis, Campylobacter rectus, Campylobacter showae, Capnocytophaga granulosa, Capnocytophaga haemolytica, Clostridium argentinense, Clostridium baratii, Clostridium bifermentans, Clostridium botulinum* types A B F, *Clostridium botulinum* types B E F, *Clostridium botulinum* types C D, *Clostridium butyricum, Clostridium cadaveris, Clostridium carnis, Clostridium clostridioforme, Clostridium difficle, Clostridium glycolicurn, Clostridium hastiforme, Clostridium histolyticum, Clostridium indolis, Clostridium innocuum, Clostridium limosum, Clostridium malenominaturn, Clostridium novyi* type A, *Clostridium paraputrificum, Clostridium perfringens, Clostridium piliforme, Clostridium putrificurn, Clostridium rarnosurn, Clostridium septicum, Clostridium sordellii, Clostridium sphenoides, Clostridium sporogenes, Clostridium subterminale, Clostridium symbiosum, Clostridium tertium, Clostridium tetani, Collinsella aerofaciens, Corynebacterium matruchotii, Cryptobacterium curturn, Desulfomonas pirgra, Dialister pneumosintes, Eggerthella lenta, Eikenella corrodens, Eubacteria sulci, Eubacteria tenue, Eubacterium combesii, Eubacterium contortum, Eubacterium cylindroides, Eubacterium infirmum, Eubacterium limosum, Eubacterium minutum, Eubacterium moniliforme, Eubacterium nodatum, Eubacterium rectale, Eubacterium saburreum, Eubacterium saphenurn, Eubacterium WALI, Eubacterium yurii, Filifactor alocis, Filifactor villosus, Finegoldia magna, Fusobacterium gonidiaformans, Fusobacterium mortiferum, Fusobacterium naviforme, Fusobacterium necrophorum, Fusobacterium nucleatum, Fusobacterium russii, Fusobacterium ulcerans, Fusobacterium varium, Gemella morbillorum, Granulicatella adiacens, Granulicatella elegans, Holdemaniafiliformis, Lactobacillus acidophillus, Lactobacillus brevis, Lactobacillus canteforme, Lactobacillus casei, Lactobacillus crispatus, Lactobacillus fermentum, Lactobacillus gasseri, Lactobacillus iners, Lactobacillus jensenii, Lactobacillus leichmannii, Lactobacillus oris, Lactobacillus paracasei subspecies paracasei, Lactobacillus paraplan-*

*tarum, Lactobacillus plantarum, Lactobacillus rhamnosus, Lactobacillus salivarius, Lactobacillus uli, Lactobacillus vaginalis, Leptotrichia buccalis, Leptotrichia sanguinegens, Megasphaera elsdenii, Micromonas micros, Mitsuokella multiacida, Mobiluncus curtisii* species *curtisii, Mobiluncus curtisii* species *holmesii, Mogibacterium pumilum, Mogibacterium timidum, Mogibacterium vescum, Peptococcus niger, Peptostreptococcus anaerobius, Peptostreptococcus asaccharolyticus, Peptosfeptococcus harei, Peptostreptococcus hydrogenalis, Peptostreptococcus indolyticus, Peptostreptococcus ivorii, Peptostreptococcus lacrimalis, Peptostreptococcus lactolyticus, Peptostreptococcus octavius, Peptostreptococcus prevotii, Peptostreptococcus prevotii/ tetradius, Peptostreptococcus tetradius, Peptostreptococcus trisimilis, Peptostreptococcus vaginallis, Porphyromonas assacharolytica, Porphyromonas cangingivalis, Porphyromonas canoris, Porphyromonas cansulci, Porphyromonas cantoniae, Porphyromonas circumdentaria, Porphyromonas crevioricanis, Porphyromonas endodontalis, Porphyromonas gingivalis, Porphyromonas gingivicanis, Porphyromonas gulae, Porphyromonas levii, Porphyromonas macacae, Prevotella albensis, Prevotella bivia, Prevotella brevis, Prevotella bryantii, Prevotella buccae, Prevotella buccalis, Prevotella corporis, Prevotella dentalis, Prevotella denticola, Prevotella disiens, Prevotella enoeca, Prevotella heparinolytica, Prevotella intermedia, Prevotella loescheii, Prevotella melanogenica, Prevotella nigrescens, Prevotella oralis, Prevotella oris, Prevotella oulorum, Prevotella pallens, Prevotella ruminicola, Prevotella tannerae, Prevotella veroralis, Prevotella zoogleoformans, Propionibacterium acnes, Propionibacterium avidum, Propionibacterium granulosum, Propionibacterium proionicus, Pseudoramibacter alactolyticus, Rothia dentocariosa, Ruminococcus hansenii, Ruminococcus productus, Slakia exigua, Slakia heliontrinireducens, Staphylococcus saccharolytics, Streptococcus anginosus, Streptococcus contellatus, Streptococcus pleomorphus, Streptococcus intermedius, Sutterella wadsworthensis, Tissierella praeacuta,* and *Veillonella* species, or genera containing such species.

The anaerobic bacteria isolation/enrichment system may be large, allowing for increased available space for different bacteria species which may utilize the same food source, and therefore minimizes competition between species. Thus, it may be possible to isolate various high volume hydrogen producing strains grown on a common food source and then further differentiate them by subdividing the food source into different categories. For instance, by way of example only, the isolation of high hydrogen producers grown on agricultural waste, and then subdividing the agriculture waste into specific crops, such as potatoes, tomatoes, garlic, cranberries, and the like. Once it is evident that a bacterial colony is specific for a particular biomass type, the bacteria are removed from the isolation/enrichment system, transferred for more controlled culture, grown, and the isolated bacteria species is harvested and stored for later use to inoculate and ferment a specific biomass in the digester. Removal of bacteria from the isolation/enrichment system may be done at any time period. By way of example only, bacteria may be removed after 1-7 days, or earlier, or after 1-20 weeks, or longer. Bacteria may be removed from the system by any means, for example, by use of a needle, syringe or vacuum.

Nutrient Selection and Preparation

The various species of bacteria and various forms of biomass described herein may be used in all aspects of anaerobic production of hydrogen and other, chemical products presented herein. For example, the various species of bacteria may be used in the anaerobic fermentation apparatuses described herein, using any form of biomass presented as a food source.

The methods described herein allows for the preparation of the biomass, which includes, but is not limited to, harvesting or protecting the biomass quickly before spoilage, sterilization (i.e. pasteurizing and/or acidifying), neutralization (i.e. ammonium hydroxide), removal of oxygen (deoxygenation), and concentration adjustments, detoxification, and/or pre-digestion, prior to fermentation by isolated anaerobic bacteria.

Harvesting or protecting the biomass before spoilage or a state whereby the biomass is useless is a pre-condition to optimize preparation of the biomass for bacterial consumption. This is to ensure optimal hydrogen production from a biomass. An example of harvesting or protecting biomass before spoilage is when biomass is harvested and used within a 24 hour period. An another example may include refrigeration of the biomass to prevent spoilage.

Pre-digestion includes the pre-treatment of biomass to get it into a condition for the bacteria to feed upon. By way of example only, pre-digestion may include addition of other insects, animals, enzymes, and/or solutions to modify the biomass prior to introducing it to the bacteria. For example, the breakdown of cellulose into glucose may be a pre-treatment/pre-digestion. Another example is the pre-treatment of manure into an anaerobic substrate feedstock for bacteria through use of an organism that breakdown bile/urea within the manure.

Figure 10:
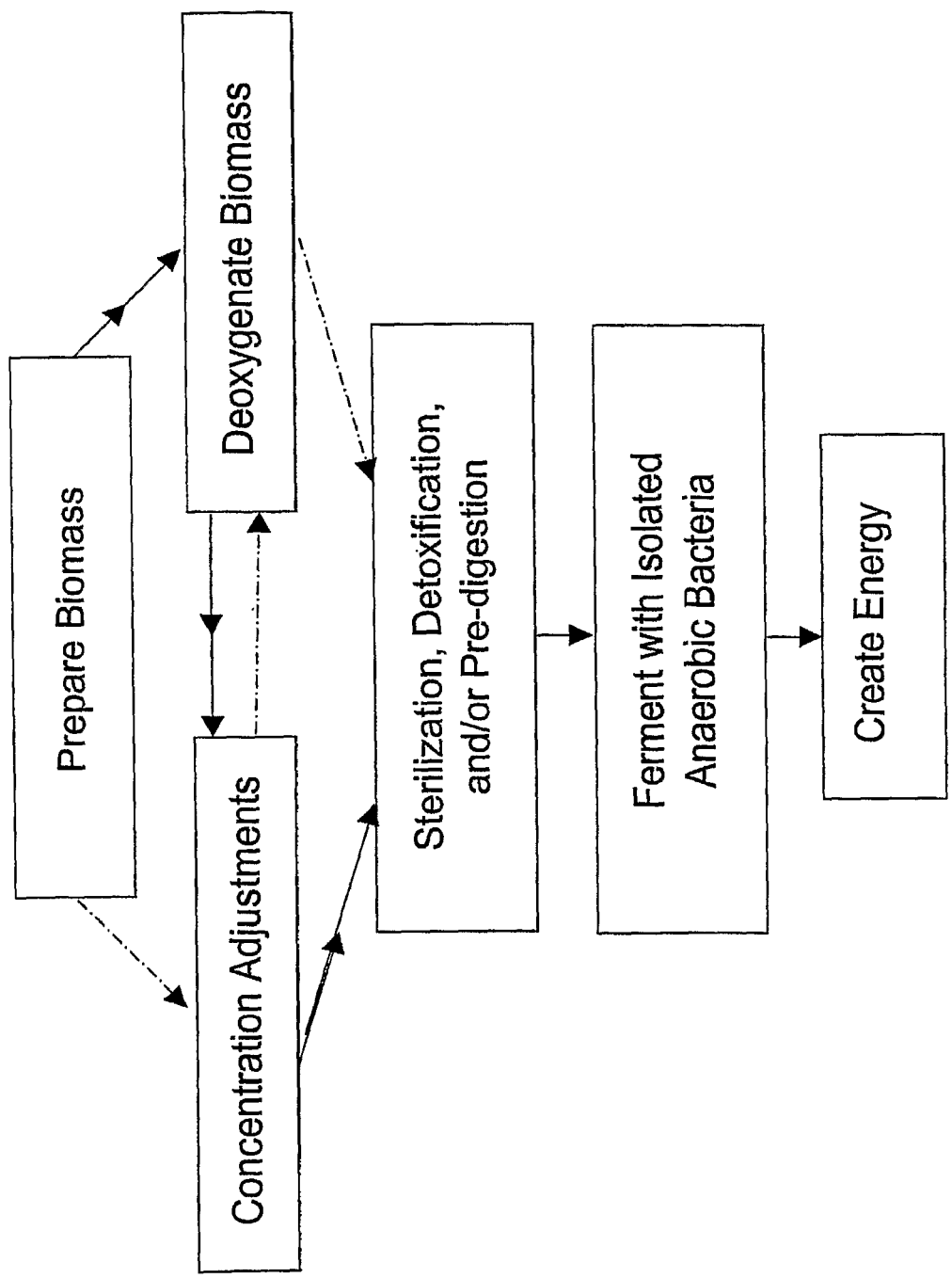
FIG. 10 presents one potential process flow diagram of a preferred embodiment of the anaerobic digester system.

The steps of sterilization, deoxygenation, concentration adjustments, detoxification, and/or pre-digestion may occur in a variety of orders such as deoxygenation of biomass first followed by concentration adjustments, sterilization, detoxification, and/or pre-digestion second or concentration adjustments, sterilization, detoxification, and/or pre-digestion first followed by deoxygenation of biomass second or all steps simultaneously or other combinations thereof. An example of a process flow diagram is shown in FIG. 10: double arrows display the order of deoxygenation of biomass before concentration adjustments, sterilization, detoxification, and/or pre-digestion and the singe arrow displays the order of concentration adjustments, sterilization, detoxification, and/or pre-digestion before deoxygenation of biomass.

After the concentration step, it may be necessary to adjust the concentration of the biomass depending on what is used. For example, fats or meats which have high protein content would be diluted to an approximate 5% sugar concentration equivalent before use. In addition, managing the proper rate at which the biomass is fed to the bacteria needs to be accounted. The dynamic feed rate should be balanced with the exponential growth rate of the bacteria as well as the rate of utilization. Oilier factors that should be monitored may include hydrogen production, pH levels and acid production.

Examples of biomass available for hydrogen production via "dark fermentation" include, but are not limited to, mash of starched materials derived from corn, wheat, oats, and other grain materials, beet molasses, blackstrap molasses, citrus molasses, invert sugar, sucrose, fructose, glucose, wood sugar, xylose, animal or fish tissue or parts, plant parts, fruits, sorghum, cheese whey, vegetables, plant processing waste, animal manure or urine, solids isolated from fermentation cultures, bovine manure, poultry manure, equine manure, porcine manure, bovine urine, poultry urine, equine urine, porcine urine, wood shavings or chips, slops, shredded paper, cotton burrs, grain, chaff, seed shells, hay, alfalfa, grass, leaves, sea shells, seed pods, corn shucks, weeds, aquatic plants, algae and fungus and combinations thereof.

Figure 11:
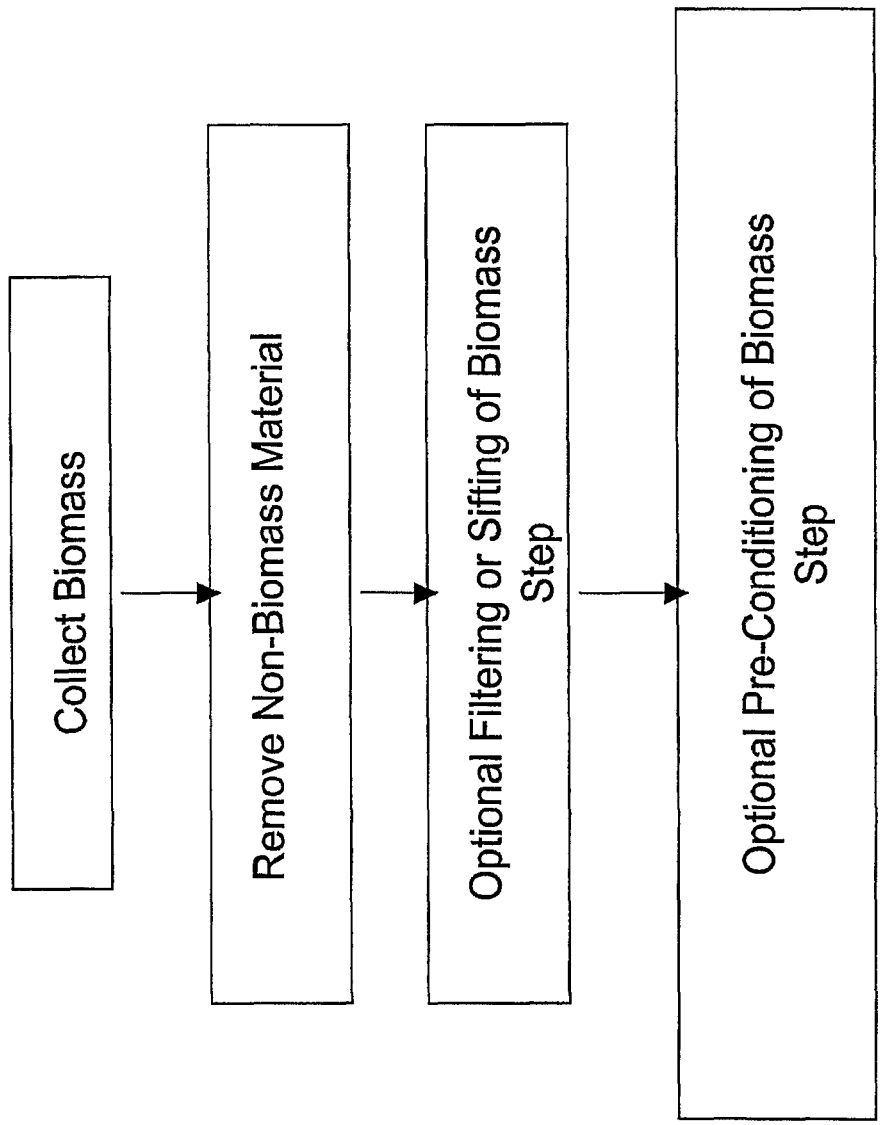
FIG. 11 presents one potential procedure to prepare biomass material.

FIG. 11 illustrates an example of the preparation of biomass for hydrogen production that may include but is not limited to the removal of non-biomass material, an optional filtering or sifting of biomass material step, an optional preconditioning of biomass material step or combinations thereof. Biomass material or feed stock is selectively chosen for optimal hydrogen production depending on the specific anaerobic bacteria used. Grit, such as dirt, sand, soil, stones, pebbles, rocks, feathers, hair and other such materials, may be removed prior to addition of the feed stock to the anaerobic digester; however, grit can be removed at any point along the process. Equipment such as clarifiers, settling tanks, multiphase tanks, and/or filters can be used to remove the grit.

Figure 12:
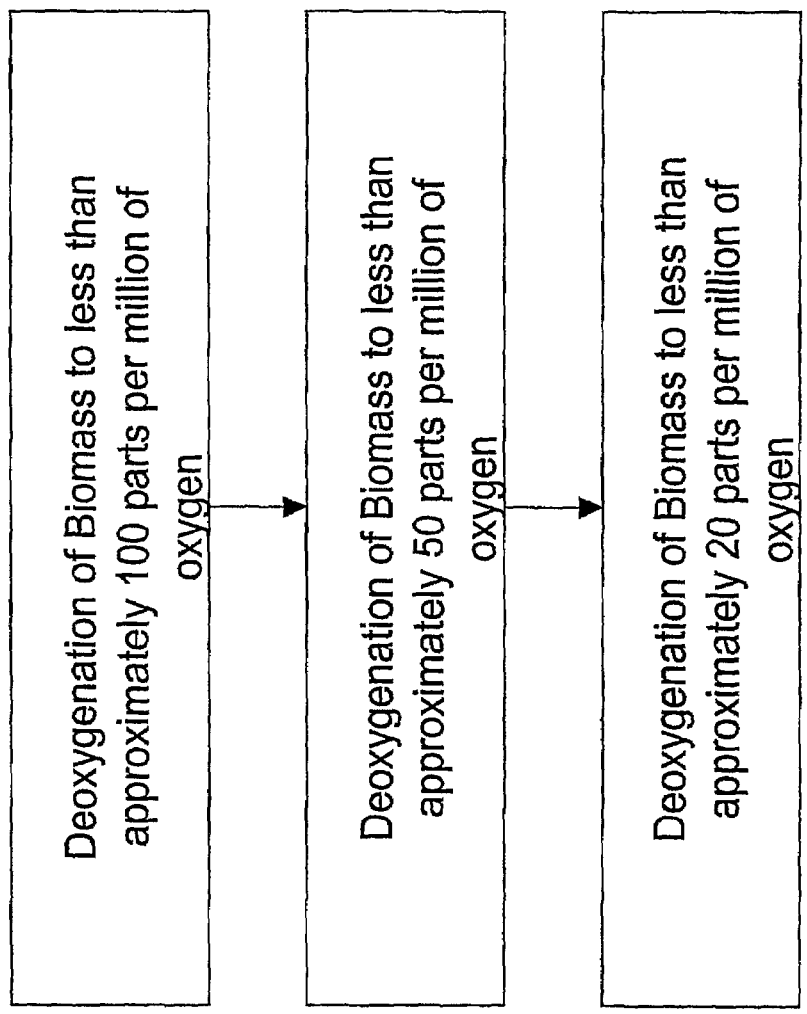
FIG. 12 presents one potential procedure to deoxygenate biomass.

Deoxygenation of the biomass prior to introduction to a digester, either as batch or continuous processes, ensures viability of the anaerobic bacteria which may die on exposure to oxygen. Oxygen exposure also inactivates the enzyme complex required for hydrogen production. Also, for continuous fermentation systems it minimizes oxygen introduction and limits the need to continuously purge the digester. FIG. 12 shows an example of a process flow diagram of the deoxygenation of biomass material. Deoxygenation of biomass material can include but are not limited to a single deoxygenation step or optional multiple deoxygenation steps of biomass material. Deoxygenation of biomass material can include but are not limited to using pressurized steam, oxygen free gas sparging, autoclaving, a reducing agent (such as by way of example only, dithiothreitol, cysteine, thioglycollate, or sodium sulfide), or combinations thereof. The use of pressurized steam also serves to thoroughly sterilize the media and simultaneously convert any complex carbohydrates into a form more easily acted upon by the bacteria.

Figure 13:
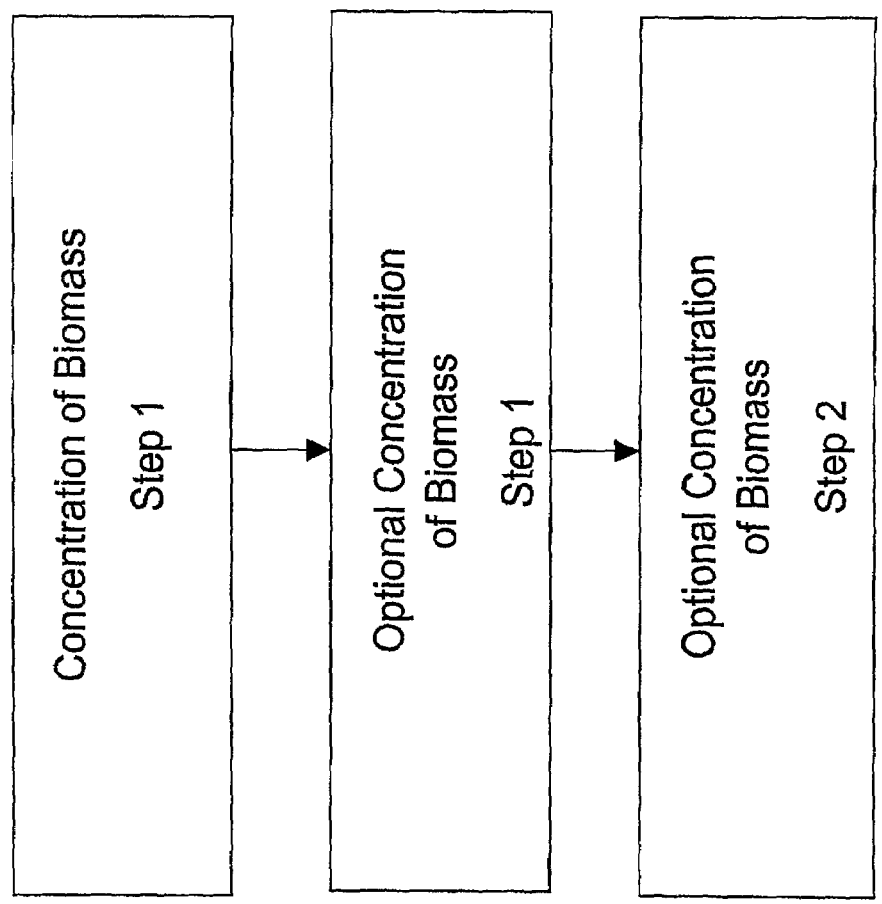
FIG. 13 presents one potential procedure to concentrate biomass.

The biomass concentration may have an effect on the bacteria metabolic pathways, which may affect the yield of hydrogen. However, concentrating the biomass prior to introduction to a digester, either as batch or continuous processes in combination with efficient removal of fermentation products, such as hydrogen, carbon dioxide and volatile organic acids, and control of the fermentation media pH increases the yield of hydrogen per unit volume of the digester. FIG. 13 is an example of a process flow diagram of the concentration of biomass material. Concentration of biomass material or optional steps of concentration of biomass material can include, but are not limited to, centrifugation, reverse osmosis, filtering, boiling, removal of liquids, lyophilization, other methods known in the art of condensing material into a solid or semi-solid form or combinations thereof.

Fermentation Products

Some anaerobic fermentation end products are beneficial to humans and are the basis of a number of industries, such as alternative energy, brewing industry, and the dairy industry. Examples of microorganisms and fermentation end products include, but are not limited to: *Streptococcus*, which produce lactate, formate, ethanol, and acetate when grown under anaerobic conditions; *Propionibacterium*, produce propionic acid acetic acid, and $CO_2$ by fermentation of glucose; *Escherichia coli* species can anaerobically produce acetic acid, lactic acid, succinic acid, ethanol, $CO_2$, and $H_2$; *Enterobacter* species can anerobically produce formic acid, ethanol, 2,3-butanediol, lactic acid, $CO_2$, and $H_2$; and *Clostridium* species can anerobically produce butyric acid, butanol, acetate, acetone, isopropyl alcohol, $CO_2$, and $H_2$.

To obtain alternative energy sources such as hydrogen from anaerobic fermentation, it is evident that various bacteria, such as, *Escherichia coli*, *Enterobacter* and *Clostridia*, are active hydrogen producers under anaerobic conditions. *Clostridia* are able to ferment various types of biomass into hydrogen, carbon dioxide, and a variety of organic compounds. For instance, during fermentation of sugars, hydrogen, carbon dioxide and volatile organic acids, such as butyrate and acetate, are produced, whereas, during the fermentation of amino acids and fatty acids, a variety of foul smelling compounds' are formed. *Clostridia* also produce extracellular enzymes to degrade large biological molecules in the environment into fermentable components. Hence, *Clostridia* play an important role in nature in biodegradation and many other nutrient cycles.

Members of genus *Clostridia* are ubiquitous in nature and may be found in soil and in the gastrointestinal tracts of animals and humans. *Clostridia* are Gram-positive, spore-forming, mostly motile, rod shaped anaerobic bacteria. A Gram-stain is a good method for differentiating *Clostridium* from other genera, as the cell incorporates the dye while the spore remains unstained. Most *Clostridium* species are strictly anaerobic, as their vegetative cells are killed by exposure to oxygen. However, they can survive as spores in aerobic conditions, and therefore are able to wait for anaerobic conditions required for active anaerobic bacteria growth. *Clostridium butyricum*, *Clostridium acetobutylicum*, *Clostridium pasteurianum*, and *Clostridium baratii* produce hydrogen by anaerobic fermentation of glucose, with *Clostridium butyricum* being the most effective $H_2$ producer. These bacteria may be utilized to obtain hydrogen for use as fuel or as a chemical agent in the chemical industry. In addition, *Clostridium* species may be referred to as solventogenic as they also are able to produce solvents as the result of continued fermentation of volatile organic acids (VOA) at the expense of hydrogen production, such as, by way of example only, butyrate to butanol and/or acetate to acetone.

Provided complete conversion occurs dark fermentation of biomass comprising sucrose produces eight moles of hydrogen per mole of sucrose, or alternatively four moles of hydrogen per mole of glucose. The other products of the dark fermentation process are carbon dioxide and acetic acid, a precursor to acetone. If all of the substrate were converted to butyric acid, then two moles of hydrogen may be produced per mole of glucose.

Figure 14:
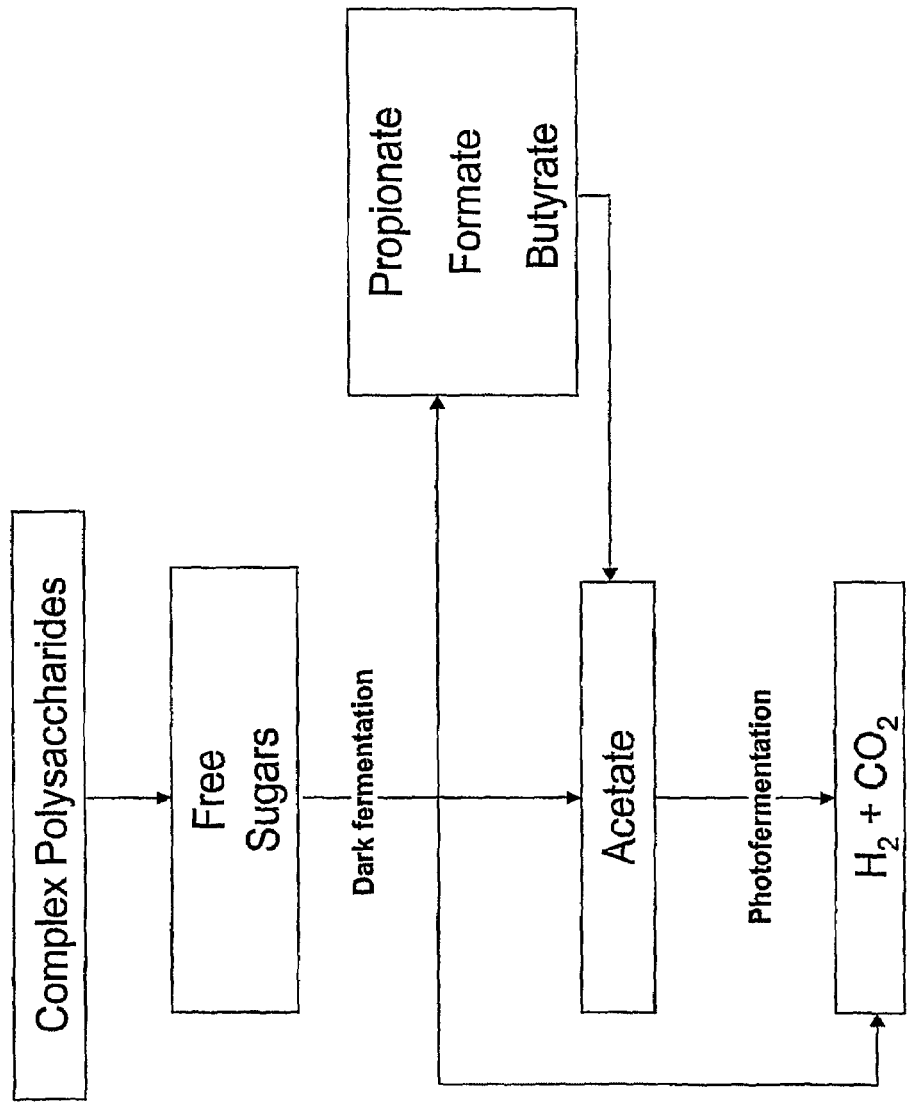
FIG. 14 presents one potential schematic showing the multi fermentation scheme used for optimal hydrogen production.

FIG. 14 is a schematic showing the basic elements involved in the conversion of complex substrates, through intermediate compounds, to hydrogen and carbon dioxide. First, complex organic compounds are hydrolyzed by extracellular enzymes to generate free sugars which are further fermented to hydrogen, carbon dioxide, and smaller organic products, primarily VOAs, such as, but not limited to, acetate, formate, butyrate and propionate. Continued fermentation of the VOAs can produce the corresponding solvent, such as acetone from acetate. Although acidogenic fermentation produces acetate, other VOAs are formed, which can be further metabolized by acetic acid producing (acetogenic) bacteria to yield hydrogen, carbon dioxide and acetate. The acetate formed may be subsequently converted into hydrogen and carbon dioxide by photofermentation, or be isolated and purified for alternative uses such as industrial chemical applications.

Although hydrogen may be produced by acidogenesis and acetogenesis, the production of VOAs or solvents may be changed or manipulated depending on the composition of the fermentation medium and the *Clostridia* species utilized. For instance, by way of example only, some cellulose-degrading *Clostridia* species degrade cellulose to glucose and then ferment the glucose, producing hydrogen, carbon dioxide, and a range of VOAs, such as formate, acetate, propionate, butyrate, and succinate, as fermentation end products. By way of example, *Clostridium thermoaceticum*, *Clostridium thermoautotrophicum*, and *Clostridium magnum*, convert glucose or sucrose to acetate, whereas; *Clostridium acetobutylicum*, which is a saccharolytic bacterium, produces acetate, butyrate, carbon dioxide, hydrogen, and some lactate when grown in glucose-limited conditions at a neutral pH. In comparison, other nonpathogenic species grown in glucose-limited media, such as *Clostridium baratii*, produce large amounts of lactate in addition to acetate and butyrate, while *Clostridium butyricum* produces large amounts of formate in addition to acetate and butyrate. In contrast, *Clostridium propionicum* fermentation of lactate produces propionate, acetate, hydrogen and carbon dioxide. Regardless of the solvents or VOAs produced, hydrogen and carbon dioxide may be obtained from anaerobic fermentation using any of these species with a variety of food sources.

The generation of large quantities of hydrogen is one aspect of the methods described herein. The approach used to achieve efficient hydrogen production is analogous to some wild ecosystems comprising various anaerobic bacteria species of the same genus and/or bacteria of different genera; wherein the fermentation waste (products) of one bacteria colony is used as a food source for a different bacteria colony. If waste is allowed to accumulate near the colony, the colony may die or its metabolic pathways alter to metabolize the waste. This latter step may allow the colony to survive, however it may not flourish. The diffusion of waste away from one colony to a different colony, where it is consumed, creates a concentration gradient which continually bleeds away waste. This symbiotic type relationship allows both colonies to flourish, without any changes in metabolic pathways. Alternatively the different bacteria species or genera may cohabitate as one colony, with bacteria feeding on the waste of neighboring bacteria.

Mimicking natural symbiotic type ecosystems for the anaerobic bacterial production of hydrogen is one aspect of the methods described herein. The initial bioprocess for anaerobic production of hydrogen from carbohydrate based biomass is the heterotrophic fermentation (dark fermentation) of carbohydrates to hydrogen, carbon dioxide and volatile organic acids (solvent precursors). The accumulation of these fermentation products decreases the pH, which can kill the bacteria, or it can initiate changes in the bacteria metabolism wherein continued fermentation (solventogenesis) of the volatile organic acids to solvents occurs at the expense of hydrogen yield. In addition, the accumulation of hydrogen and carbon dioxide may affect hydrogen yield and bacteria viability, respectively. A high hydrogen partial pressure may limit the rate of fermentation or may cause a metabolic shift, thereby increasing the conversion of solvent precursors to solvent, and severely affect the yield of hydrogen produced. The presence of a high concentration of carbon dioxide and volatile organic acids may also decrease the pH of the fermentation media, resulting in bacteria death. In addition, solvent formation from reduction of volatile organic acids by solventogenesis may also results in a decrease in pH, and potential bacteria mortality. Similarly, anaerobic fermentation of biomass containing sulfur compounds, such as, by way of example only, proteins and hydrogen sulfide ($H_2S$) which is converted into elemental sulfur by purple and green photosynthetic bacteria. High concentrations of $H_2S$ are toxic to bacteria and result in bacteria death. Therefore, in order to maintain optimal hydrogen production it is desirable to remove the dark fermentation products, such as hydrogen, carbon dioxide, and volatile organic acids (VOAs) in order to avoid these issues. Dark fermentation and removal of the heterotrophic fermentation products can proceed as either a continuous process, or batch process, or a combination of both continuous and batch processes.

Monitoring $H_2$, pH, Pressure and Temperature

While direct and indirect photolysis systems produce pure $H_2$, dark-fermentation processes produce a mixed biogas containing primarily $H_2$ and carbon dioxide ($CO_2$), but which may also contain lesser amounts of methane ($CH_4$), carbon monoxide (CO), and/or hydrogen sulfide ($H_2S$). The gas composition presents technical challenges as fuel sources, as it may require scrubbing and purification before use in some fuel cells.

Anaerobic bacteria known to produce hydrogen during dark-fermentation of carbohydrate-rich substrates include, but are not limited to, species of *Ruminococci, Archaea*, and *Clostridia*. Carbohydrates are a good substrate for hydrogen-producing fermentations. Glucose, isomers of hexoses, or polymers in the form of starch or cellulose, yield different quantities of $H_2$ per mole of glucose, depending on the fermentation pathway and end-product(s). For instance, the highest theoretical yield of $H_2$ is associated with acetate as the fermentation end-product, wherein a theoretical maximum of 4 mole $H_2$ per mole of glucose is obtained. Alternatively, when butyrate is the end-product, a theoretical maximum of 2 moles $H_2$ per mole of glucose is obtained. In practice, however, high $H_2$ yields may be associated with a mixture of acetate and butyrate fermentation products, and low $H_2$ yields are associated with propionate and reduced end-products, such as alcohols (i.e. methanol, ethanol, propanol, isobutanol, butanol, isopentanol, pentanol, acetone, propanol, isopropanol, and 1,2-propanediol), solvents and lactic acid. Note that potential hydrogen molecules remain contained in volatile organic acid products including, but not limited to acetate, butyrate, and the like. Thus, fermentation products produced by a bacterium depend on the environmental conditions in which it grows. Reduced fermentation products like ethanol, butanol, and lactate, contain hydrogen that has not been liberated as gas. For instance, the metabolism of *Clostridium pasteurianum*, which is a high volume $H_2$ and volatile organic acid (VOA) producer, can be shifted toward solvent production by having high glucose concentrations. To maximize the yield of $H_2$, the metabolism of the bacterium may be directed away from solvents (ethanol, acetone and butanol) and reduced acids (lactate), and directed more towards volatile organic acids.

The concentration of hydrogen, carbon dioxide, carbon monoxide, and/or hydrogen sulfide, both in solution and in the head space above the dark fermentation media, increase as dark fermentation proceeds. The yield of hydrogen during dark fermentation is dependent on process conditions such as pH, temperature, buffer capacity, hydraulic retention time (HRT), and gas partial pressure; each of which may affect metabolic balance. To ensure optimal hydrogen production occurs during anaerobic dark fermentation, these process parameters, as well as the concentration of fermentation products, such as volatile organic acids, hydrogen, carbon dioxide, carbon monoxide and hydrogen sulfide, need to be monitored either continuously or at regular intervals.

Temperature is an important parameter in establishing the fermentation rate and determining the stability of the fermentation process. Digesters fermentation reactions can be operated at mesophilic (25-40 C), thermophilic (40-65 C), extreme thermophilic (65-80 C), or hyperthermophilic (>80 C) temperatures. Higher gas yields may be obtained using thermophilic conditions; however this requires energy to heat the digester. A 5 C to 10 C fluctuation in temperature may result in an imbalance in fermentation and lead to digester instability for either temperature range, however thermophilic digestion is more sensitive to such fluctuations. Therefore, to ensure optimal anaerobic fermentation it is necessary to monitor and control the digester temperature. The digester temperature can be monitored using thermal sensors, such as, by way of example only, thermometers, thermopiles, and thermocouples, which are placed either inside the digester or on the outside surface of the digester. Similarly, infra-red thermal sensors may be used as non-invasive thermal monitoring methods by measuring the radiative heat from the digester. However, using infra-red sensors, or monitoring the inside temperature by measuring the outside surface temperature, requires calibration to correlate the outside temperature with the inside temperature of the digester. Regardless of the method used to measure the digester temperature, the information can be used in a control loop as feedback to the system used to heat the digester, such as, by way of example only, hot plates, or heating mantles. The system used to heat the digester is adjusted manually, or may be automated by computer control, to maintain the optimal temperature needed. The heat required by these processes can be provided by the waste exhaust heat from power generating equipment. A non-limiting example of such a process is the use of low pressure steam exhausted from a back pressure turbine system.

The fermentation process and products may be affected by the pH of the fermentation media. During dark fermentation at pH values greater than about 5.6 (depending on the bacteria strain), the exponential growth of bacteria, such as, by way of example only, *Clostridium acetobutylicum*, generates large quantities of fermentation products, such as volatile organic acids (e.g. formic acid, acetic acid, propionic acid, butyric acid, and valeric acid), carbon dioxide and hydrogen. The formation of carbonic acid (from carbon dioxide) and volatile organic acids causes the pH to decrease, and as the acids accumulate, particularly in batch cultures, growth becomes linear and gradually stops. In addition, the bacteria may die if the pH decreases significantly. Also, when the pH drops to 4.5-5.0, a shift in fermentation processes may occur, resulting in solvent formation (solventogenesis). The shift to solventogenesis is induced by high intracellular concentrations of acids, low pH, a growth limiting factor (such as phosphate or sulfate depletion) and high concentrations of glucose and nitrogen compounds. Solvent formation, allows for further metabolism by preventing excessive acidification, but this may be at the expense of hydrogen yield. Solventogenesis requires the induction of a new set of enzymes catalysing the formation of acetone, butanol and ethanol from glucose and assimilated acids. Also, solventogenic *Clostridia*, depending on the strain and fermentation conditions, can produce other alternative solvents such as propanol, isopropanol and 1,2-propanediol.

Optimal hydrogen production from dark fermentation may be maintained and solventogenesis may be minimized by monitoring of the fermentation media pH, either continuously or by periodic sampling. In-line and/or on-line monitoring methods may be used for continuous pH monitoring. In-line monitoring methods use instrumentation which can be directly inserted into the digester, whereas, on-line monitoring involves diverting a small stream of media to a location where it is either continually sampled and analyzed by fixed instrumentation, or manually sampled and tested elsewhere. The stream of media is then either re-circulating back into the digester, after appropriate sterilization, or taken off as waste. Examples of in-line pH monitoring instrumentation are, but not limited to, glass membrane type pH electrodes, solid state type pH electrodes (e.g. silicon nitride based and metal oxide based), and optodes (optical type pH electrodes using fluorescence or absorbance measurements of pH sensitive dyes). In-line methods require sterilization of the measuring system and may have issues with electrode fouling for particulates and bacteria. On-line monitoring methods do not require sterilization, provided no recirculation of the media occurs, plus it allows for sample clean up by filtering of bacteria and particulates from the test stream. Examples of on-line pH monitoring instrumentation are, but not limited to, glass membrane type pH electrodes, solid state type pH electrodes (e.g. silicon nitride based and metal oxide based), optodes (optical type pH electrodes using fluorescence or absorbance measurements of pH sensitive dyes), and flow injection analysis (FIA). The same methodologies used for on-line monitoring may be used for periodic sampling. The pH information obtained may be used for feedback in a control loop to the system used to adjust the pH and thereby maintain the optimal pH for optimal growth. Examples of methods to adjust the pH include, but are not limited to, addition of deoxygenated solutions of sodium hydroxide to increase the pH and addition of deoxygenated solutions of hydrochloric acid to decrease the pH. This control of the pH adjustment system may be achieved manually, or may be automated by computer control.

The partial pressure of $H_2$ (pH2), is a parameter which may be monitored during continuous $H_2$ synthesis as it reflects the concentration of $H_2$. Hydrogen synthesis pathways may be sensitive to $H_2$ concentrations and which can then be subject to end-product inhibition. As $H_2$ concentrations increase, $H_2$ synthesis decreases and metabolic pathways shift to production of more reduced substrates such as lactate, ethanol, acetone, butanol, or alanine. In addition, temperature also affects the pH2 such that, by way of example only, for optimal $H_2$ synthesis, $pH_2 < 50$ kPa at 60° C.; $pH_2 < 20$ kPa at 70° C.; pH2 and $pH_2 < 2$ kPa at 98° C. The increase in temperature is aimed at better performance of the hyperthermophiles hydrogenases, because the affinity for hydrogen decreases and the thermodynamic equilibrium of hydrogen formation from acetate, or other volatile organic acids, is favored at higher temperatures. In addition, at large hydrogen and carbon dioxide concentrations there is potential for the onset of acetogenesis, resulting in the formation of acetate from hydrogen and carbon dioxide. Although this conserves the hydrogen in a different chemical form, it decreases the potential dark fermentation yield of hydrogen. In addition, the rate of fermentative hydrogen production may be inhibited by high partial pressures (i.e. concentration) of hydrogen.

The measurement of hydrogen is achieved using techniques known in the art, and may be carried out in the head space inside the digester or externally in the pipe/tube system used remove the biogas from the digester. Described below are examples of hydrogen gas measurement systems, however, any hydrogen sensing or measurement system known in the art may be used. As with pH monitoring, any of the hydrogen measurements may be used either continuously or by periodic sampling, and may used as in-line and/or on-line monitoring methods. Hydrogen gas measurement may be achieved using fiber optic sensors based on the chemochromic reaction of certain transition metal oxides, such as tungsten oxide or W03 with hydrogen in air, wherein, the reaction is catalyzed by palladium or platinum, and the color change of the film in the presence of hydrogen is detected by reflectance spectroscopy. Another method is to use thermal conductivity detectors (TCD), in which the thermal conductivity of the digester gas is compared to that of a reference gas, and the difference in conductivity can then be calibrated to give a hydrogen concentration value. Thermal conductivity detection may also be used in conjunction with gas chromatography (GC) as a method to identify the various components of the fermentation gas mixture and obtain their respective concentrations. The application of GC with TCD detection for gas analysis is know to one skilled in the art. Sensing is based on resistance changes upon hydrogen adsorption to platinum and/or palladium, field effect transistors based on carbon nanotubes are other approaches used to monitoring hydrogen concentrations in digesters. The hydrogen concentration information obtained may be used for feedback in a control loop to the system used to control the removal of fermentation gases from the digester. In addition, the gas flow rate may be monitored to assist in controlling the removal of gases from the digester. Typical methods for measuring flow rate are thermal based detectors, or hot wire anemometers. The system used for gas removal may be manually controlled, or may be automated using computer control. Methods for removal of fermentation gases from digesters will be known to those skilled in the art, however, one possible method is to control a vacuum system attached to the digester.

Similarly, carbon dioxide in dark fermentation biogas mixtures may be monitored using measurement systems know to one skilled in the art. However, some examples for detecting carbon dioxide are fiber optic sensors based fluorescence and absorbance changes with pH sensitive dyes, non-dispersive infra-red detection, field effect transistors based on carbon nanotubes, pyroelectric detectors, thermal conductivity detectors, and thermal conductivity detectors coupled with gas chromatography. The carbon dioxide concentration information obtained may be used for feedback in a control loop to the system used to control the removal of fermentation gases from the digester. In addition, the gas flow rate may be monitored to assist in controlling the removal of gases from the digester. Typical methods for measuring flow rate are thermal based detectors, or hot wire anemometers. The system used for gas removal may be manually controlled, or may be automated using computer control. Methods for removal of fermentation gases from digesters will be known to those skilled in the art, however, one possible method is to control a vacuum system attached to the digester.

Carbon monoxide in dark fermentation biogas mixtures may be monitored using measurement systems know to one skilled in the art. However, some examples for detecting carbon monoxide are electrolytic sensors, colorimetric sensor, MOS detectors (Metal Oxide Semiconductor Sensor), thermal conductivity detectors, and thermal conductivity detectors coupled with gas chromatography. The carbon monoxide concentration information obtained may be used for feedback in a control loop to the system used to control the removal of fermentation gases from the digester. In addition, the gas flow rate may be monitored to assist in controlling the removal of gases from the digester. Typical methods for measuring flow rate are thermal based detectors, or hot wire anemometers. The system used for gas removal may be manually controlled, or may be automated using computer control. Methods for removal of fermentation gases from digesters will be known to those skilled in the art, however, one possible method is to control a vacuum system attached to the digester.

Hydrogen sulfide in dark fermentation biogas mixtures may be monitored using measurement systems know to one skilled in the art. However, some examples for detecting $H_2S$ are conductiometric sensors (CuO—SnO2) based on resistance changes upon exposure to $H_2S$, thermal conductivity detectors, and thermal conductivity detectors coupled with gas chromatography. The hydrogen sulfide concentration information obtained may be used for feedback in a control loop to the system used to control the removal of fermentation gases from the digester. In addition, the gas flow rate may be monitored to assist in controlling the removal of gases from the digester. Typical methods for measuring flow rate are thermal based detectors, or hot wire anemometers. The system used for gas removal may be manually controlled, or may be automated using computer control. Methods for removal of fermentation gases from digesters will be known to those skilled in the art, however, one possible method is to control a vacuum system attached to the digester.

Gas partial pressure may affect the metabolic balance and therefore affects the hydrogen yield obtained from dark fermentation. The digester pressure may be monitored using methods and techniques known to one skilled in the art. However, examples of pressure sensing methods used to monitor the digester pressure are solid state pressure sensors or manometers, either attached to the digester or incorporated with the outlet pipe/tube. The pressure information obtained may be used for feedback in a control loop to the system used to control the removal of fermentation gases from the digester. In addition, the gas flow rate may be monitored to assist in controlling the removal of gases from the digester. Typical methods for measuring flow rate are thermal based detectors, or hot wire anemometers. The system used for gas removal may be manually controlled, or may be automated using computer control. Methods for removal of fermentation gases from digesters will be known to those skilled in the art, however, one possible method is to control a vacuum system attached to the digester.

In dark-fermentation processes, the gas produced is a mixture of primarily $H_2$ and $CO_2$, but may also contain other gases such as CO, methane, and $H_2S$, depending on the biomass and bacteria present. If the digester becomes contaminated with undesirable bacteria it is likely that other fermentation gases, such as methane ($CH_4$) from methanogenesis and ammonia ($NH_4$) from nitrate or nitrite reduction may be present. Early detection of these contamination gases may allow for quick containment and remedy of the contamination. One method for detection and quantification of contamination gases is, but not limited to, thermal conductivity detection in conjunction with gas chromatography (GC). This method allows identification of the various components of the fermentation gas mixture and obtains their respective concentrations.

Optimal hydrogen production from dark fermentation may be maintained and solventogenesis may be minimized by monitoring, either continuously or by periodic sampling, the nutrient concentration in the fermentation media. In-line and/or on-line monitoring methods may be used for nutrient monitoring. In-line monitoring methods use instrumentation which can be directly inserted into the digester, whereas, on-line monitoring involves diverting a small stream of media to a location where it is either continually sampled and analyzed by fixed instrumentation, or manually sampled and tested elsewhere. The stream of media is then either re-circulating back into the digester, after appropriate sterilization, or taken off as waste. Examples of in-line nutrient monitoring instrumentation are, but not limited to, glucose sensors (optical or amperometric). In-line methods require sterilization of the measuring system and may have issues with electrode fouling from particulates and bacteria. On-line monitoring methods do not require sterilization, provided no recirculation of the media occurs, plus it allows for sample clean up by filtering of bacteria and particulates from the test stream. Examples of on-line nutrient monitoring instrumentation are, but not limited to, glucose sensors (optical or amperometric), flow injection analysis (FIA) methods, high performance liquid chromatography (HPLC), high performance liquid chromatography coupled with Mass Spectrometry (HPLC-MS), and capillary electrophoresis (CE). The same methodologies used for on-line monitoring may be used for periodic sampling. The nutrient concentration information may be used for feedback in a control loop to the system used to add nutrients into the digester, and thereby maintain the optimal nutrient concentration for optimal growth. The control of nutrient addition may involve adjusting a valve, either manually or computer controlled, to increase or decrease addition of deoxygenated nutrient solutions into the digester.

In addition, monitoring of the volatile organic acid fermentation products, either continuously or by periodic sampling, is needed for optimal hydrogen production from dark fermentation. In-line and/or on-line monitoring methods may be used for volatile organic acid monitoring. Examples of on-line volatile organic acid monitoring instrumentation are, but not limited to, Fluorescence Immunoassay (FIA) methods, high performance liquid chromatography (HPLC), high performance liquid chromatography coupled with Mass Spectrometry (HPLC-MS), capillary electrophoresis (CE), and ion chromatography. The same methodologies used for on-line monitoring may be used for periodic sampling. The volatile organic acid concentration information may be used for feedback in a control loop to the system used to remove the volatile organic acid from the digester, and thereby maintain the minimal volatile organic acid concentration necessary for optimal growth. Volatile organic acids may be removed by cross flow dialysis, with the rate of removal dependent on the flow rate of the media on the opposite side of the dialysis membrane. The control of flow rate may involve adjusting a pump, either manually or computer controlled, to increase or decrease the flow rate of the deoxygenated media used to remove the volatile organic acid from the digester as they diffuse across the dialysis membrane.

Changes in the fermentation buffer capacity may be obtained with knowledge of the digester pH and the concentrations of the volatile organic acids. If the buffer capacity is too low, such that a slight increase in fermentation rate may cause a rapid decrease in pH, then fresh deoxygenated media may be added. The buffer capacity information may be used for feedback in a control loop to the system used to add deoxygenated media into the digester, and thereby maintain the optimal buffer capacity. The control of media addition may involve adjusting a valve, either manually or computer controlled, to increase or decrease addition of deoxygenated media into the digester.

Removal of the dark fermentation products, such as hydrogen, carbon dioxide, hydrogen sulfide, carbon monoxide and the volatile organic acids during fermentation creates conditions for use of concentrated nutrients and the ability to maintain optimal hydrogen production. Without this removal process hydrogen production would be diminished due to initiation of alternate metabolic pathways at high concentration of fermentation products. Therefore, separation of microbial growth and product formation improves hydrogen production yields, however optimizing the process conditions, such as pH, and temperature also improve hydrogen yield.

Removal of Hydrogen, Carbon Dioxide and Hydrogen Sulfide

Dark-fermentation systems have great potential as practical biohydrogen systems by incorporating rapid gas removal and separation, rapid volatile organic acid removal and separation, and bioreactor design. In dark-fermentation processes, the gas produced in the anaerobic digester is a mixture of $H_2$ and $CO_2$, but may also contain other gases such as CO, $CH_4$, $H_2S$, or ammonia ($NH_4$), which is be present in fermentation media and headspace above the reaction solution. The content of each gas in the headspace and the reaction solution varies according to the conditions, feed stock and/or anaerobic microbe present within the anaerobic digester. Rapid removal and purification of the $H_2$ and removal of diluting ($CO_2$, $CH_4$) and/or contaminating (CO, $H_2S$) gases allows for maintaining continuous $H_2$ synthesis.

As discussed above, the pH2 is a parameter which may be monitored during continuous $H_2$ synthesis, since with increasing $H_2$ concentrations, $H_2$ synthesis decreases and metabolic activity shifts to pathways that synthesize more reduced substrates. Thus, efficient gas removal bypasses these pathways, thereby increasing $H_2$ production. The concentration of $CO_2$, also affects the rate of synthesis and final yield of $H_2$ due to succinate and formate synthesis using $CO_2$, pyruvate and nicotinamide adenine dinucleotide (NADFf) via the hexose monophosphate pathway. This pathway competes with reactions in which $H_2$ is synthesized by NADH-dependent hydrogenases (which oxidize NADH to NAD+). Thus, efficient removal of $CO_2$ from the fermentation system reduces competition for NADH, and results in increased $H_2$ synthesis.

Methods of removal of fermentation gases include, but are not limited to, sparging with $N_2$ or argon (Ar) gas, applying a vacuum to the digester head space, or using membrane technologies, such as, by way of example only, hollow fiber/silicone rubber membranes and non-porous, synthetic polyvinyltrimethylsilane (PVTMS) membranes.

The hydrogen and carbon dioxide produced by dark fermentation in the anaerobic digester may be cleaned or purified by a scrubber to remove moisture, vapor, droplets, suspended solids or other such contaminants. The scrubber can comprise one or more of a filter, desiccant, zeolite, activated carbon, fiber, countercurrent wash solution, mixer, homogenizer, or other such components typically used in association with or comprised within gas scrubbers. Such components are well known to those of ordinary skill in the art of gas processing. In general, hydrogen sulfide ($H_2S$) is an undesired by-product or off-gas, which is removed from the desired hydrogen gas; however it may be used as feed stock for bacteria such as, by way of example only, purple sulfur bacteria, to obtain more hydrogen and elemental sulfur.

The gases which exit the anaerobic digester or the scrubber are then optionally separated into their individual components using conventional gas separation equipment, which is known to those of ordinary skill in the art for separating gas mixtures. By way of example only, $H_2S$ and $CO_2$ can be removed from the gas product stream with the use of membranes which are permeable to $H_2S$ or $CO_2$ and not permeable to hydrogen. Alternatively, palladium-silver alloy/ceramic composite membranes with high selectivity and flux rate for hydrogen may be used for separating hydrogen from $CO_2$ and $H_2S$. Thus, $CO_2$ and $H_2S$ may be selectively stripped from the gas product stream yielding purified $H_2$. In addition, the, $CO_2$ may be selectively stripped from $H_2S$ using a variety of methods for $H_2S$ removal, such as, by way of example only, a monoethanolamine Girbotol type process. The $CO_2$ may then be isolated and purified for later use. Alternatively, the $CO_2$ and $H_2S$ mixture may be used as feed stock for purple sulfur bacteria, wherein the $H_2S$ is converted into hydrogen and elemental sulfur, and the $CO_2$ is subsequently removed from the $H_2$ to yield purified $CO_2$ and $H_2$.

Alternatively, the gases which exit the anaerobic digester are separated and purified using a differential compression system. The differential compression process involves initially drying the mixture of gaseous anaerobic fermentation products, such as, but not limited to, hydrogen, and carbon dioxide, then compressing and cooling the mixture to transform at least one of the gases into a liquid form. The remaining gaseous products may then be compressed and cooled at a different location using different conditions, thus making the process a differential compression process. The conditions used for compressing and cooling vary depending on the gas mixture. By way of example only, the removal and purification of hydrogen from carbon dioxide may use a pressure of 58 bars at a temperature of 15° C. to liquefy the carbon dioxide allowing for easy separation of the gaseous hydrogen.

Once separated, the hydrogen may be optionally processed with one or more dehydration stages, then compressed and alternatively stored in pressurized storage vessels or tanks, or used directly as a fuel to generate electricity via fuel cells or combustion/turbine type systems. The generated electricity may then be used to operate the anaerobic digester and associated facility, or can be added to the external power system via connection to the external grid. If the purified hydrogen is stored, it can be used later as a fuel source, or used as a chemical component in an industrial process. Similarly, the purified $CO_2$ can be directly used as feed stock for alternate fermentation processes, it can be stored and used later as feed stock, it can be used as a greenhouse supplement to enhance greenhouse plant, fruit and vegetable production, it can be used as a refrigerant in the anaerobic fermentation facility, it can be used as a fire-extinguishing material, or it can be used as chemical component in an industrial process, such as soda ash production. In addition, collected carbon dioxide may be used commercially such as, but are not limited to, in the production of carbonated beverages, in water softening, in the manufacture of aspirin, used as a refrigerating agent, used in the Solvay process for the preparation of sodium carbonate, used to provide an inert atmosphere for packaging and storage of foods, and used as pressurizing medium and propellant in aerosol cans of food, fire extinguishers, target pistols, and for inflating life rafts.

Substantial gains in $H_2$ production can also be achieved through optimization of bioreactor designs. By way of example only, fixed-bed bioreactors enhance $H_2$ production by using activated carbon as a support matrix, plus a membrane filter system for removal of the biogas. The support matrix allows for retention of the $H_2$ producing bacteria within the bioreactor, and the membrane system maintains low gas partial pressures.

Removal of Volatile Organic Acids

The volatile organic acids generated during dark fermentation are removed as their accumulation may have an effect on the anaerobic bacteria's ability to produce hydrogen. In particular, as fermentation proceeds the pH decreases, and continued fermentation may yield pH-neutral components such as acetone and butanol at the expense of hydrogen production. Removal of these products can be either continuously or in batch mode, wherein both continuous and batch removal methods include, but are not limited to, dead-end filtration, cross-flow filtration, ultrafiltration, pervaporation, and dialysis. Dead-end filtration involves the use of a filter element through which the media is passed while leaving the bacteria and other solid particulates behind. The use of a dead-end filter can be continuous, with fresh media being introduced to replenish the quantity filtered, alternatively dead-end filtration can be a batch process. One issue encountered with dead-end filtration is clogging and potential blockage of the filter element, which can limit the through put of a continuous system. To overcome clogging issues a cross flow filtration system can be used, wherein tangential flow of media, bacteria and other particulates occurs across the filter element minimizing the potential for clogging. Cross-flow filtration can also be used in a batch mode approach. Ultrafiltration can be used for bacteria not filterable using other pore sizes. The presence of filter systems effectively removes the volatile organic acids from the fermentation culture, and generally, dead-end filtration, cross-flow filtration and ultrafiltration use positive pressure to force fluid through the filter element. Alternatively; methods without the use of positive pressure to force fluid through a filter element, such as reverse osmosis, dialysis or electro-dialysis, may be used for the removal of the volatile organic acids from the dark fermentation culture.

The use of dialysis for the removal of volatile organic acids from the bacteria used for dark fermentation relies on diffusion of the volatile organic acids across a semi-permeable membrane and leaving the bacteria behind. A concentration gradient is needed for the process to occur and this can be achieved continuously or in a batch mode. In the batch mode the dark fermentation culture is poured into a dialysis bag (constructed from semi-permeable membrane material) and the filled bag is placed into a container of fresh fermentation media or water. A concentration gradient is present between the inside of the bag and the outside, and diffusion of soluble ions and molecules across the semi-permeable membrane. Large molecules, particles and bacteria which are unable to pass through the semi-permeable membrane remain inside the bag. This process continues until equilibrium is reached, after which a fresh container of fresh fermentation media or water is used for thorough removal of volatile organic acids. In a continuous process a semi-permeable membrane may be used to separate the dark fermentation digester from a system in which fresh fermentation media or water is flowing past, thereby creating a concentration gradient and continuously removing volatile organic acids as they diffuse into the flowing stream.

Electro-dialysis is a membrane process, during which ions are transported through semi permeable membrane, under the influence of an electric potential. The membranes are cation- or anion-selective, allowing either positive ions or negative ions to flow through. Cation-selective membranes may be negatively charged polyelectrolytes, which rejects negatively charged ions and allows positively charged ions to flow through. Cation-selective membranes may be sulphonated polystyrene, while anion-selective membranes may be polystyrene with quaternary ammonia functional groups. Particles and bacteria are too large to pass through the membrane and are not removed. Electro-dialysis can also be used in a continuous or batch process as described above for dialysis.

The filtrate obtained from the above methods may be further purified with the use of reverse osmosis. Reverse osmosis, also known as hyperfiltration, process uses a membrane that is semi-permeable, allowing the fluid to pass through it, while rejecting ions from crossing. This in effect is a method to concentrate and purify the volatile organic acids obtained from dark fermentation. The process of reverse osmosis requires a driving force to push the fluid through the membrane, and the most common force is pressure from a pump. Most reverse osmosis technology uses a process known as cross flow to allow the membrane to continually clean itself, analogous to cross flow filtration. As some of the fluid passes through the membrane the rest continues downstream, sweeping the rejected species away from the membrane. Reverse osmosis is capable of rejecting bacteria, salts, sugars, proteins, particles, dyes, and other constituents that have a molecular weight of greater than 150-250 daltons (Da). The separation of ions with reverse osmosis is aided by charged membranes. Thus, dissolved ions that carry a charge, such as salts, are more likely to be rejected by the membrane than those that are not charged, such as organics. In this manner, any solvents produced, such as, by way of example only, acetone, may be removed while maintaining the volatile organic acids in the flow stream. The larger the charge and the larger the particle, the more likely it will be rejected.

The volatile organic acids may be removed from the anaerobic fermentation system and then purified by osmosis as a salt. The volatile organic acids anions, including, but not limited to, formate, acetate, propionate, butyrate, and valerate, may be combined with alkali metal cations, alkaline earth cation, ammonium ion, and combinations thereof to form a salt. By way of example only, the cations may be $Na^+$, $K^+$, $Ca^{2+}$, $Mg^{2+}$, $NH_4^+$, or combinations thereof.

Convert Volatile Organic Acids to $H_2/CO_2$

The filtrate obtained from dead-end filtration, cross-flow filtration, ultrafiltration, or dialysis of the dark fermentation stage may contain other volatile organic acids than acetic acid. Therefore, the filtrate may be fed into separate anaerobic digesters and further metabolized by acetic acid producing (acetogenic) bacteria to yield hydrogen, carbon dioxide and acetate. A close monitoring of hydrogen concentrations is necessary for acetogenic bacteria conversion of fatty acids (e.g., formic, acetic, propionic, isobutyric, butyric, isovaleric, valeric, isocaproic, caproic, and heptanoic acids) and alcohols into acetate, hydrogen, and carbon dioxide because acetate formation may be reduced under relatively high $H_2$ partial pressure. The use of acetogenic bacteria for generation of acetate not only increases hydrogen output, but it is an alternative approach to increasing the acetate concentration in the filtered dark fermentation media. The acetate generated during acetogenic bacteria fermentation may be used as feed stock for other fermentation stages in separate anaerobic digesters, such as, by way of example only, photo-fermentation (FIG. 14). With light, and under anaerobic conditions, reduced organic compounds, like acetic acid, can be converted to hydrogen and carbon dioxide by certain microorganism, such as, by way of example only, purple bacteria (*Chromatium, Rhodospirillium, Rhodomicrobium*). Therefore, photo-fermentation may be added as another fermentation stage to obtain more hydrogen from the photoheterotrophic fermentation of acetate into hydrogen and carbon dioxide. The hydrogen and carbon dioxide can be separated and purified.

Alternatively, the filtrate obtained from dead-end filtration, cross-flow filtration, ultrafiltration, or dialysis of the dark fermentation stage, or the media, concentrated by reverse osmosis, may be further purified to isolate the various volatile organic acids. Isolation and purification methods can include distillation, adsorption chromatography, ion exchange chromatography, and affinity chromatography. Such purified volatile organic acids may then be used as either commercial products, or as precursors or reactants for synthesis of commercial products.

Convert $H_2S$ with Appropriate Bacteria to $H_2/CO_2$ and Sulfur

Proteobacteria or "purple bacteria" may be the largest and most physiologically diverse group of bacteria, which exhibit a wide variety of types of metabolism: aerobic, anaerobic, heterotrophic, autotrophic, phototrophic, and lithotrophic. The use of carbon dioxide as the carbon source and an inorganic compound (water, or $H_2S$) as the source of reducing power is reflected in the terms autotroph and lithotroph (respectively) which are used for an organism performing this reaction. With light as the ultimate source of energy, the organism would also be termed a phototroph. Thus, in addition to protobacteria being anoxygenic photoheterotrophs, proteobacteria include chemolithotrophs and chemoorganotrophs, wherein lithotrophs are able to fix carbon, while organotrophs require fixed carbon as a nutrient. Thus, purple bacteria may be used for $H_2$ and $CO_2$ production from acetate by a photoheterotrophic process, or alternatively, purple bacteria may be used to obtain hydrogen and elemental sulfur from $H_2S$ in an anaerobic lithotrophic process.

Proteobacteria are all gram negative, but otherwise represent a diverse range of organisms such as the purple phototrophic, nitrifying bacteria and enteric bacteria, as well as the bacteria responsible for animal bioluminescence. They can be divided into five sections (depending on their RNA), referred to by the Greek letters alpha, beta, gamma, delta and epsilon. Photosynthetic protobacteria (anoxygenic photoautotrophy) are found in alpha, beta, and gamma groups, in particular purple sulfur bacteria are generally beta or gamma proteobacteria, and purple non-sulfur bacteria are primarily alpha proteobacteria. Alpha, beta, and gamma groups also include chemolithotrophs and chemoorganotrophs. In contrast, the delta and epsilon proteobacteria are not photosynthetic and are all chemoorganotrophs.

Most purple bacteria are strict anaerobes and live in the sediment of ponds and lakes. Purple phototrophic bacteria use energy from sunlight in a process known as anoxygenic photosynthesis and can be divided into two groups depending whether or not hydrogen sulfide ($H_2S$) is used as an electron donor for carbon dioxide reduction. If $H_2S$ is used as an electron donor then they are called purple sulfur bacteria, if $H_2S$ is not used as an electron donor, then they are known as purple non-sulfur bacteria. For purple non-sulfur bacteria, hydrogen can be used as the reducing agent, although some purple non-sulfur bacteria may use other compounds. Purple sulfur bacteria fix $CO_2$ to live, whereas non-sulfur purple bacteria can grow aerobically in the dark by respiration on an organic carbon source.

Purple sulfur bacteria normally are anaerobic or microaerophilic, and are often found in sulfur springs or stagnant water. An environment they can be found in is the illuminated but anoxic zones of these aquatic environments. The presence of oxygen hinders their growth. Purple sulfur bacteria oxidize $H_2S$ or S as an electron donor for carbon dioxide reduction during the dark reaction of photosynthesis. The $H_2S$ is oxidized to produce granules of elemental sulfur, which in turn may be oxidized to form sulfuric acid and therefore acidifies the environment. Some of the sulfur oxidizers are acidophiles that are able to grow at a pH of 1 or less. The photosynthetic proteobacteria may be placed into two families, the Chromatiaceae and the Ectothiorhodospiraceae. Ectothiorhodospiraceae are gamma-proteobacteria, but are distinctive because they deposit sulfur on the outside of their cells, whereas Chromatiaceae deposit sulfur inside their cells. This behavior may be utilized to obtain elemental sulfur from oxidation of $H_2S$, which has been obtained from certain types of biomass during anaerobic dark fermentation.

Lithoautotrophic sulfur oxidizers are found in environments rich in $H_2S$, such as volcanic hot springs and fumaroles, and deep-sea thermal vents. Some are found as symbionts and endosymbionts of higher organisms. Since they can generate energy from an inorganic compound and fix $CO_2$ as autotrophs, they may play a fundamental role in primary production in environments that lack sunlight. In addition, some are hyperthermophiles that grow at temperatures of 115° C., while some are halophilic (salt loving), such as the genus *Halothiobacillus*, which can be found in soda lakes and salterns.

Most purple non-sulfur photosynthetic bacteria are able to grow as photoheterotrophs, photoautotrophs or chemoheterotrophs. A few species are capable of anaerobic growth though most species are aerobic. The mode of growth is determined by the available conditions, such as, availability of light (needed for phototrophic growth), the degree of anaerobiosis (oxygen level), the availability of $CO_2$ as a carbon source for autotrophic growth, and the availability of organic compounds (such as simple sugars, volatile organic acids, and aromatic compounds) for heterotrophic growth. Therefore, photo-fermentation may be used to obtain more hydrogen from the photoheterotrophic fermentation of acetate into hydrogen and carbon dioxide by purple non-sulfur. Typical purple non-sulfur bacteria genera are *Rhodospirillum* and *Rhodopseudomonas* and *Rhodobacter*.

Chemotrophic growth for the purple non-sulfur bacteria is achieved by respiration, although there are some exceptional strains and species which can obtain energy by fermentation or anaerobic respiration. In addition, it was thought that purple non-sulfur bacteria could not use hydrogen sulfide as an electron donor for the reduction of carbon dioxide when growing photoautotrophically, hence the use of "non-sulfur" in their group name. Sulfide can be used if present in a low concentration, however, higher concentrations of $H_2S$ (in which the purple sulfur bacteria and green sulfur bacteria can thrive) are toxic.

Use of Fermentation Products

Figure 15:
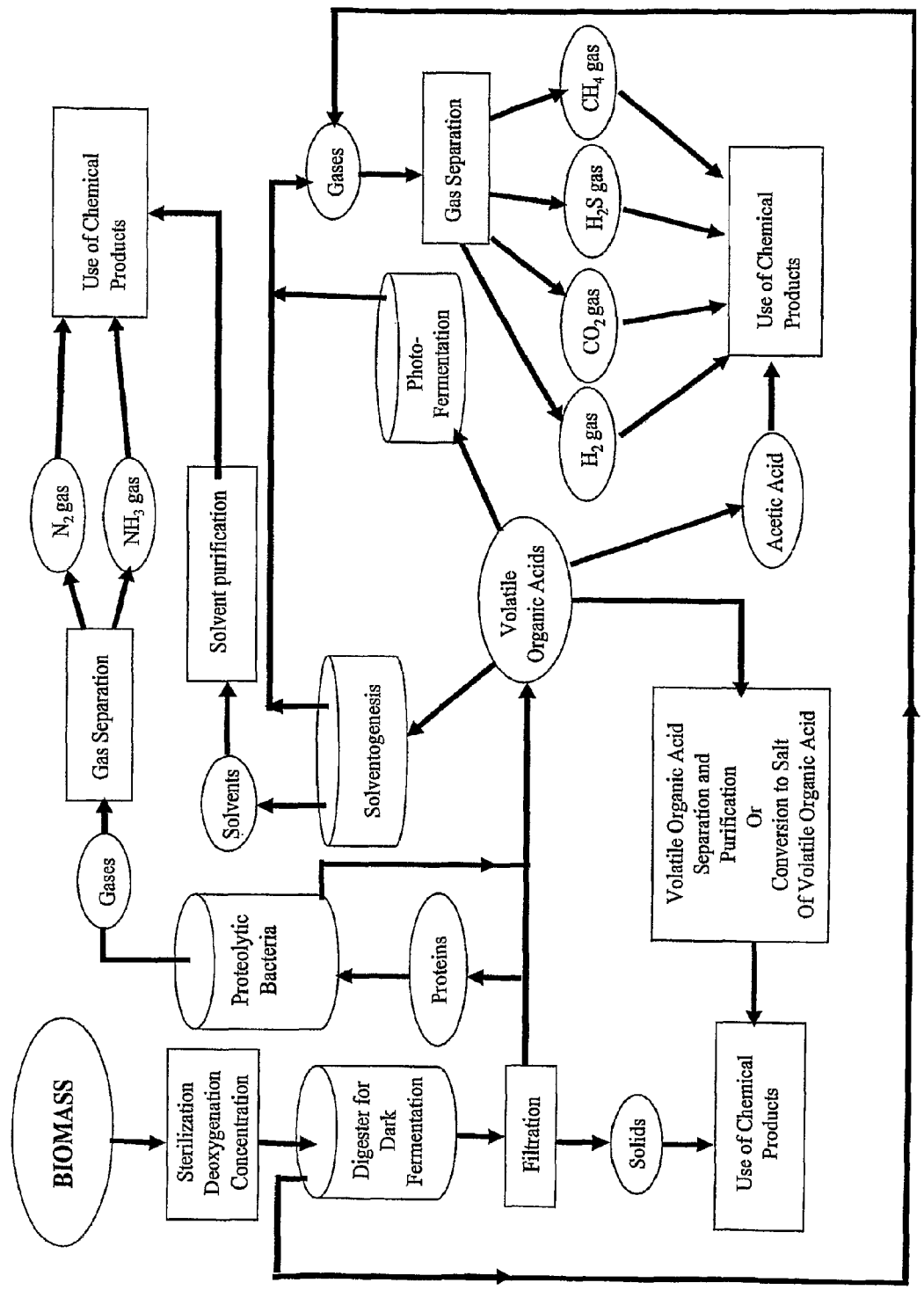
FIG. 15 presents one potential schematic of the showing the various uses for the anaerobic fermentation products.

FIG. 15 is a schematic showing one approach toward producing and processing various fermentation products for their use. The fermentation products, also referred to as chemical products, may include, but are not limited to, gases, volatile organic acids, solids and solvents. These chemical products may be obtained from dark fermentation, acetogenesis, photo-fermentation, solventogenesis, fermentation with proteolytic bacteria, or combinations thereof. The gases produced include, but are not limited to, hydrogen, carbon dioxide, carbon monoxide, hydrogen sulfide, methane, ammonia, and nitrogen; which are removed from the various digesters, separated and purified for use as feedstock for chemical industry, as energy sources for power production, or as products themselves. The volatile organic acids include, but are not limited to, formic acid, acetic acid, propionic acid, butyric acid, and valeric acid; which are removed from the various digesters, separated and purified for use as feedstock for chemical industry, feedstock for other fermentation processes, or as products themselves. In addition, the volatile organic acids may be removed from the digester and converted to the respective salts of the volatile organic acids, which comprise at least one cation. The anions of such salts include, but are not limited to, formate, acetate, propionate, butyrate, and valerate, while the at least one cation includes, but is not limited to, alkali metal ions (such as, by way of example only $Na^+$ and $K^+$), an alkaline earth ions (such as, by way of example only $Ca^{2+}$ and $Mg^{2+}$), and ammonium ion ($NH_4^+$). The solvents produced include, but are not limited, to acetone, butanol, propanol, isopropanol, 1,2-propanediol, and the solid may be compounds which comprise sulfur, or may be elemental sulfur. The solvents and solids are removed from the various digesters, separated and purified and may be used as feedstock for chemical industry, as energy sources for power production, or as products themselves.

The fermentation products, such as gases, volatile organic acids, salts of volatile organic acids, solids and solvents may be used as feedstock in other industries, such as, but not limited to, polymer industry, industrial synthesis industry, photographic industry, coatings industry, fertilizer industry, printing industry, and combinations thereof. In addition, the volatile organic acids may also be used as feedstock for other fermentation processes, such as, but not limited to, acetogenesis (to produce more acetic acid from other volatile organic acids), photo-fermentation (to produce more hydrogen and other fermentation gases, such as, but not limited to, carbon dioxide) and solventogenesis (to produce solvents and more hydrogen and other fermentation gases, such as, but not limited to, carbon dioxide). By way of example only, acetic acid obtained from the dark fermentation and acetogenic conversion can be purified, and optionally concentrated into glacial acetic acid (99.5% pure acetic acid), and used as feedstock for the chemical industry. Non-limiting examples of the use of acetic acid include the production of fibers and resins such as cellulose acetate used in making acetate rayon, the production of pharmaceuticals, bleaches, preservatives and photographic chemicals, fertilizers, plastics, nonflammable motion-picture film, photographic film, lacquers, and paint solvents. In addition, the acetic acid obtained by anaerobically fermenting a biomass, as described herein, may be used to make acetate esters which may be used as solvents for various resins in protective coatings and for formulating inks. Such acetate esters include, but are not limited to, amyl, butyl, ethyl, methyl, and propyl acetates which may be used as solvents in quick-drying lacquers, cements and adhesives.

The volatile organic acids obtained from anaerobic fermentation, as described herein, may be used in the synthesis of other chemical products. By way of example only, a volatile organic acid and a mineral may be admixed and reacted to form a composition. This is demonstrated by an exemplary embodiment in which acetic acid, obtained from anaerobic fermentation of a biomass, is admixed and reacted with dolomite (calcium magnesium carbonate) to form calcium magnesium acetate (reaction Scheme 1).

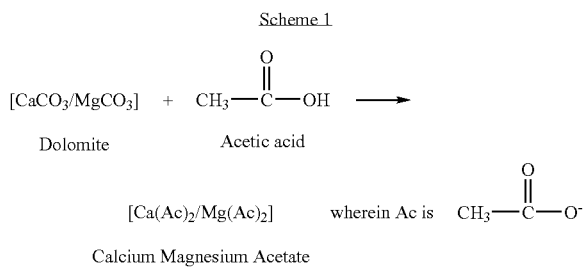

The calcium magnesium acetate formed in this manner may be used as an anti-freeze agent, a deicing agent, or an anti-icing agent. In addition, glacial acetic acid may be used as described above, wherein the glacial acetic acid is formed by concentrating the acetic acid obtained from anaerobic fermentation of a biomass.

Similarly, volatile organic acids may be admixed with an oxide and liquid ammonia and reacted to form a composition. This is demonstrated by an exemplary embodiment in which acetic acid, obtained from anaerobic fermentation of a biomass, is admixed and reacted with zinc oxide to form zinc ammonium acetate (reaction Scheme 2).

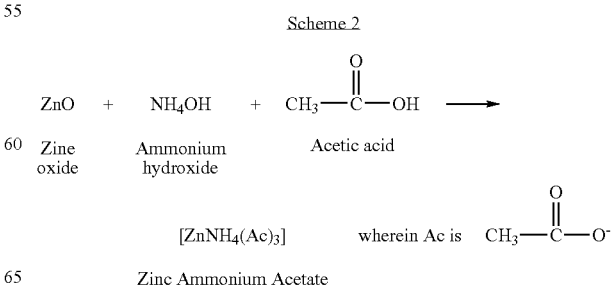

The zinc ammonium acetate formed in this manner may be used as a fertilizer or a seed germination enhancer. Again the glacial acetic acid may also be used, wherein the glacial acetic acid is formed by concentrating the acetic acid obtained from anaerobic fermentation of a biomass.

Hydrogen plus catalysts are used extensively in the chemical industry to hydrogenate a variety of starting materials to create chemical products for further chemical synthesis use. The hydrogen obtained from anaerobic fermentation of a biomass, as described herein, may be used for hydrogenation processes in the chemical industry. Such processes include, but are not limited to, the following examples:

a) Hydrogenation of unsaturated hydrocarbons and aromatics
   e.g. benzene to cyclohexane using Ni—/Pt—Al2O3 catalyst, wherein the cyclohexane, is used as starting material for nylon production or as a solvent,
b) Hydrogenation of ketones and aldehydes
   e.g. acetone to mesityl oxide to methyl isobutyl ketone (MIBK) for use as a solvent
c) Hydrogenation of nitrogen containing compounds
   e.g. nitrobenzene to aniline using a Cu catalysts such as NiS/CuS, wherein the aniline is used as a starting material for dyes, pharmaceuticals, polymers, and solvents.

Hydrogen gas is an environmentally friendly energy source, as it can be used generate electricity without producing greenhouse gas emissions. Thus, a hydrogen based system offers totally clean energy supplies with no pollution. Hydrogen may be produced by a number of processes, including electrolysis of water, thermocatalytic reformation of hydrogen-rich organic compounds such as methane, and biological processes. Biological production of hydrogen provides a wide range of approaches to generate hydrogen, including direct biophotolysis, indirect biophotolysis, photo-fermentations, and dark-fermentation. The fermentation products, such as gases and solvents, produced as described herein, may be used as fuel and/or energy sources for power generation using power generation systems. Such energy and power production applications, include, but are not limited to, powering motor vehicles, running turbines or fuel cells to produce electricity at centralized power stations, running turbines or fuel cells to produce electricity at localized decentralized power stations, and generating heat by direct combustion. The power generation systems include, but are not limited to, internal combustion generators, turbine generators, fuel cells, and such systems may be part of a centralized power station or a decentralized power station. In addition, the electricity obtained locally from the decentralized power station may be used for residential consumption or commercial consumption, or the electricity may be added to the grid and then used residentially or commercially.

The gaseous fermentation products used as fuel or energy sources include, but are not limited to hydrogen, carbon dioxide, carbon monoxide, hydrogen sulfide and methane, wherein the methane may be produced by anaerobic fermentation or may be formed by methanation using the hydrogen and carbon oxides produced by anaerobic fermentation. Methane formation by methanation results by mixing hydrogen and carbon oxides, such as, by way of example only, carbon dioxide and carbon monoxide, and a catalyst such as, by way of example only activated nickel catalysts and NiO/MgO. The methane formed either by methanation or by anaerobic fermentation may be used as a fuel or energy source to generate electricity from fuel cells or to generate heat by combustion in a heat generation system. The heat generation system includes, but is not limited to, furnaces to heat buildings, stove-top, ovens, and barbeques for cooking, and dryers for drying clothes or commercial products such as plastics, polymers, plywood, paper, and pharmaceutical products. Combustion of solvents obtained as fermentation products may be used to generate steam to run turbines, used in internal combustion generators and turbine generators. Such solvent include, but are not limited to, acetone, butanol, ethanol, propanol, isopropanol, 1,2-propanediol and or other solvents.

There are various types of fuel cells, each with particular operating conditions and fuel requirements. The hydrogen produced as described herein may be used in any of them. Alkaline fuel cells (AFC) utilize hydroxyl ions (OH$^-$) as the mobile ion (derived from potassium hydroxide, KOH), operate in the 50 to 200° C. range, and are sensitive to the presence of $CO_2$. Phosphoric acid fuel cells (PAFC) utilize protons (H*) as the mobile ion and operate at approximately 200° C. PAFC systems were the first fuel cells produced commercially and are used as stationary power sources, generating up to 200 kW of electricity. The high operating temperature and corrosive nature of the electrolyte makes them unsuitable for use in mobile and transportation applications. Molten carbonate fuel cells (MCFC) utilize carbonate ions ($CO_3^{2-}$) as the mobile ion, operate at approximately 650° C., and can take $H_2$, $CO_2$, CO, and/or $CH_4$ as fuel, which means they can use natural gas, coal gas, or biogas as fuel sources. Like PAFC, MCFC are used as stationary power sources, generating electricity in the MW range. Solid oxide fuel cells (SOFC) utilize oxygen radicals ($O^2$) as the mobile ion and operate between 500° C. and 1000° C. Like MCFC, SOFC can utilize $H_2$, CO, and/or $CH_4$ as fuel, which means they can use methane, coal gas, or biogas as fuel sources. Carbon dioxide is not utilized as a fuel and is discharged as a waste gas. Like other high-temperature fuel cell systems (PAFC and MCFC) SOFC systems are used as stationary power sources, generating electricity from the low kW to the MW range. Proton exchange membrane fuel cells (PEMFC) utilize hydrogen protons (H$^+$) as the mobile ion, operate in the 50-100° C. range, require pure $H_2$, and are sensitive to the presence of CO. Of all fuel cell systems available, PEMFC systems are especially suitable for mobile and transportation applications, such as engines for cars. Small PEMFC's, in the 1-10 kW range, may be useful for electrical applications for homes.

Anaerobic Fermentation System

Figure 16:
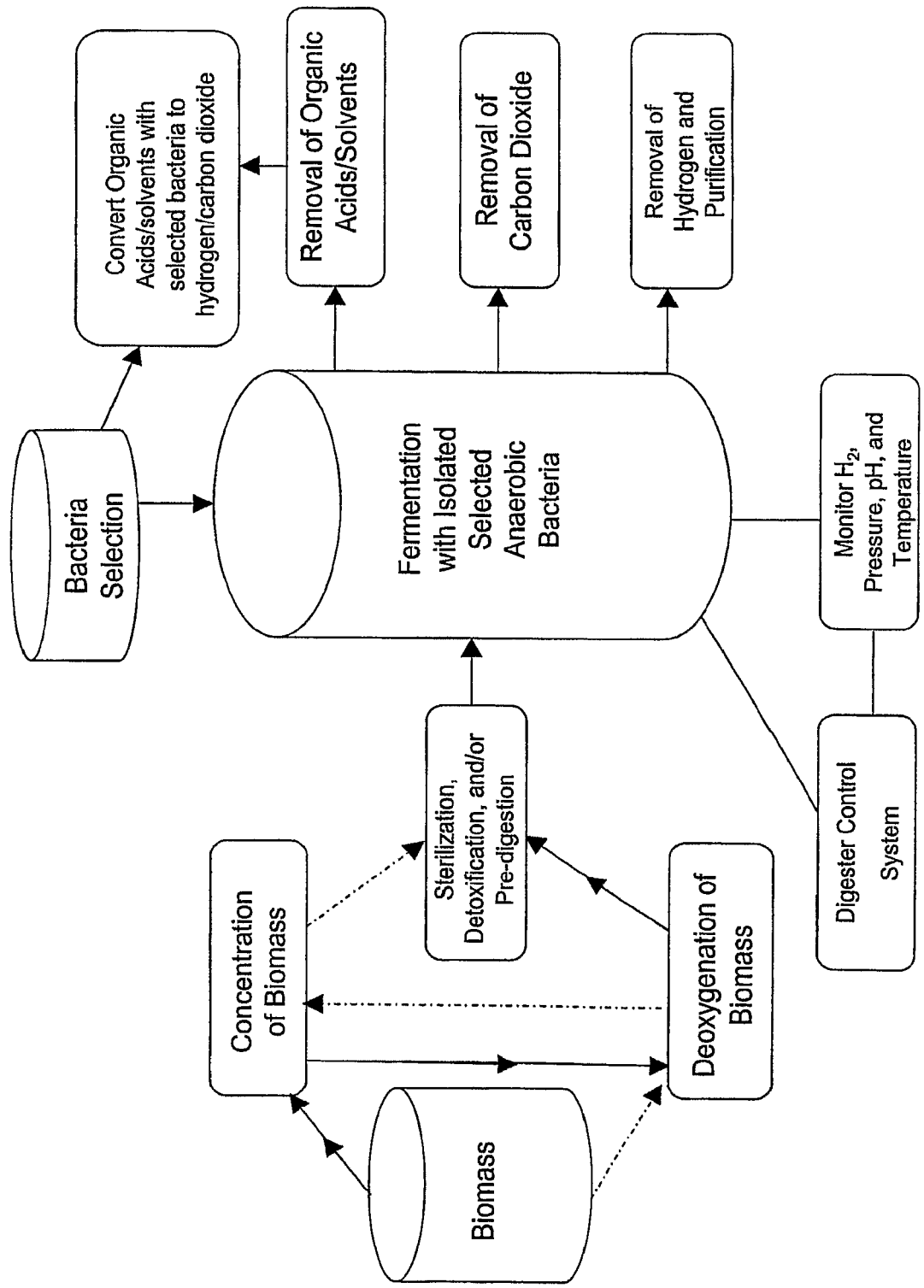
FIG. 16 presents one potential schematic of the machinery components used for hydrogen production.

The anaerobic fermentation system described herein is an assemblage of components, combined to produce chemical products by anaerobically fermenting biomass. FIG. 16 is a schematic representation of a non-limiting example of the components of such an assemblage. The arrows between components are used to illustrate the transportation of material from one component to another, continuous movement of material from one component to another, depiction of the next step in the process or combinations thereof. In addition, each component represented may incorporate a single process, multi step processes, a single device, multiple devices, or combinations thereof.

In FIG. 16 the biomass is pretreated prior to being transported to the anaerobic fermentation digester. The pretreatment process involves concentration adjustment, detoxification, sterilization, deoxygenation, and/or pre-digestion, not necessarily in this order. By way of example only, the biomass may be sterilized and deoxygenated prior to concentration adjustment, detoxification, and/or pre-digestion steps; the biomass may be concentrated prior to sterilization, detoxification, deoxygenation, and/or pre-digestion; the biomass may be sterilized, then deoxygenated, then detoxified, then concentrated, and then pre-digested; the biomass may be detoxified, deoxygenated, then sterilized, and then concentrated; the biomass may be concentrated, then sterilized, then deoxygenated, and then detoxified; or the biomass may be concentrated, then deoxygenated, then detoxified, and then sterilized. The concentration adjustment step may be accomplished using methods which separate solids from liquids, such as, but not limited to, centrifugation and filtration, or the concentration adjustment step may be accomplished using methods which separate solution phase chemicals from liquid such as, but not limited to, reverse osmosis, dialysis and osmosis. The components used to concentrate biomass using such techniques are known to one skilled in the art.

In the operation of the anaerobic fermentation system described herein sterilization can be accomplished using pasteurization and/or acidification. Other methods known in the art may also be used to sterilize the biomass.

Figure 17:
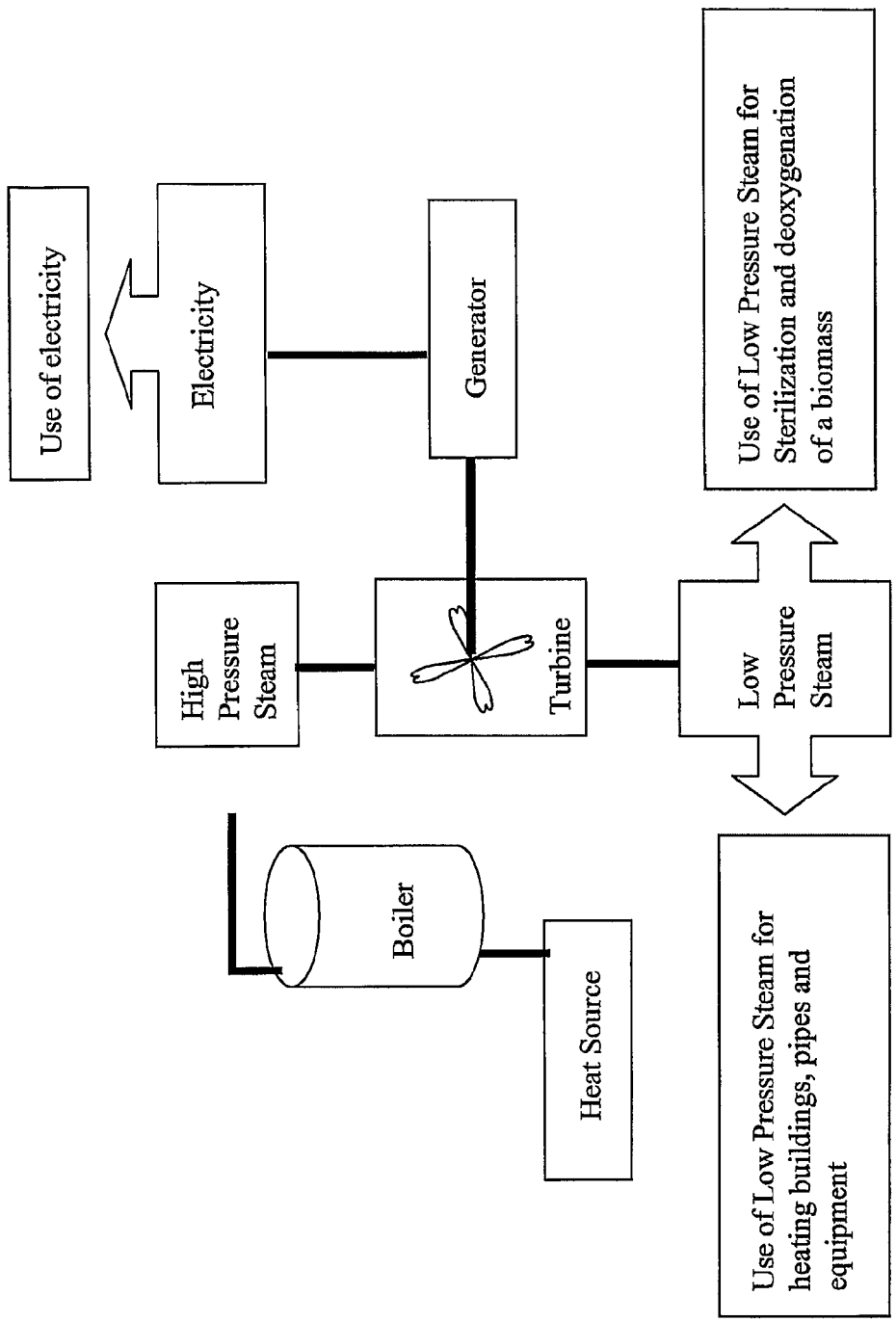
FIG. 17 presents one potential schematic demonstrating the use of a turbine system to generate low pressure steam for sterilization and deoxygenation of a biomass

In the operation of the anaerobic fermentation system described herein deoxygenation can be accomplished using high pressure and low pressure steam. In general high pressure steam is generated with the use of a boiler, although any means to generate high pressure steam may be used. This high pressure steam may be used for deoxygenation, or a pressure reducing valve may be used to lower the pressure, and the low pressure steam may be used for deoxygenation. In another embodiment turbines, including, but not limited to, backpressure turbine generators, are used to both create low pressure steam by reducing the pressure of high pressure steam and generate electricity. The advantage associated with the use of a turbine to generate low pressure steam is that in addition to the low pressure steam being made available for deoxygenation, the turbine can be used to generate electricity which can be used to operate the facility containing the anaerobic digesters. FIG. 17 is a schematic demonstrating the use of a turbine system to generate low pressure steam for sterilization and deoxygenation of a biomass, in conjunction to the generation of electricity for use by the facility, or any other electricity consumer. As seen in FIG. 17, a heat source (i.e. commerically bought or from an anerobic substrate source/reaction) heats the boiler. High pressure steam enters the turbine which causes the blades to turn and thereby turning a generator and creating electricity. Thus the steam turbine generator makes electricity by converting a steam pressure drop into mechanical power to spin a generator. As the high-pressure steam enters the turbine and drives the generator, the lower pressure steam exhausts from the turbine and is used to either heat the facility, sterilize and deoxygenate a biomass, or combinations thereof. In addition, single backpressure turbine generators may be used, or multistage backpressure turbine generators may be used to handle different steam paths form different high pressure steam sources.

After pretreatment the biomass is transported to the anaerobic fermentation digester (FIG. 16), where it is fermented using anaerobic bacteria chosen for the particular biomass present. The conditions inside the anaerobic digester may vary according to the anaerobic bacteria being used, the configuration of the anaerobic digester, the feedstock being converted, the desired productivity of the anaerobic digester, the chemical product being produced, and the form of bacteria (immobilized or free-flowing) used. Mobilized bacteria can be prepared using any methods known by the artisan of ordinary in the arts. In order to optimally operate the anaerobic digester the conditions used to ferment the biomass are monitored, and the fermentation parameter are then controlled to achieve optimal production of chemical product and the maintenance of anaerobic bacteria viability. The fermentation parameters include, but are not limited to, solids content, nutrient solution composition, temperature, gas content, digestion rate, anaerobic bacteria content, agitation, feed and effluent rates, gas production rate, carbon/nitrogen ratio of the feed stock, pressure, pH, and retention time in the digester. These parameters may be monitored continuously or intermittently, using pH sensors, gas sensors, GC's, HPLC's, FIA's, pressure sensors, temperature sensors, optical densitometers, refractometers, and gas flow sensors The operation of the anaerobic fermentation systems described herein may be a continuous process or a batch process. In either approach the anaerobic fermentation parameters, such as, by way of example only, temperature, pH, pressure, gas flow, biomass concentration, and fermentation chemical product concentration, may be monitored and the information used to optimally operate the anaerobic fermentation digester system. The anaerobic digester control system may comprise at least one process control tool; at least one metrology tool to acquire at least one metrology data relating to at least one anaerobic fermentation parameter; a process controller operatively coupled to at least one process control tool and at least one metrology data, and wherein the process controller comprises decision making units, input/output boards, and database units to store at least one metrology data. The decision making unit is used in a feedback control process to acquire metrology tool data from the input/output board and to determine control adjustments based on the metrology tool data and defined operational ranges for the desired anaerobic fermentation parameters. This maintains the anaerobic fermentation parameters within operational ranges and allows for optimal operation of the anaerobic digester. The magnitude of the control adjustments, are modified and returned to the input/output board, whereby by the modified control adjustments are sent to process control tools to adjust operating parameter of the anaerobic fermentation digester and thereby maintain the digester at optimal conditions as defined by the operational ranges.

The type of decision making units incorporated into the anaerobic fermentation systems described herein include, but are not limited to, computers, PROM's (Programmable Read-Only Memory), EPROM's (Erasable Programmable Read-Only Memory) and EEPROM's (Electrically Erasable Programmable Read-Only Memory). The types of metrology tool incorporated into the anaerobic fermentation systems described herein include, but are not limited to, at least one pH sensor, at least one pressure sensor, at least one gas flow sensor, at least one temperature sensor, at least one GC, at least one HPLC, at least one FIA, and combinations thereof. In addition, the type of process control tool incorporated into the anaerobic fermentation systems described herein includes, but is not limited to, a valve, a hotplate, or a heating mantle.

Figure 18:
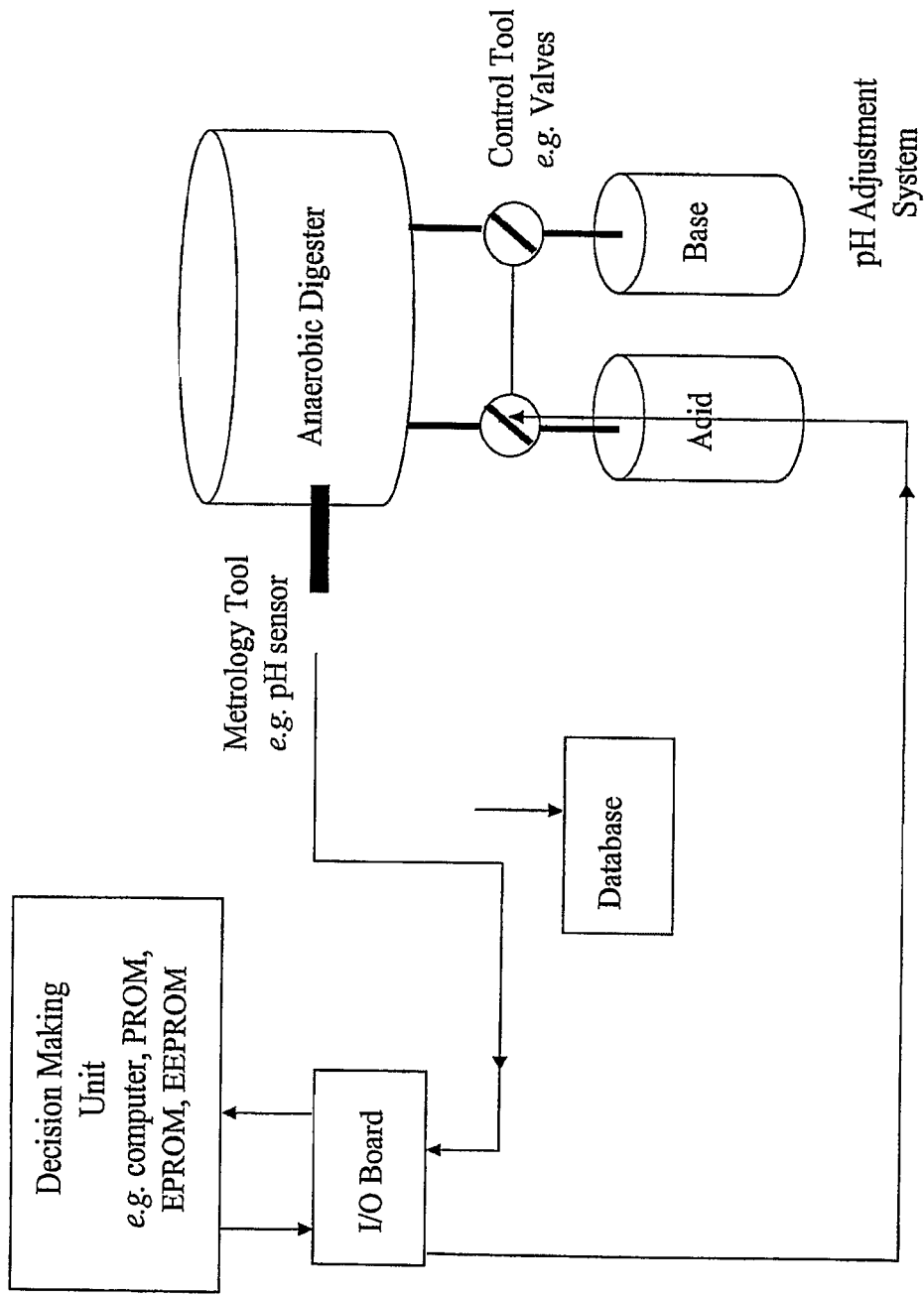
FIG. 18 presents one potential schematic of one embodiment of the anaerobic digester control system

FIG. 18 is a schematic of an embodiment of the anaerobic digester control system, wherein, by example only, the metrology tool is a pH sensor and the operating parameter to be controlled is the pH of the anaerobic fermentation media. Adjustment of the pH is by addition of acid or base from appropriate tanks by control of valves which couple the acid and base tanks to the anaerobic digester. Adjustment occurs to maintain the pH in a defined operational range. The pH sensor information is acquired by the I/O board which sends the information to the decision making unit. Depending on the pH value and the resulting calculated control adjustment, the valve, to either the acid or base tanks, is opened and a predetermined aliquot is added to the digester. The valve is then closed and the process repeats to maintain the digester at optimal pH as defined by the operational range.

ILLUSTRATIVE EXAMPLES

The following examples are provided for illustrative purposes only and not to limit the scope of the claims provided herein.

Example 1

Batch Anaerobic Fermentation of Plant Material

Stem, Leaf, Seed and Vegetable Parts of Bell Pepper Plants

Parts of bell pepper plants, including leaves, stems, vegetables and seeds, is obtained from a bell pepper farm and is shredded using a mulching machine. The shredded material and water are placed into a vat, whereby the mixture is treated with low pressure steam for sterilization and deoxygenation. The steam treatment also assists in degrading cellulosic material for easier fermentation. The sterilized/deoxygenated mixture is then concentrated by removing a portion of the water using a centrifuge system. After centrifugation the concentrated/sterilized/deoxygenated material is pumped into an anaerobic digester which has been deoxygenated by sparging with nitrogen. The anaerobic digester is a modified commercial digester (DCI Inc., St. Cloud, Minn.). After addition of the treated bell pepper material the anaerobic digester is inoculated with a bacterial culture of *Clostridium butyricum*. During fermentation the temperature, pH, pressure, concentration of anaerobic fermentation products and optical density are monitored and changes to the digester operating parameters are adjusted accordingly. Throughout the fermentation process the anaerobic fermentation gas products are collected, separated and purified. Upon completion of the fermentation process the digester is emptied and the slurry is filtered to obtain the liquid which is further processed to obtain the volatile organic acid produced.

Example 2

Continuous Anaerobic Fermentation of Plant Material

Stem, Leaf, Seed and Vegetable Parts of Bell Pepper Plants

Parts of bell pepper plants, including leaves, stems, vegetables and seeds, is obtained from a bell pepper farm and is shredded using a mulching machine. The shredded material and water are placed into a vat, whereby the mixture is treated with low pressure steam for sterilization and deoxygenation. The steam treatment also assists in degrading cellulosic material for easier fermentation. The sterilized/deoxygenated mixture is then concentrated by pumping the slurry through a continuously fed reverse osmosis system (GE Osmonics Corp., Kent, Wash.); thereby a portion of the water is removed. The concentrated/sterilized/deoxygenated slurry is pumped into an anaerobic digester which is continuously anaerobically fermenting biomass and contains a population of *Clostridium butyricum*. The anaerobic digester is a modified commercial digester (DCI Inc., St. Cloud, Minn.). During fermentation the temperature, pH, pressure, concentration of anaerobic fermentation products and optical density are constantly monitored using a digester control system and changes to the digester operating parameters are adjusted continuously by the digester control system. The digester control system is a custom built system, wherein pH sensors, pressure sensors, temperature sensors, and gas sensors are monitored using Lab VIEW NIDAQ software (National Instruments Corporation, Austin, Tex.), running a DAQPad-6508 National Instruments I/O board. Any adjustments needed to the operating parameters are calculated using a laptop computer based on the sensor signals. Throughout the fermentation process the anaerobic fermentation gas products are continuously removed from the digester using a vacuum. The gaseous products are separated and purified using differential compression. The fermenting slurry is recycled through a reverse osmosis system (GE Osmonics Corp., Kent, Wash.) to remove the volatile organic acids produced. The concentration of the organic acids are measured using a gas chromatograph (Model 8610C: SRI Instruments, Torrance, Calif.) equipped with a flame ionization detector, using nitrogen as carrier gas and a fused silica capillary column 0.1 μm×0.53 mm×15 m MXT-WAX (Restek, Bellefonte, Pa.)

Example 3

Utilizing the Enrichment/Isolation System and Knowledge Management System to Identify Optimal Biomass for Bacterial Strains in Producing Hydrogen Anaerobically Using two parallel glass plates approximately 10,000 $cm^3$ in volume, a sealed chamber is formed to house an enrichment/isolation system. In very concentrated spots nutrients are placed within the sealed chamber either by direct placement or metering in with a hose. Different types of nutrients are placed away from each other a distance so that different spatial zones of bacteria around the nutrients may form. Nutrients used are organic acids, diesel, food waste fats and cellulose. Bacteria used in the sealed chamber are harvested from decomposing bell peppers. The bacteria are introduced into sealed chamber so that they use the nutrients as a food source. After 3-4 weeks bacterial samples around the nutrients are taken out using a syringe or tool which is non-evasive. The bacterial samples are tested to determine whether the bacteria are primary or secondary users of the food source. The bacteria are isolated, put on defined medium to test what they use as nutrients. Two particular indicator tests that are preformed are the nitrate and catalase tests. The bacteria are also assayed for their production of hydrogen at different growth conditions involving variation in temperature, pressure, pH, fermentation products, exposure to various natural gases or compounds, drug efficacy, compound toxicity or survivability.

Information regarding which types of bacteria species uses what particular type of nutrients as a food source and optimal bacterial growth conditions for producing hydrogen are entered into the Knowledge Management System database. The Knowledge Management System houses data that can be quickly accessed and manipulated into a user friendly form such as a graph or spreadsheet. In particular, the Knowledge Management System can narrow down which bacteria uses particular nutrients for producing a specific amount of hydrogen.

All references cited herein, including patents, patent applications, and publications, are hereby incorporated by reference in their entirety. All of the methods disclosed and claimed herein can be made and executed without undue experimentation in light of the present disclosure. It will be apparent to those of skill in the art that variations may be applied to the methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. An anaerobic fermentation apparatus using a population of substantially purified anaerobic bacterial strain for anaerobically fermenting a biomass into a chemical product comprising: (i) a sterilization and deoxygenation system; (ii) an anaerobic digester containing a population of substantially purified anaerobic bacteria and equipped with an anaerobic digester control system; (iii) a plurality of pipelines and pumps for introducing and re-circulating biomass, and (iv) removal pipelines connected to the anaerobic digester for removing a chemical product from the anaerobic digester; wherein the population of substantially purified anaerobic bacterial strain has not been subjected to a heatshocking process.

2. The anaerobic fermentation apparatus of claim 1, wherein the anaerobic fermentation apparatus is a component of an assemblage for generating power.

3. The anaerobic fermentation apparatus of claim 1, wherein the chemical product is selected from the group consisting of a gaseous chemical product, a non-gaseous chemical product, and combinations thereof.

4. The anaerobic fermentation apparatus of claim 1, wherein the anaerobic digester control system is used to optimally operate the anaerobic digester and comprises: an at least one process control tool; an at least one metrology tool to acquire at least one metrology data relating to at least one anaerobic fermentation parameter; an a process controller operatively coupled to the at least one process control tool and the at least one metrology data, wherein the process controller comprises a decision making unit, an input/output board, and a database unit to store the at least one metrology data.

5. The anaerobic fermentation apparatus of claim 1, wherein the biomass comprises a material selected from the group consisting of energy crops, surplus agricultural products, waste from sugar production and processing facilities, waste from fruit processing industries, waste from pulp and paper mills, silvaculture residues, waste from wood processing, waste from agricultural product processing, food waste, solids isolated from fermentation cultures, municipal sewer waste, animal manure, animal urine, animal parts, fish parts, and combinations thereof.

* * * * *

UNITED STATES PATENT AND TRADEMARK OFFICE
CERTIFICATE OF CORRECTION

| | | |
|---|---|---|
| PATENT NO. | : 8,501,463 B2 | Page 1 of 1 |
| APPLICATION NO. | : 11/912881 | |
| DATED | : August 6, 2013 | |
| INVENTOR(S) | : Cox et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1633 days.

Signed and Sealed this
Tenth Day of February, 2015

Michelle K. Lee
*Deputy Director of the United States Patent and Trademark Office*